(12) United States Patent
McKenna, Jr. et al.

(10) Patent No.: US 7,727,763 B2
(45) Date of Patent: Jun. 1, 2010

(54) DIFFERENTIATION OF MULTI-LINEAGE PROGENITOR CELLS TO RESPIRATORY EPITHELIAL CELLS

(75) Inventors: David H. McKenna, Jr., Saint Paul, MN (US); Barbara M. Tigges, Hudson, WI (US); Michael J. Berger, Falcon Heights, MN (US)

(73) Assignees: BioE, LLC, St. Paul, MN (US); Regents of the University of Minnesota, St. Paul, MN (US)

( * ) Notice: Subject to any disclaimer, the term of this patent is extended or adjusted under 35 U.S.C. 154(b) by 0 days.

(21) Appl. No.: 11/736,273

(22) Filed: Apr. 17, 2007

(65) Prior Publication Data

US 2007/0249047 A1    Oct. 25, 2007

Related U.S. Application Data

(60) Provisional application No. 60/792,511, filed on Apr. 17, 2006.

(51) Int. Cl.
    *C12N 5/02* (2006.01)
(52) U.S. Cl. .................. 435/377; 435/331; 435/332; 435/335; 435/375
(58) Field of Classification Search ............... None
    See application file for complete search history.

(56) References Cited

U.S. PATENT DOCUMENTS

| | | |
|---|---|---|
| 5,004,681 A | 4/1991 | Boyse et al. |
| 5,130,144 A | 7/1992 | Civin |
| 5,192,553 A | 3/1993 | Boyse et al. |
| 5,453,357 A | 9/1995 | Hogan |
| 5,486,359 A | 1/1996 | Caplan et al. |
| 5,580,714 A | 12/1996 | Polovina |
| 5,744,347 A | 4/1998 | Wagner et al. |
| 5,750,397 A | 5/1998 | Tsukamoto et al. |
| 5,789,147 A | 8/1998 | Rubinstein et al. |
| 5,827,735 A | 10/1998 | Young et al. |
| 5,827,740 A | 10/1998 | Pittenger |
| 5,830,651 A | 11/1998 | Cauley et al. |
| 5,843,780 A | 12/1998 | Thomson |
| 5,877,299 A | 3/1999 | Thomas et al. |
| 5,908,782 A | 6/1999 | Marshak et al. |
| 5,928,214 A | 7/1999 | Rubinstein et al. |

(Continued)

FOREIGN PATENT DOCUMENTS

EP    03 01 7676.2    8/2004

(Continued)

OTHER PUBLICATIONS

Abe et al., "Cells Derived from the Circulation Contribute to the Repair of Lung Injury," *Am. J. Respir. Crit. Care Med.*, 2004, 170 (11):1158-1163.

(Continued)

*Primary Examiner*—Q. Janice Li
(74) *Attorney, Agent, or Firm*—Fish & Richardson P.C.

(57) ABSTRACT

Fetal blood multi-lineage progenitor cells that are capable of a wide spectrum of transdifferentiation are described, as well as methods of differentiating the progenitor cells into type II alveolar cells.

7 Claims, 39 Drawing Sheets

U.S. PATENT DOCUMENTS

| | | |
|---|---|---|
| 5,942,225 A | 8/1999 | Bruder et al. |
| 5,965,436 A | 10/1999 | Thiede et al. |
| 5,968,829 A | 10/1999 | Carpenter |
| 6,030,836 A | 2/2000 | Thiede et al. |
| 6,103,530 A | 8/2000 | Carpenter |
| 6,140,121 A | 10/2000 | Ellington et al. |
| 6,200,806 B1 | 3/2001 | Thomson |
| 6,251,669 B1 | 6/2001 | Luskin |
| 6,280,718 B1 | 8/2001 | Kaufman et al. |
| 6,306,575 B1 | 10/2001 | Thomas et al. |
| 6,322,784 B1 | 11/2001 | Pittenger et al. |
| 6,328,960 B1 | 12/2001 | McIntosh et al. |
| 6,387,367 B1 | 5/2002 | Davis-Sproul et al. |
| 6,432,711 B1 | 8/2002 | Dinsmore et al. |
| 6,436,704 B1 | 8/2002 | Roberts et al. |
| 6,491,918 B1 | 9/2002 | Thomas et al. |
| 6,461,645 B1 | 10/2002 | Boyse et al. |
| 6,465,247 B1 | 10/2002 | Weissman et al. |
| 6,482,926 B1 | 11/2002 | Thomas et al. |
| 6,491,917 B1 | 12/2002 | Thomas et al. |
| 6,498,034 B1 | 12/2002 | Strobl |
| 6,569,427 B1 | 5/2003 | Boyse et al. |
| 6,605,275 B1 | 8/2003 | Boyse et al. |
| 6,645,727 B2 | 11/2003 | Thomas et al. |
| 6,680,198 B1 | 1/2004 | Snyder et al. |
| 6,709,864 B1 | 3/2004 | Pittenger et al. |
| 6,740,493 B1 | 5/2004 | Long et al. |
| 6,750,326 B2 | 6/2004 | Thomas et al. |
| 6,761,883 B2 | 7/2004 | Weissman et al. |
| 6,767,737 B1 | 7/2004 | Wilson et al. |
| 6,777,231 B1 | 8/2004 | Katz et al. |
| 6,777,233 B2 | 8/2004 | Carpenter |
| 6,800,480 B1 | 10/2004 | Bodnar et al. |
| 6,835,377 B2 | 12/2004 | Goldberg et al. |
| 6,852,533 B1 | 2/2005 | Rafii et al. |
| 6,875,430 B2 | 4/2005 | McIntosh et al. |
| 6,887,704 B2 | 5/2005 | Peled et al. |
| 6,911,201 B1 | 6/2005 | Merchav et al. |
| 6,946,293 B1 | 9/2005 | Lu et al. |
| 6,962,698 B1 | 11/2005 | Peled et al. |
| 6,986,887 B2 | 1/2006 | Lawman et al. |
| 6,991,897 B2 | 1/2006 | Smith et al. |
| 7,015,037 B1 | 3/2006 | Furcht et al. |
| 7,045,148 B2 | 5/2006 | Hariri |
| 7,122,178 B1 | 10/2006 | Simmons et al. |
| 7,160,723 B2 | 1/2007 | Collins et al. |
| 7,255,879 B2 | 8/2007 | Hariri |
| 2001/0034061 A1 | 10/2001 | Csete et al. |
| 2001/0046489 A1 | 11/2001 | Habener et al. |
| 2002/0012903 A1 | 1/2002 | Goldman et al. |
| 2002/0028510 A1 | 3/2002 | Sanberg et al. |
| 2002/0045196 A1 | 4/2002 | Mahoney et al. |
| 2002/0064519 A1 | 5/2002 | Bruder et al. |
| 2002/0068045 A1 | 6/2002 | Reubinoff et al. |
| 2002/0132987 A1 | 9/2002 | Anderson |
| 2002/0164308 A1 | 11/2002 | Reubinoff et al. |
| 2002/0164790 A1 | 11/2002 | Warburton et al. |
| 2002/0164794 A1 | 11/2002 | Wernet |
| 2002/0168763 A1 | 11/2002 | Yan et al. |
| 2002/0177227 A1 | 11/2002 | Kraus et al. |
| 2002/0192816 A1 | 12/2002 | Roberts et al. |
| 2003/0003084 A1 | 1/2003 | Seshi |
| 2003/0027233 A1 | 2/2003 | Collins et al. |
| 2003/0032179 A1 | 2/2003 | Hariri |
| 2003/0092078 A1 | 5/2003 | Thomas et al. |
| 2003/0113910 A1 | 6/2003 | Levanduski |
| 2003/0134416 A1 | 7/2003 | Yamanishi et al. |
| 2003/0157078 A1 | 8/2003 | Hall et al. |
| 2003/0161818 A1 | 8/2003 | Weiss et al. |
| 2003/0165852 A1 | 9/2003 | Schueler et al. |
| 2003/0180269 A1 | 9/2003 | Hariri |
| 2003/0203483 A1 | 10/2003 | Seshi |
| 2003/0235563 A1 | 12/2003 | Strom et al. |
| 2003/0235909 A1 | 12/2003 | Hariri et al. |
| 2004/0018621 A1 | 1/2004 | Reid et al. |
| 2004/0028660 A1 | 2/2004 | Hariri et al. |
| 2004/0058398 A1 | 3/2004 | Sarvetnick et al. |
| 2004/0058412 A1 | 3/2004 | Ho et al. |
| 2004/0107453 A1 | 6/2004 | Furcht et al. |
| 2004/0121464 A1 | 6/2004 | Rathjen et al. |
| 2004/0137612 A1 | 7/2004 | Baksh et al. |
| 2004/0142463 A1 | 7/2004 | Walker et al. |
| 2004/0161419 A1 | 8/2004 | Strom et al. |
| 2004/0171147 A1 | 9/2004 | Hariri |
| 2004/0203142 A1 | 10/2004 | Rai |
| 2004/0219136 A1 | 11/2004 | Hariri |
| 2004/0228847 A1 | 11/2004 | Goldschmidt-Clermont et al. |
| 2004/0259254 A1 | 12/2004 | Honmou et al. |
| 2005/0019865 A1 | 1/2005 | Kihm et al. |
| 2005/0019908 A1 | 1/2005 | Hariri |
| 2005/0019911 A1 | 1/2005 | Gronthos et al. |
| 2005/0032209 A1 | 2/2005 | Messina et al. |
| 2005/0037493 A1 | 2/2005 | Mandalam et al. |
| 2005/0048035 A1 | 3/2005 | Fraser et al. |
| 2005/0053588 A1 | 3/2005 | Yin |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0059147 A1 | 3/2005 | Seshi |
| 2005/0063961 A1 | 3/2005 | Friedlander et al. |
| 2005/0074435 A1 | 4/2005 | Casper et al. |
| 2005/0095703 A1 | 5/2005 | Semb et al. |
| 2005/0106554 A1 | 5/2005 | Palecek et al. |
| 2005/0118715 A1 | 6/2005 | Hariri et al. |
| 2005/0124003 A1 | 6/2005 | Atala et al. |
| 2005/0142118 A1 | 6/2005 | Wernet |
| 2005/0158289 A1 | 7/2005 | Simmons et al. |
| 2005/0176139 A1 | 8/2005 | Chen et al. |
| 2005/0181502 A1 | 8/2005 | Furcht et al. |
| 2005/0255592 A1 | 11/2005 | Collins et al. |
| 2005/0260748 A1 | 11/2005 | Chang et al. |
| 2005/0260751 A1 | 11/2005 | Lucas et al. |
| 2006/0008450 A1 | 1/2006 | Verfaillie et al. |
| 2006/0030039 A1 | 2/2006 | Chen et al. |
| 2006/0037092 A1 | 2/2006 | Lawman et al. |
| 2006/0040392 A1 | 2/2006 | Collins et al. |
| 2006/0078993 A1 | 4/2006 | Phan et al. |
| 2006/0134636 A1 | 6/2006 | Stanton |
| 2006/0141493 A1 | 6/2006 | West et al. |
| 2006/0154366 A1 | 7/2006 | Brown et al. |
| 2006/0206953 A1 | 9/2006 | Lanza et al. |
| 2007/0292398 A1 | 12/2007 | Collins |

FOREIGN PATENT DOCUMENTS

| | | |
|---|---|---|
| WO | WO 90/11354 | 10/1990 |
| WO | WO 91/01140 | 2/1991 |
| WO | WO 93/04169 | 3/1993 |
| WO | WO 02/36751 | 5/2002 |
| WO | WO 03/055989 | 7/2003 |
| WO | WO 03/068937 | 8/2003 |
| WO | WO 03/078610 | 9/2003 |
| WO | WO 2004/024875 | 3/2004 |
| WO | WO 2004/029208 | 4/2004 |
| WO | WO 2005/017132 | 2/2005 |

OTHER PUBLICATIONS

Ali et al., "Derivation of Type II Alveolar Epithelial Cells from Murine Embryonic Stem Cells," *Tissue Eng.*, 2002, 8(4):541-550.

Berger et al., "Differentiation of Umbilical Cord Blood-Derived Multi-Lineage Progenitor Cells into Respiratory Epithelial Cells," *ISCT Berlin 2006*, Abstract only.

Berger et al., "Differentiation of Umbilical Cord Blood-Derived Multi-Lineage Progenitor Cells Into Respiratory Epithelial Cells," *International Society for Cellular Therapy*, Berlin, presentation No. 258 on May 6, 2006, abstract.

Berger et al., "Differentiation of Umbilical Cord Blood-Derived Multi-Lineage Progenitor Cells into Respiratory Epithelial Cells," *Cytotherapy*, 2006, 8(5):480-487.

Bigbee et al., "Monoclonal antibodies specific for the M- and N-forms of human glycophorin A," *Mol. Immunol.*, 1983, 20(12):1353-1362.

Bradley, "Modifying the mammalian genome by gene targeting," *Curr. Opin. Biotechnol.*, 1991, 2:823-829.

Chomczynski, "A Reagent for the Single-Step Simultaneous Isolation of RNA, DNA and Proteins from Cell and Tissue Samples," *BioTechniques*, 1993, 15(3):532-537.

Cole et al., "The EBV-Hybridoma Technique and Its Application to Human Lung Cancer," *Monoclonal Antibodies and Cancer Therapy*, 1985, Alan R. Liss, Inc., pp. 77-96.

Coraux et al,, "Embryonic Stem Cells Generate Airway Epithelial Tissue," *Am. J. Respir. Cell Mol. Biol.*, 2005, 32:87-92.

Cote et al., "Generation of human monoclonal antibodies reactive with cellular antigens," *Proc. Natl. Acad. Sci. USA*, 1983, 80:2026-2030.

Davies et al,, "Bone Marrow Stem Cells Do Not Repopulate the Healthy Upper Respiratory Tract," *Pediatr. Pulmonol.*, 2002, 34(4):251-256.

Eggens et al., "Specific Interaction between $Le^x$ and $Le^x$ Determinants. A possible basis for cell recognition in preimplantation embryos and in embryonal carcinoma cells," *J. Biol. Chem.*, 1989, 264(16):9476-9484.

Forraz et al., "AC133$^x$ umbilical cord blood progenitors demonstrate rapid self-renewal and low apoptosis," *Br. J. Haematol.*, 2002, 119:516-524.

Forraz et al., "Characterization of a Lineage-Negative Stem-Progenitor Cell Population Optimized for Ex Vivo Expansion and Enriched for LTC-IC," *Stem Cells*, 2004, 22:100-108.

Forraz et al., "Haemopoietic and neuroglial progenitors are promoted during cord blood ex vivo expansion," *Br. J. Haematol.*, 2002, 119:888.

Fowler and Greenspan, "Application of Nile Red, a Fluorescent Hydrophobic Probe, for the Detection of Neutral Lipid Deposits in Tissue Sections, Comparison with Oil Red O," *J. Histochem. Cytochem.* 1985, 33(8):833-836.

Goodwin et al., "Multilineage Differentiation Activity by Cells Isolated From Umbilical Cord Blood: Expression of Bone, Fat, and Neural Markers," *Biol. Blood Marrow Transplant*, 2001, 7:581-588.

Jaiswal et al., "Osteogenic Differentiations Purified, Culture-Expanded Human Mesenchymal Stem Cells in Vitro," *J. Cell. Biochem*, 1997, 64:295-312.

Jennings et al., "CD9 cluster workshop report: cell surface binding and functional analysis," *Leukocyte Typing V*, 1995, vol. 2, Oxford University Press, Schlossmarm (ed.), pp. 1249-1251.

Jiang et al., "Pluripotency of mesenchymal stem cells derived from adult marrow," *Nature*, 2002, 418 6893:41-49.

Kannagi et al., "A Series of Human Erythrocyte Glycosphingolipids Reacting to the Monoclonal Antibody Directed to a Developmentally Regulated Antigen, SSEA-1," *J. Biol. Chem.*, 1982, 257(24):14865-14874.

Kay et al., "Gene therapy," *Proc. Natl. Acad. Sci. USA*, 1997, 94:12744-12746.

Kögler et al., "A New Human Somatic Stem Cell from Placental Cord Blood with Intrinsic Pluripotent Differentiation Potential," *J. Exp. Med.*, 2004, 200(2):123-135.

Köhler and Milstein, "Continuous cultures of fused cells secreting antibody of predefined specificity," *Nature*, 1975,256:495-497.

Kotton et al., "Failure of Bone Marrow to Reconstitute Lung Epithelium," *Am. J. Respir. Cell Mol. Biol.*, 2005, 33:328-334.

Kozbor and Roder, "The production of monoclonal antibodies from human lymphocytes," *Immunology Today*, 1983, 4:72-79.

Krause et al., "Multi-Organ, Multi-Lineage Engraftment by a Single Bone Marrow-Derived Stem Cell," *Cell*, 2001, 105:369-377.

Lam et al., "Preclinical ex vivo expansion of cord blood hematopoietic stem and progenitor cells; duration of culture; the media, serum supplements, and growth factors used; and engraftment in NOD/SCID mice," *Transfusion*, 2001, 41:1567-1576.

Lanza et al., "cDNA Cloning and Expression of Platelet p24/CD9. Evidence for a new family of multiple membrane-spanning proteins," *J. Biol. Chem.*, 1991, 266(16):10638-10645.

Madlambayan et al., "Controlling Culture Dynamics for the Expansion of Hematopoictic Stem Cells," *J. Hematother. Stem Cell Res.*, 2001, 10:481-492.

Magnani et al, "Monoclonal Antibodies PMN 6, PMN 29, and PM-81 Bind Differently to Glycolipids Containing a Sugar Sequence Occurring in Lacto-N-Fucopentaose III," *Arch. Biochem. Biophys.*, 1984, 233(2):501-506.

McGuckin et al., "Colocalization Analysis of Sialomucins CD34 and CD164," *Stem Cells*, 2003, 21:162-170.

McGuckin et al, "Multiparametric analysis of immature cell populations in umbilical cord blood and bone marrow," *Eur. J. Haematol.*, 2003, 71:341-350.

McGuckin et al., "Production of stem cells with embryonic characteristics from human umbilical cord blood," *Cell Prolif.*, 2005, 38:245-255.

McGuckin et al., "Thrombopoietin, flt3-ligand and c-kit-ligand modulate *HOX* gene expression in ex and in cord blood CD133$^+$ cells," *Cell Prolif.*, 2004, 37:295-306.

McGuckin et al., "Umbilical cord blood stem cells can expand hematopoietic and neuroglial progenitors in vitro," *Experimental Cell Research*, 2004, 295:350-359.

Neuringer and Randell, "Stem cells and repair of lung injuries," *Respir. Res.*, 2004, 5:6-14.

Noia et al., "A Novel Route of Transplantation of Human Cord Blood Stem Cells in Preimmune Fetal Sheep: The intracelomie Cavity," *Stem Cells*, 2003, 21:638-646.

Outram et al., "Erythromyeloid lineage fidelity is conserved in erythroleukaemia," *Leukocyte Research.* 1988, 12(8):651-657.

Panoskalisis-Mortari et al., "Differentiation of Type II Pneumocyte-Like Cells from Murine Bone Marrow-Derived Multipotent Adult Progenitor Cells (MAPCs) In Vitro," *Am. Thoracic Soc. 100$^{th}$ International Conference*, Florida, May 21-26, 2004, Abstract.

Perez et al., "Human Cord Blood derived Stem Cells Differentiated into Hormone-Expressing Islet Cell-like Aggregates to Produce Insulin as an Alternative to Pancreatic transplant for diabetic and pancreatic Cancer Patients," *Stem Cell Research and Therapeutics Conference*, San Diego, CA, Apr. 11-12, 2005, 4 pages.

Pittenger et al., "Multilineage Potential of Adult Human Mesenchymal Stem Cells," *Science*, 1999, 284:143-147.

Rippon et al., "Derivation of Distal Lung Epithelial Progenitors from Murine Embryonic Stem Cells Using a Novel Three Step Differentiation Protocol," *Stem Cells*, 2006, 24:1389-1398.

Rubinstein et al., "Anti-Platelet Antibody Interactions with Fcγ Receptor," *Sem. Thromb. Hemostasis*, 1995, 21:10-22.

Rutella et al., "Identification of a Novel Subpopulation of Human Cord Blood CD34$^-$CD133$^-$CD7$^-$CD45$^+$Lineage$^-$Cells Capable of Lymphoid/NK Cell Differentiation After In Vitro Exposure to IL-15," *J. Immunol.*, 2003, 171:2977-2988.

Samadikuchaksaraei et al., "Derivation of Distal Airway Epithelium from Human Embryonic Stem Cells," *Tissue Eng.*, 2006, 12(4):867-875.

Solter and Knowles, "Monoclonal antibody defining a stage-specific mouse embryonic antigen (SSEA-1)," *Proc. Natl. Acad. Sci. USA*, 1978, 75 11:5555-5569.

Telen and Balk, "Human red cell antigens. IV. The abnormal sialoglycoprotein of Gerbich-negative red cells," *Transfusion*, 1987, 27:309-314.

Terai et al, "Immortalization of Human Fetal Cells: The Life Span of Umbilical Cord Blood-derived Cells Can Be Prolonged without Manipulating p16$^{INK4a}$/RB Braking Pathway," *Mol. Biol. Cell*, 2005, 16:1491-1499.

Thomas and Capecchi, "Site-Directed Mutagenesis by Gene Targeting in Mouse Embryo-Derived Stem cells," *Cell*, 1987, 51:503-512.

Van Haaften and Thébaud, "Adult Bone Marrow-Derived Stem Cells for the Lung: Implications for Pediatric Lung Diseases," *Pediatr. Res.*, 2006, 59:94R-99R.

Van Vranken et al., "Coculture of Embryonic Stem Cells with Pulmonary Mesenchyme: A Microenvironment That Promotes Differentiation of Pulmonary Epithelium," *Tissue Eng.*, 2005, 11:1177-1187.

Von dem Borne and Moderman, "Cluster report: CD9," *Leukocyte Typing IV*, 1989, Oxford University Press, W. Knapp (ed), pp. 989-992.

Wang et al., "Adult stem cells from bone marrow stroma differentiate into airway epithelial cells: Potential therapy for cystic fibrosis," *Proc. Natl. Acad. Sci, USA*, 2005, 102(1):186-191.

Whiting et al., "Three-dimensional analysis of CD34 sialomucin distribution on cord blood and bone marrow," *Br. J. Haematol*, 2003, 122:771-777.

Wright and Tomlinson, "The ins and outs of the transmembrane 4 superfamily," *Immunol. Today*, 1994, 15(12): 5888-594.

Xiao et al., "Transplantation of a Novel Cell Line Population of Umbilical Cord Blood Stem Cells Ameliorates Neurological Deficits Associated with Ischemic Brain Injury," *Stem Cells and Development*, 2005, 14:722-733.

Yoon et al., "Clonally expanded novel multipoint stem cells from human bone marrow regenerate myocardium after myocardial infarction," *J. Clin. Invest.*, 2005, 115(2):326-338.

Baksh et al., "Adult mesenchymal stem cells: characterization, differentiation, and application in cell and gene therapy," *J. Cell. Mol. Med.*, 2004, 8(3):301-316.

Belov et al., "Immunophenotyping of leukemias using a cluster of differentiation antibody microarray," *Cancer Res.*, 2001, 61(11):4483-4489.

Bensidhoum et al,, "Homing of in vitro expanded Stro-1⁻ or Stro-1⁺ human mesenchymal stem cells into the NOD/SCID mouse and their role in supporting human CD34 cell engraftment," *Blood*, 2004, 103:3313-3319.

Bieback et al., "Critical Parameters for the Isolation of Mesenchymal Stem Cells from Umbilical Cord Blood," *Stem Cells*, 2004, 22:625-634.

Cadet et al., "A Functionally Coupled μ3-Like Opiate Receptor/Nitric Oxide Regulatory Pathway in Human Multi-Lineage Progenitor Cells," *J. Immunol.*, 2007, 179:5839-5844.

Choi et al., "Chondrogenic differentiation of human umbilical cord blood-derived multilineage progenitor cells in atelocollagen," *Cytotherapy*, 2008, 0:1-9.

D'Ippolito et al., "Marrow-isolated adult multilineage inducible (Miami) cells, a unique population of postnatal young and old human cells with extensive expansion and differentiation potential," *J. Cell Sci.*, 2004, 117:2971-2981.

Erices et al., "Mesenchymal progenitor cells in human umbilical cord blood," *Br. J. Haematol.*, 2000, 109:235-242.

Hou et al., "Study of in vitro expansion and differentiation into neuron-like cells of human umbilical cord blood mesenchyrnal stem cells," *Chin. J. Hematol.*, 2002, 23(8):414-419 (English Abstract only).

Jäger and Krauspe, "Antigen expression of cord blood derived stem cells under osteogenic stimulation in vitro," *Cell Biology International*, 2007, 31:950-957.

Jones et al., "Isolation and Characterization of Bone Marrow Multipoteritial Msenchymal Progenitor Cells," *Arth. Rheum.*, 2002, 46(I2):3349-3360.

Kern et al., "Comparative Analysis of Mesenchymal Stem Cells from Bone Marrow, Umbilical Cord Blood, or Adipose Tissue," *Stem Cells*, 2006, 24:1294-1301.

Kobune et al., "Telomerized human multipotent mesenchyrnal cells can differentiate into hematopoietic and cobblestone area—supporting cells," *Exp Hematol.*, 2003, 31:715-722.

Kögler et al., "Cytokine production and hematopoiesis supporting activity of cord blood—derived unrestricted somatic stem cells," *Exp. Hematol.*, 2005, 33:573-583.

Lakshmipathy et al., "Efficient Transfection of Embryonic and Adult Stem Cells," *Stem Cells*, 2004, 22:531-543.

Lee et al., "Isolation of multipotent mesenchymal stem cells from umbilical cord blood," *Blood*, 2004, 103(5):1669-1675.

Lodie et al., "Systematic analysis of reportedly distinct populations of multipotent bone marrow-derived stem cells reveals a lack of distinction," *Tissue Eng.*, 2002, 8(5):739-751.

Meng et al., "Endometrial regenerative cells: A novel stem cell population," *J. Translational Med.*, 2007, 5:57.

Phinney and Prockop, "Concise Review: Mesenchymal Stem/Multipotent Stromal Cells: The State of Transdifferentiation and Modes of Tissue Repair—Current Views," *Stem Cells*, 2007, 25:2896-2902.

Pittenger et al., "Adult mesenchymal stem cells: potential For muscle and tendon regeneration and use in gene therapy," *J. Musculoskel. Neuron. Interact.*, 2002, 2(4):309-320.

Rosada et al., "The human umbilical cord blood: A potential source for osteoblast progenitor cells," *Calcified Tissue International*, 2003 72:135-42.

Sakaguchi et al., "Comparison of Human Stem Cells Derived from Various Mesenchymal Tissues," *Arth. Rheum*, 2005, 52(8):2521-2529.

Simonsen et al., "Telomerase expression extends the proliferative life-span and maintains the osteogenic potential of human bone marrow stromal cells," *Nat. Biotechnol.*, 2002, 20:592-596.

Stefano et al., "Endogenous morphine/nitric oxide-coupled regulation of cellular physiology and gene expression: Implications for cancer biology," *Semin. Cancer Biol.*, 2008, 18(3):199-210.

Sueblinvong et al., "Derivation of Lung Epithelium from Human Cord Blood-derived Mesenchymal Stem Cells," *Am. J. Respir. Crit. Care Med.*, 2008, 177:701-71.

Tocci and Forte, "Mesenchymal stem cell: use and perspectives," *Hematol. J.*, 2003, 4(2):92-96.

Wagner et al., "Comparative characteristics of mesenchymal stem cells from human bone marrow, adipose tissue, and umbilical cord blood," *Exp. Hematol.*, 2005, 33:1402-4416.

Office Action mailed Feb. 6, 2008 in U.S. Appl. No. 11/208,873, 21 pages.

International Search Report/Written Opinion mailed Apr. 27, 2007 in PCT/US06/33129, 9 pages.

Supplementary Search Report mailed Nov. 28, 2007 in EP 05 73 6785, 6 pages.

International Search Report/Written Opinion mailed Dec. 12, 2006 in PCT/US2005/13244, 7 pages.

Lechner et al., "Clonal Growth of Epithelial Cells from Normal Adult Human Bronchus," *Cancer Research*, 1981, 41:2294-2304.

Anthony Atala, U.S. Appl. No. 60/335,878, "Methods of isolation, expansion and differentiation of human fetal stem cells front amniotic fluid and therapeutic uses thereof," Nov. 15, 2001.

Anthony Atala, U.S. Appl. No. 60/356,295. "Methods of isolation. expansion and differentition of human fetal stem cells from chorionic villus and amniotic fluid, and therapeutic uses thereof," Feb. 13, 2002.

Johnson et al., "Bone marrow may be source of new egg-cell generation in adult mammals," [online] 2005, [Jul. 27, 2005]. Retrieved from the Internet: <URL: world wide web at eurekalert.org/pub_releases/2005-07/mgh-bmm071505.php>, 2 pages.

Reinberg, "Banking on Stem Cells," [online]. The Scientist, 2005, [retrieved on Jul. 28, 2005]. Retrieved from the Internet: <URL: world wide web at the-scientist.com/2005/7/18/42/1>, 5 pages.

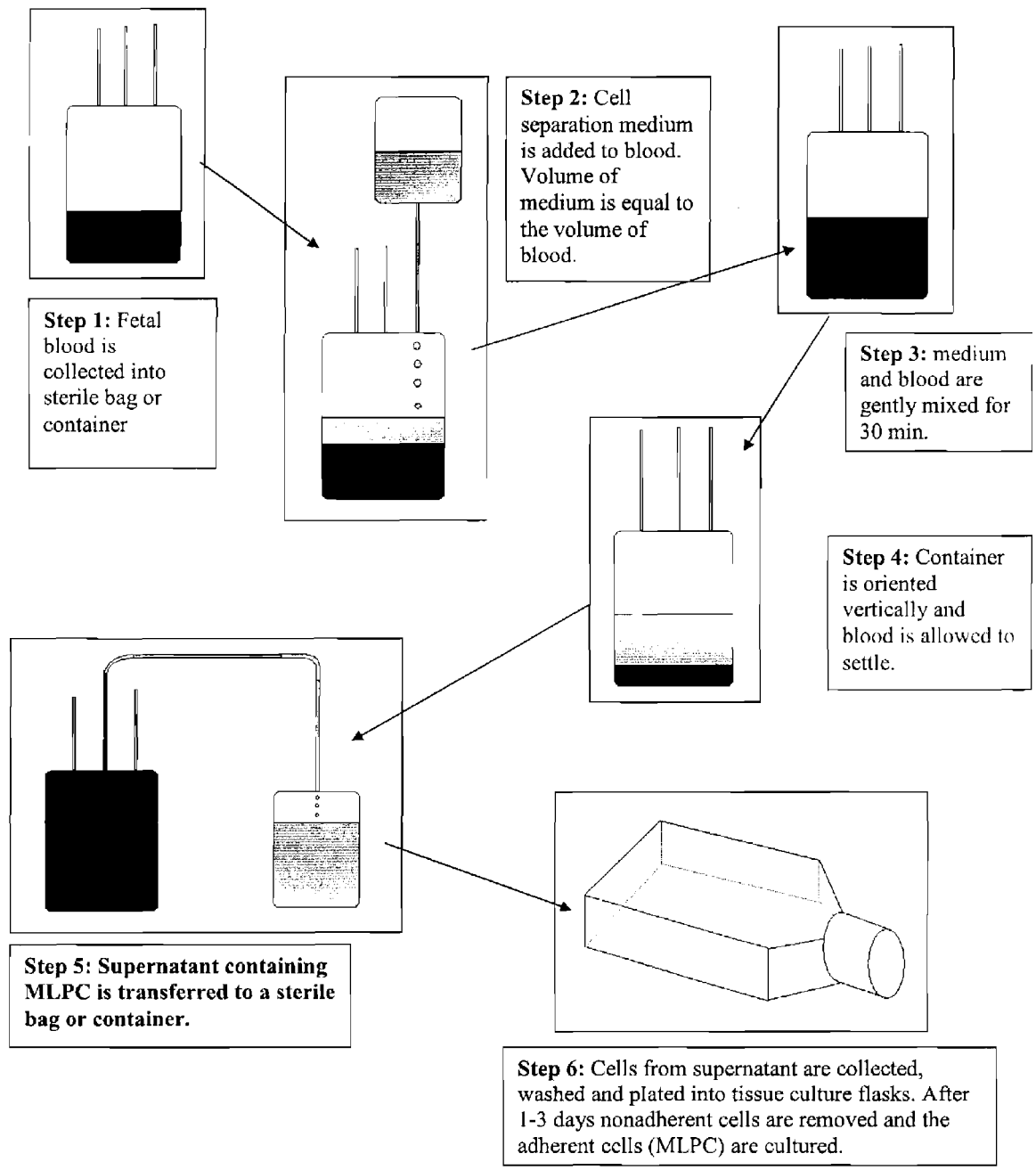

| Name | Description | um102605 (induced) | C3 (induced) | um040505 (induced) | um102605 (control) | C3 (control) | um040505 (control) |
|---|---|---|---|---|---|---|---|
| 214825_at | (clone CTG-A4) mRNA sequence. | 103.4114555 | 80.8815952 | 90.08050871 | 224.2211726 | 163.0095277 | 279.0424355 |
| 205301_s_at | 8-oxoguanine DNA glycosylase | 49.60120185 | 76.61261934 | 71.67150839 | 115.7085251 | 129.8530699 | 133.6908102 |
| 202952_s_at | a disintegrin and metalloproteinase domain 12 (meltrin alpha) | 397.8729057 | 294.1429339 | 394.6742426 | 2745.061258 | 1756.961425 | 5352.293386 |
| 226777_at | a disintegrin and metalloproteinase domain 12 (meltrin alpha) | 367.2367785 | 312.0670115 | 422.7637397 | 1713.321095 | 1439.544254 | 4887.677416 |
| 205745_x_at | a disintegrin and metalloproteinase domain 17 (tumor necrosis factor, alpha, converting enzyme) | 774.3853118 | 692.9246141 | 697.750491 | 375.1735309 | 491.9800503 | 464.4180968 |
| 244463_at | a disintegrin and metalloproteinase domain 23 | 28.37124843 | 28.45474699 | 36.70312426 | 94.79157793 | | 81.00394615 |
| 236006_s_at | A kinase (PRKA) anchor protein 10 | 165.4864144 | 122.3273571 | 135.2195737 | 52.48527559 | 73.90338956 | 56.76210311 |
| 213396_s_at | A kinase (PRKA) anchor protein 10 | 340.1740108 | 295.1080882 | 340.1616832 | 187.037642 | 195.61395 | 194.2354537 |
| 44120_at | aarF domain containing kinase 2 | 340.4623758 | 274.4786305 | 317.6783068 | 208.9051501 | 189.6581129 | 153.6896021 |
| 221893_s_at | aarF domain containing kinase 2 | 169.0712244 | 178.3327964 | 180.6373159 | | 83.20124106 | 105.2882224 |
| 221569_at | Abelson helper integration site | 300.2362956 | 278.0452236 | 205.1143012 | 957.0579515 | 650.1309507 | 1094.171425 |
| 234312_s_at | acetyl-Coenzyme A synthetase 2 (ADP forming) | 184.7616507 | 180.1763099 | 136.3626029 | 85.02189095 | 87.51071357 | 91.15969145 |
| 218075_at | achalasia, adrenocortical insufficiency, alacrimia (Allgrove, triple-A) | 204.2534627 | 253.7011834 | 210.7208853 | 106.9194501 | 132.7421681 | 143.1022129 |
| 236565_s_at | Acheron | 691.8723901 | 476.578368 | 600.8661354 | 1494.797859 | 1144.57536 | 1985.437459 |
| 202767_at | acid phosphatase 2, lysosomal | 841.1703028 | 728.109001 | 748.6765993 | 449.8505106 | 438.9708802 | 421.4785484 |

FIG 5, Page 1

| | | | | | | | |
|---|---|---|---|---|---|---|---|
| 200965_s_at | actin binding LIM protein 1 | 207.8330781 | 241.7502154 | 135.5576655 | 726.8491004 | 493.1530107 | 961.7709469 |
| 213513_x_at | actin related protein 2/3 complex, subunit 2, 34kDa | 2731.988615 | 3102.793569 | 2830.017293 | 4280.111717 | 3801.872318 | 4848.411121 |
| 211160_x_at | actinin, alpha 1 | 787.1331545 | 1101.311174 | 853.4395645 | 2602.499925 | 1647.094856 | 2392.014111 |
| 239825_at | activating transcription factor 6 [BLAST] | 162.3253201 | | 158.3972934 | 19.50668536 | 17.81372308 | 38.54229796 |
| 207275_s_at | acyl-CoA synthetase long-chain family member 1 | 606.6712933 | 531.4101603 | 477.8863943 | 307.5563121 | 230.7545869 | 225.5339855 |
| 211779_x_at | adaptor-related protein complex 2, alpha 2 subunit | 652.0915928 | 708.7685408 | 714.3261189 | 513.657471 | 517.1749117 | 578.7746965 |
| 200613_at | adaptor-related protein complex 2, mu 1 subunit | 2835.508157 | 3225.108913 | 3311.842286 | 4191.742556 | 4149.767908 | 4767.065696 |
| 202398_at | adaptor-related protein complex 3, sigma 2 subunit | 151.5906038 | 103.9741334 | 117.9377403 | 71.77188411 | 60.61325783 | 60.46170867 |
| 203586_s_at | ADP-ribosylation factor 4-like | 296.5684074 | 259.2701033 | 280.7439561 | 174.457586 | 156.4934691 | 205.8560314 |
| 202956_at | ADP-ribosylation factor guanine nucleotide-exchange factor 1 (brefeldin A-inhibited) | 679.5737602 | 827.2360283 | 663.4871453 | 405.8158273 | 484.8972791 | 489.2989311 |
| 215931_s_at | ADP-ribosylation factor guanine nucleotide-exchange factor 2 (brefeldin A-inhibited) | 107.5341812 | 107.2915083 | 100.0511841 | 68.9153653 | 78.90632089 | 77.30799619 |
| 222442_s_at | ADP-ribosylation factor-like 10C | 1474.652116 | 1297.06595 | 1315.695001 | 937.6065299 | 928.0193976 | 879.7298972 |
| 217852_s_at | ADP-ribosylation factor-like 10C | 3480.635493 | 3572.543673 | 3766.659974 | 2350.550697 | 2884.627819 | 2736.7581 |
| 211935_at | ADP-ribosylation factor-like 6 interacting protein | 2079.105974 | 1641.655565 | 1894.419193 | 1157.686842 | 1247.054391 | 1229.46875 |
| 202206_at | ADP-ribosylation factor-like 7 | 131.9667191 | 204.4641406 | 282.2193089 | 766.2226677 | 907.5802171 | 811.7547366 |
| 202207_at | ADP-ribosylation factor-like 7 | 191.4791379 | 399.917066 | 433.9438193 | 1202.4224 | 1558.905742 | 1424.930743 |
| 214953_s_at | amyloid beta (A4) precursor protein (protease nexin-II, Alzheimer disease) | 895.400632 | 1032.515702 | 1168.390717 | 2324.720675 | 3140.272616 | 3677.388294 |

FIG 5, Page 2

| | | | | | | | |
|---|---|---|---|---|---|---|---|
| 202629_at | amyloid beta precursor protein (cytoplasmic tail) binding protein 2 | 1223.859386 | 980.817345 | 1066.461767 | 632.7579883 | 667.5628206 | 744.2348642 |
| 230972_at | ankyrin repeat domain 9 | 337.6276834 | 320.6601782 | 296.0824803 | | 203.2934569 | 200.1916027 |
| 239678_at | AP1 gamma subunit binding protein 1 | 18.3439112 | 16.94552013 | 21.72867014 | 36.32229658 | 34.73790783 | 32.81207428 |
| 202492_at | APG9 autophagy 9-like 1 (S. cerevisiae) | 563.6586368 | 434.4759311 | 465.5209054 | 226.0864642 | 297.2757582 | 248.5094804 |
| 209584_x_at | apolipoprotein B mRNA editing enzyme, catalytic polypeptide-like 3C | 686.6587634 | 623.706802 | 508.7037802 | 211.2481571 | 284.7286054 | 176.5631981 |
| 208270_s_at | arginyl aminopeptidase (aminopeptidase B) | 1696.223538 | 1231.312735 | 1669.589236 | 796.9723521 | 791.6213886 | 786.2606108 |
| 218658_s_at | ARP8 actin-related protein 8 homolog (yeast) | 155.7805931 | 148.7211106 | 150.5910451 | 209.5448508 | 198.4484267 | 208.8457887 |
| 223223_at | ARV1 homolog (yeast) | 788.8709914 | 638.573702 | 659.6936184 | 481.3564643 | 433.7272276 | 457.2515377 |
| 225280_x_at | arylsulfatase D | 117.1761726 | 127.3057851 | 104.1806353 | 63.23372052 | 83.52994837 | 73.56687712 |
| 207335_x_at | ATP synthase, H+ transporting, mitochondrial F0 complex, subunit e | 2412.641347 | 2379.934949 | 2734.162405 | 1770.018824 | 1911.751594 | 1693.550063 |
| 209492_x_at | ATP synthase, H+ transporting, mitochondrial F0 complex, subunit e | 4313.578204 | 4622.315666 | 5097.865617 | 3470.512816 | 3564.321732 | 3611.275561 |
| 201089_at | ATPase, H+ transporting, lysosomal 56/58kDa, V1 subunit B, isoform 2 | 2207.171658 | 1817.601157 | 2316.07487 | 880.2972277 | 1222.422868 | 952.8845308 |
| 201172_x_at | ATPase, H+ transporting, lysosomal 9kDa, V0 subunit e | 6487.921933 | 6885.726238 | 6603.095333 | 5184.292166 | 5269.072564 | 4627.899797 |
| 218048_at | B lymphoma Mo-MLV insertion region (mouse) | 1667.172368 | 1546.165137 | 1676.503505 | 1074.293757 | 1285.833624 | 1223.258445 |
| 209364_at | BCL2-antagonist of cell death | 461.3536152 | 392.3011113 | 449.3674894 | 292.4626883 | 332.1424445 | 332.5974588 |
| 211703_s_at | Beta-amyloid binding protein precursor | 2096.343039 | 1934.925081 | 1645.209415 | 1086.330746 | 941.8940184 | 939.8975086 |
| 213882_at | Beta-amyloid binding protein precursor | 335.9797646 | 295.2281455 | 334.3786318 | 97.21460178 | 113.9981492 | 119.0608225 |

FIG 5, Page 3

| Probe ID | Gene | | | | | | |
|---|---|---|---|---|---|---|---|
| 213883_s_at | Beta-amyloid binding protein precursor | 3868.698881 | 3550.71019 | 2864.716377 | 2123.194252 | 2243.541169 | 2000.146113 |
| 1556051_a_at | Bicaudal D homolog 1 (Drosophila) | 116.2885298 | 108.1074344 | 115.7999847 | 158.2020939 | 161.6340417 | 188.6847241 |
| 201262_s_at | biglycan | 98.42862113 | 202.0726182 | 113.3246329 | 690.7427102 | 387.6419306 | 451.1557356 |
| 205550_s_at | brain and reproductive organ-expressed (TNFRSF1A modulator) | 783.7881711 | 718.2341126 | 808.1798669 | 592.1262789 | 593.8938681 | 550.7734939 |
| 203576_at | branched chain aminotransferase 2, mitochondrial | 506.4661668 | 487.275146 | 414.4013567 | 303.3407086 | 311.8923631 | 288.5923736 |
| 219947_at | C-type (calcium dependent, carbohydrate-recognition domain) lectin, superfamily member 6 | 116.5028221 | 65.62630788 | 119.0451543 | 16.68270874 | 31.19793676 | 31.25486831 |
| 203440_at | cadherin 2, type 1, N-cadherin (neuronal) | 793.9947241 | 1116.135152 | 891.5632471 | 3590.410444 | 1834.65498 | 2723.763961 |
| 225915_at | calcium binding protein 39-like | 532.6009338 | 445.5661337 | 496.5968122 | 241.9636846 | 278.2465564 | 202.8401164 |
| 221972_s_at | Calcium binding protein Cab45 precursor | 1752.042152 | 1232.45877 | 2022.699611 | 776.8091992 | 812.2042549 | 855.8700788 |
| 225693_s_at | calmodulin binding transcription activator 1 | 1505.440234 | 1765.759171 | 1786.91162 | 1072.15463 | 1240.7990039 | 1034.521479 |
| 204312_x_at | cAMP responsive element binding protein 1 | 183.6056937 | 233.947944 | 193.286493 | 335.9176098 | 329.7856311 | 370.5534051 |
| 237289_at | cAMP responsive element binding protein 1 | 180.7212305 | 255.5816449 | 172.56377 | 423.9871386 | 357.6001676 | 441.7969349 |
| 214513_s_at | cAMP responsive element binding protein 1 | 154.9574286 | 183.298388 | 150.8151071 | 275.1406415 | 266.7479454 | 353.2722473 |
| 205832_at | carboxypeptidase A4 | 33.36694492 | 30.84366679 | 31.72064061 | 305.9915454 | 146.6868213 | 124.2486374 |
| 209833_at | CASP2 and RIPK1 domain containing adaptor with death domain | 324.290299 | 337.4572344 | 251.2330554 | 194.5255666 | 170.1798131 | 172.064531 |
| 208818_s_at | catechol-O-methyltransferase | 2619.73048 | 3107.063461 | 3287.852963 | 1774.048491 | 1936.451736 | 2170.218933 |
| 238462_at | Cbl-interacting protein Sts-1 | 201.9370911 | 199.3200574 | 197.579477 | 1424.549617 | 608.9168068 | 672.4409667 |

FIG 5, Page 4

| | | | | | | |
|---|---|---|---|---|---|---|
| 213595_s_at | CDC42 binding protein kinase alpha (DMPK-like) | 42.35588362 | 49.90447669 | 43.06729865 | 84.55177777 | 73.57778762 | 70.98559159 |
| 209055_s_at | CDC5 cell division cycle 5-like (S. pombe) [BLAST] | 813.867814 | 644.9341116 | 643.8912039 | 418.8030336 | 406.7340929 | 460.9793432 |
| 1569005_at | cDNA clone IMAGE:4654330, partial cds | | 15.36677598 | 18.74060264 | 32.65312151 | 28.94327409 | 28.66750895 |
| 231862_at | cDNA clone IMAGE:4842353, partial cds | 278.9729879 | 306.9506405 | 288.0579729 | 554.2614406 | 701.6290237 | 586.7332984 |
| 239847_at | cDNA clone IMAGE:6186815, partial cds | 145.8939686 | 95.52264742 | 104.3187797 | 47.9851263 | 44.17345683 | 54.97939533 |
| 214744_s_at | cDNA FLJ11898 fis, clone HEMBA1007322 | 67.75343427 | 59.84642013 | 86.2641543 | 131.3223555 | 167.4816726 | 140.8137704 |
| 232667_at | cDNA FLJ13690 fis, clone PLACE2000097 | 35.81457149 | 37.85896246 | | 114.4291555 | 75.73175458 | 92.64356353 |
| 236629_at | cDNA FLJ13849 fis, clone THYRO1000865 | 90.03803748 | 81.63148262 | 105.4336169 | | 51.06884427 | 52.62970414 |
| 1558896_at | cDNA FLJ13849 fis, clone THYRO1000865 | 70.9968302 | 79.12247371 | 78.74116767 | 39.61481925 | 51.86718732 | 50.76243877 |
| 233354_at | cDNA FLJ14188 fis, clone NT2RP2005980 | 293.9163638 | 238.8668711 | 309.231691 | 172.6385008 | 182.7961576 | 169.816091 |
| 238164_at | cDNA FLJ34168 fis, clone FCBBF3015131 | 40.0253295 | 50.66700192 | 39.56426461 | 99.6804649 | 72.94635806 | 104.2299267 |
| 236985_at | cDNA FLJ37855 fis, clone BRSSN2014636 | 48.16733027 | 58.26241145 | 54.93157154 | 73.92728606 | 90.67319268 | 77.45219237 |
| 238495_at | cDNA FLJ41444 fis, clone BRSTN2001801 | 89.64476948 | 67.701052 | 65.02809904 | 43.58871965 | 39.5209161 | 31.89704738 |
| 212812_at | cDNA: FLJ22642 fis, clone HSI06970 | 999.8794634 | 811.6908718 | 906.2275279 | 1710.541552 | 1578.486964 | 1632.37438 |
| 201253_s_at | CDP-diacylglycerol--inositol 3-phosphatidyltransferase (phosphatidylinositol synthase) | 5906.289274 | 5399.835885 | 5814.515572 | 3182.499133 | 3814.238056 | 2949.728982 |
| 219398_at | Cell death-inducing CIDE-like effector pseudogene | 290.4900567 | 247.9363722 | 162.6847113 | 88.86202319 | 97.16427872 | 75.95735481 |

FIG 5, Page 5

| | | | | | | | |
|---|---|---|---|---|---|---|---|
| 207428_x_at | Cell division cycle 2-like 1 (PITSLRE proteins) | 334.1540505 | 259.2209033 | 301.2454315 | 122.6580106 | 189.2057495 | 140.7735561 |
| 212401_s_at | Cell division cycle 2-like 1 (PITSLRE proteins) | 962.4412068 | 825.0276561 | 1047.823709 | 500.1800855 | 554.8447765 | 516.0021417 |
| 210859_x_at | ceroid-lipofuscinosis, neuronal 3, juvenile (Batten, Spielmeyer-Vogt disease) | 360.4765309 | 366.0247306 | 506.6594051 | 167.7035149 | 163.6796037 | 149.7605929 |
| 219345_at | CGI-143 protein | 217.2535038 | 193.8914025 | 231.9858212 | 94.29275541 | 103.8782923 | 106.493216 |
| 55093_at | Chondroitin sulfate glucuronyltransferase | 468.4767817 | 491.6868948 | 451.6331415 | 582.5749616 | 583.8422425 | 627.3280875 |
| 1556988_s_at | chromodomain helicase DNA binding protein 1-like | 202.7655413 | 218.869551 | 188.2534426 | 387.061407 | 327.0282936 | 390.7867676 |
| 212539_at | chromodomain helicase DNA binding protein 1-like | 409.7480699 | 417.1830065 | 309.355724 | 675.6160897 | 655.6359737 | 680.0904859 |
| 1554015_a_at | Chromodomain helicase DNA binding protein 2 | 459.3545051 | 318.4900676 | 428.4685675 | 88.99415471 | 133.9249729 | 100.2801585 |
| 1554014_at | Chromodomain helicase DNA binding protein 2 | 510.0109624 | 450.9436694 | 510.0126648 | 71.86606047 | 149.3214864 | 148.3393655 |
| 202808_at | chromosome 10 open reading frame 26 | 1597.114231 | 1983.771912 | 1763.963301 | 608.0515859 | 990.4765657 | 860.9813584 |
| 212121_at | chromosome 10 open reading frame 61 | 1230.153688 | 1201.390223 | 1262.32236 | 730.9733783 | 631.3408783 | 747.4680705 |
| 55662_at | chromosome 10 open reading frame 76 | 167.7928621 | 153.1291176 | 173.2476743 | 90.6181263 | 107.8251569 | 113.0256608 |
| 224651_at | chromosome 10 open reading frame 9 | 350.6345626 | 399.343104 | 375.6029496 | 629.5194682 | 689.8210846 | 823.5843411 |
| 224652_at | chromosome 10 open reading frame 9 | 317.3426513 | 265.9422375 | 339.5567227 | 508.8401222 | 521.5449197 | 455.5946501 |
| 222507_s_at | chromosome 11 open reading frame 15 | 1271.065928 | 1311.363241 | 1261.241169 | 886.9950598 | 686.8431281 | 802.562669 |
| 222626_at | chromosome 13 open reading frame 10 | 158.5093435 | | 161.1217026 | 86.36387947 | 86.65168132 | 78.88867652 |
| 229673_at | chromosome 14 open reading frame 118 | 159.2902206 | 180.3606054 | 151.1302045 | 103.1979156 | 118.5188027 | 112.6663235 |
| 218572_at | chromosome 14 open reading frame 123 | 626.6117733 | 650.8657713 | 573.8633163 | 464.5332661 | 458.9960809 | 455.2589139 |

FIG 5, Page 6

| | | | | | | |
|---|---|---|---|---|---|---|
| 224469_s_at | chromosome 14 open reading frame 151 | 152.7512072 | 156.752472 | 143.8405188 | 74.25740889 | 93.55865108 | 68.96535563 |
| 210532_s_at | chromosome 14 open reading frame 2 | 5533.860209 | 5253.012132 | 5500.926723 | 4098.782288 | 4546.194133 | 4155.003058 |
| 225643_at | chromosome 14 open reading frame 32 | 1168.59966 | 1128.155623 | 1104.936435 | 921.7011044 | 814.5965708 | 736.2341413 |
| 227319_at | chromosome 16 open reading frame 44 | 796.5050572 | 722.9131905 | 556.9850369 | 303.760177 | 380.4668676 | 329.8419328 |
| 238568_s_at | chromosome 18 open reading frame 8 | 90.65153385 | | 94.23940027 | | 34.80967226 | 34.88237501 |
| 226378_s_at | chromosome 19 open reading frame 25 | 428.7234175 | 369.296247 | 570.4200853 | 229.8629613 | 173.176726 | 202.9924939 |
| 215954_s_at | chromosome 19 open reading frame 29 | 229.5435688 | 169.5610507 | 228.5829286 | 95.47028072 | 100.2701173 | 121.8356907 |
| 219496_at | chromosome 2 open reading frame 26 | 143.0197388 | 180.7071846 | 171.0435466 | 262.6260515 | 236.9304793 | 237.5924322 |
| 224693_at | chromosome 20 open reading frame 108 | 470.4853045 | 545.2715003 | 475.3251426 | 325.1729098 | 379.9934728 | 297.3337405 |
| 241741_at | chromosome 20 open reading frame 155 [BLAST] | 52.52344301 | 41.92115077 | 49.5481322 | 73.10598017 | 72.216794 | 86.02537371 |
| 224972_at | chromosome 20 open reading frame 52 | 1563.390085 | 1374.755019 | 1711.338627 | 1050.533264 | 1077.003969 | 1113.438489 |
| 222907_x_at | chromosome 21 open reading frame 4 | 919.6412693 | 877.7617674 | 1472.402287 | 499.6106227 | 361.6036441 | 390.318027 |
| 219600_s_at | chromosome 21 open reading frame 4 | 2714.76136 | 2312.22265 | 4704.263205 | 954.6168017 | 733.2008966 | 776.0320945 |
| 205248_at | chromosome 21 open reading frame 5 | 72.93651499 | 77.11124936 | 59.92792016 | 120.3646534 | 104.8540906 | 114.5758631 |
| 223004_s_at | chromosome 3 open reading frame 1 | 2165.717909 | 1853.184125 | 1983.326426 | 1263.095465 | 1303.938811 | 1333.173232 |
| 203600_s_at | chromosome 4 open reading frame 8 | 432.9585494 | 383.049957 | 423.3315951 | 274.4265446 | 324.2620022 | 298.9076773 |
| 218518_at | chromosome 5 open reading frame 5 | 375.4131501 | 515.4146654 | 324.1434303 | 1355.705336 | 1342.577194 | 1077.369682 |
| 225210_s_at | chromosome 6 open reading frame 119 | 1290.147492 | 1419.445855 | 1399.751537 | 967.4662292 | 1048.747953 | 997.0119391 |

FIG 5, Page 7

| | | | | | | |
|---|---|---|---|---|---|---|
| 218191_s_at | chromosome 6 open reading frame 209 | 2569.03948 | 2611.972061 | 2735.787361 | 1274.575185 | 1718.253725 | 1689.700021 |
| 225083_at | chromosome 6 open reading frame 51 | 2197.738664 | 2461.642806 | 2406.916672 | 3572.809432 | 2985.56129 | 3525.706742 |
| 225576_at | chromosome 6 open reading frame 72 | 2628.771405 | 2459.863964 | 2306.154453 | 1367.400004 | 1578.721818 | 1157.799461 |
| 224988_at | chromosome 6 open reading frame 89 | 629.6587663 | 591.6261699 | 699.2229683 | 418.8072273 | 424.3524199 | 432.9587558 |
| 59437_at | chromosome 9 open reading frame 116 | 35.56600943 | 42.53975996 | 43.96225365 | 64.74904006 | 69.75239277 | 62.51601142 |
| 225403_at | chromosome 9 open reading frame 23 | 1150.391139 | 595.0688542 | 943.7831549 | 224.5706355 | 298.5141254 | 288.6682076 |
| 223947_s_at | cofactor required for Sp1 transcriptional activation, subunit 3, 130kDa | 337.6099746 | 339.1007576 | 331.6483567 | 293.2649676 | 303.6354918 | 296.5319247 |
| 225010_at | coiled-coil domain containing 6 | 2484.485875 | 2033.767501 | 2193.74118 | 1083.612565 | 1027.556964 | 1248.566292 |
| 204716_at | coiled-coil domain containing 6 | 706.2625613 | 642.6691525 | 562.5730328 | 406.1604179 | 312.970224 | 339.9106876 |
| 211980_at | collagen, type IV, alpha 1 | 1024.639379 | 1035.378199 | 847.9758961 | 6648.737045 | 2931.859782 | 9046.585818 |
| 209132_s_at | COMM domain containing 4 | 714.4255861 | 697.0488188 | 750.0387088 | 533.3005555 | 552.9829491 | 436.6735814 |
| 223819_x_at | COMM domain containing 5 | 624.2155747 | 448.580504 | 667.6519558 | 320.9635276 | 305.2831073 | 326.0841993 |
| 231055_at | Consensus includes gb:BF432941 /FEA=EST /DB_XREF=gi:11445104 /DB_XREF=est:7n28g07.x1 /CLONE=IMAGE:3566028 /UG=Hs.263462 ESTs | 178.0428056 | 86.32645359 | 103.6036981 | 38.09378428 | 32.80463544 | 32.40704741 |
| 202142_at | COP9 constitutive photomorphogenic homolog subunit 8 (Arabidopsis) | 2458.034835 | 2216.193856 | 2382.663536 | 1457.719331 | 1492.38208 | 1714.572341 |
| 203551_s_at | COX11 homolog, cytochrome c oxidase assembly protein (yeast) | 392.3632214 | 497.9602564 | 464.045543 | 294.7088587 | 232.7069618 | 294.0421054 |

FIG 5, Page 8

| | | | | | | | |
|---|---|---|---|---|---|---|---|
| 202343_x_at | cytochrome c oxidase subunit Vb | 3385.595197 | 3046.830843 | 3912.182127 | 2187.983926 | 2120.816402 | 2366.654776 |
| 211025_x_at | cytochrome c oxidase subunit Vb | 2988.290205 | 2741.190815 | 3392.04593 | 1750.278594 | 1844.995653 | 1912.965311 |
| 213735_s_at | cytochrome c oxidase subunit Vb | 5456.999154 | 4881.239809 | 4883.991756 | 3810.529568 | 3398.622394 | 3228.075255 |
| 213736_at | cytochrome c oxidase subunit Vb | | 129.2020217 | 131.910286 | 81.61638115 | 79.34266142 | 85.36226851 |
| 226402_at | cytochrome P450, family 2, subfamily U, polypeptide 1 | 1086.570608 | 1117.16706 | 921.9516542 | 433.1664952 | 548.3686107 | 435.3351025 |
| 220999_s_at | cytoplasmic FMR1 interacting protein 2 | 107.9315357 | | 116.3391118 | | 45.70995783 | 49.95116308 |
| 200794_x_at | DAZ associated protein 2 | 4773.407353 | 3774.095905 | 4571.924688 | 2331.002223 | 2801.836133 | 2398.914416 |
| 223140_s_at | DEAH (Asp-Glu-Ala-His) box polypeptide 36 | 949.5964833 | 633.5157653 | 1026.46098 | 417.0638654 | 368.630859 | 395.2788122 |
| 218325_s_at | death associated transcription factor 1 | | 392.9616276 | 406.7307958 | | 223.5760032 | 245.5331079 |
| 203891_s_at | death-associated protein kinase 3 | 61.64603663 | 84.92096178 | 66.70498666 | 160.3407923 | 127.7704105 | 151.6627604 |
| 218021_at | dehydrogenase/reductase (SDR family) member 4 | 693.6651328 | 614.4246153 | 584.9747476 | 442.9247989 | 312.4399911 | 317.295594 |
| 210788_s_at | dehydrogenase/reductase (SDR family) member 7 | 1767.756634 | 1653.452309 | 1706.743216 | 1121.717629 | 907.0251456 | 845.5972338 |
| 205677_s_at | deleted in lymphocytic leukemia, 1 | 134.9765823 | 96.73863926 | 147.5757161 | 221.5157342 | 290.7913476 | 322.6263943 |
| 208763_s_at | delta sleep inducing peptide, immunoreactor | 1738.974738 | 3787.223583 | 4453.278287 | 576.2019386 | 473.6210565 | 699.9855716 |
| 207001_x_at | delta sleep inducing peptide, immunoreactor | 248.9315748 | 802.7153775 | 744.0382873 | 61.82192292 | 63.98245553 | 57.47590706 |
| 203816_at | deoxyguanosine kinase | 184.0726655 | 237.4610488 | 248.9660001 | 422.530968 | 343.8613663 | 401.997414 |
| 217973_at | dicarbonyl/L-xylulose reductase | 810.0317623 | 1045.704379 | 617.9710857 | 338.987751 | 290.0985961 | 329.2564245 |
| 214198_s_at | DiGeorge syndrome critical region gene 2 | 802.4509308 | 830.781092 | 632.5881414 | 301.3689916 | 345.9858495 | 347.3356936 |
| 238818_at | DKFZP434I116 protein | 83.87619085 | 78.68528045 | 93.02713953 | 158.7984857 | 118.6396351 | 158.2969462 |
| 228171_s_at | DKFZP434I216 protein | 162.930108 | 178.8457026 | 334.8446927 | 584.7714374 | 648.0297189 | 781.0612651 |
| 202514_at | DKFZP586B0319 protein | 424.8707446 | 534.3755359 | 448.4716422 | 1322.841288 | 914.7137228 | 908.3430747 |

FIG 5, Page 9

| | | | | | | | |
|---|---|---|---|---|---|---|---|
| 202515_at | DKFZP586B0319 protein [BLAST] | 807.3713795 | 1147.050398 | 965.376386 | 2320.100555 | 2186.930434 | 1760.058089 |
| 208675_s_at | dolichyl-diphosphooligosaccharide-protein glycosyltransferase | 3865.213894 | 4032.186009 | 4581.085761 | 2965.226021 | 3086.146361 | 3006.567852 |
| 219373_at | dolichyl-phosphate mannosyltransferase polypeptide 3 | 667.5370373 | 485.1873119 | 848.30348 | 209.1003845 | 181.2525871 | 288.1796967 |
| 222447_at | DORA reverse strand protein 1 | 171.796611 | 257.4073003 | 167.4894992 | 360.5746927 | 446.524093 | 407.9805499 |
| 229800_at | doublecortin and CaM kinase-like 1 | 25.30544868 | 134.8542859 | 57.02348669 | 1117.824081 | 691.3147363 | 1469.690484 |
| 203635_at | Down syndrome critical region gene 3 | 919.1761181 | 613.3465151 | 982.7995454 | 383.3816147 | 398.8564926 | 398.2462611 |
| 200932_s_at | dynactin 2 (p50) | 1472.234495 | 1566.746116 | 1525.634797 | 1337.663781 | 1331.743024 | 1327.305263 |
| 213064_at | echinoderm microtubule associated protein like 5 | 738.2893234 | 952.7823029 | 810.3048894 | 1269.132151 | 1378.35796 | 1456.906992 |
| 201341_at | Ectodermal-neural cortex (with BTB-like domain) | 121.4070606 | 114.1931368 | 201.1383994 | 2702.631897 | 858.1704195 | 1112.588266 |
| 203829_at | elongation protein 4 homolog (S. cerevisiae) | 350.6497777 | 284.7482926 | 368.0426519 | 223.15774 | 176.4356934 | 200.9275074 |
| 223306_at | emopamil binding protein-like | 1984.477706 | 2347.238738 | 1728.197888 | 998.3130401 | 1192.759616 | 1114.349936 |
| 223087_at | enoyl Coenzyme A hydratase domain containing 1 [BLAST] | 2803.97458 | 2595.912528 | 2854.288211 | 1954.398874 | 2021.981187 | 2265.868149 |
| 209589_s_at | EPH receptor B2 | 80.1604573 | 83.57943211 | 88.01452601 | | 200.8456068 | 177.7420984 |
| 210651_s_at | EPH receptor B2 | 70.88770139 | 96.13944726 | 78.82351309 | 133.859532 | 177.1895998 | 194.646281 |
| 212336_at | erythrocyte membrane protein band 4.1-like 1 | 47.51689894 | 55.53778599 | 56.0482903 | 79.13375534 | 78.72761447 | 78.3769833 |
| 216396_s_at | etoposide induced 2.4 mRNA | 1281.626457 | 1113.594593 | 965.0601929 | 734.3677983 | 708.9940008 | 603.278841 |
| 227708_at | eukaryotic translation elongation factor 1 alpha 1 | 145.1808399 | 252.9082299 | 271.7681938 | 765.1408603 | 927.1405385 | 1277.659062 |
| 224936_at | eukaryotic translation initiation factor 2, subunit 3 gamma, 52kDa | 688.4307748 | 822.512925 | 841.6862772 | 1332.204132 | 1400.723686 | 1456.37286 |

FIG 5, Page 10

| | | 872.2679915 | 1275.398972 | 1096.240519 | 3239.896863 | 2399.083718 | 2350.815227 |
|---|---|---|---|---|---|---|---|
| 224935_at | eukaryotic translation initiation factor 2, subunit 3 gamma, 52kDa [BLAST] | | | | | | |
| 213648_at | exosome component 7 | 423.8884897 | 501.5394968 | 464.2974213 | 168.6006598 | 169.0667098 | 166.6020801 |
| 212160_at | exportin, tRNA (nuclear export receptor for tRNAs) | 1702.969555 | 1711.064463 | 2011.998937 | 2861.89151 | 3466.983121 | 4571.275075 |
| 209005_at | F-box and leucine-rich repeat protein 5 | 868.6465426 | 1013.223629 | 826.8582249 | 446.5758354 | 542.5076479 | 605.5851397 |
| 226541_at | F-box protein 30 | 1901.622452 | 1279.858464 | 1196.5056 | 576.2862944 | 560.2806423 | 720.223937 |
| 212987_at | F-box protein 9 | 1075.427994 | 1432.229104 | 900.8214384 | 2419.454634 | 2205.243339 | 2040.052612 |
| 210638_s_at | F-box protein 9 | 662.4041283 | 837.6735704 | 704.7090582 | 1530.579468 | 1289.627146 | 1339.240831 |
| 1554105_at | family with sequence similarity 11, member A | 405.0960359 | 317.0465035 | 335.0774075 | 151.8186867 | 189.3383296 | 139.0432959 |
| 219696_at | Family with sequence similarity 31, member B | 151.6635559 | 138.4645687 | 124.6121113 | 209.5750284 | 212.4815684 | 209.8214085 |
| 224217_s_at | Fas (TNFRSF6) associated factor 1 | 594.3933432 | 596.6400676 | 618.5500918 | 397.5907016 | 450.813597 | 457.8825285 |
| 218080_x_at | Fas (TNFRSF6) associated factor 1 | 476.7747527 | 512.0630009 | 448.2708839 | 365.845179 | 334.744118 | 368.788037 |
| 222906_at | Feline leukemia virus subgroup C cellular receptor | 90.2816275 | 85.29789922 | 113.4017164 | 57.13644072 | 49.50604786 | 59.42819471 |
| 201910_at | FERM, RhoGEF (ARHGEF) and pleckstrin domain protein 1 (chondrocyte-derived) | 317.9680702 | 444.6700194 | 426.1707501 | 835.6692164 | 793.8682797 | 1255.931133 |
| 235629_at | fibronectin 1 | 408.143218 | 567.6819516 | 474.5458702 | 907.0216856 | 1094.979379 | 1074.947604 |
| 219249_s_at | FK506 binding protein 10, 65 kDa | 250.0139709 | 258.8132004 | 256.2502482 | 458.7013626 | 445.8449717 | 570.6105154 |
| 40850_at | FK506 binding protein 8, 38kDa | 245.6516207 | 334.1868755 | 252.0159498 | 129.2518108 | 155.3160591 | 136.8985957 |
| 235836_at | FLJ46603 protein | 146.8441436 | 115.4332032 | 102.1363251 | 346.7779938 | 242.7843672 | 263.9996458 |
| 35254_at | FLN29 gene product | 288.4146343 | 309.8191118 | 306.9534214 | 227.664844 | 252.0016499 | 235.0864475 |
| 204131_s_at | forkhead box O3A | 1622.327006 | 1469.551731 | 2415.013563 | 640.9837543 | 612.1474066 | 477.9647894 |
| 204891_at | forkhead box O3A | 2705.467268 | 3536.870656 | 3629.218357 | 1274.410491 | 1608.151454 | 1083.179135 |
| 204132_s_at | forkhead box O3A | 645.5959449 | 721.2243545 | 861.7695604 | 286.9419192 | 326.2713063 | 220.189455 |
| 210655_s_at | forkhead box O3A | 378.6152722 | 352.0973902 | 440.8922129 | 174.8317497 | 177.1053827 | 129.3325741 |

FIG 5, Page 11

| Probe | Description | | | | | |
|---|---|---|---|---|---|---|
| 1570156_s_at | formin (limb deformity) | 40.09510982 | | 39.90127512 | 27.62074929 | 27.87119737 |
| 1555471_a_at | Formin 2 | 57.79010294 | 77.42516281 | 69.63541389 | 691.2860579 | 388.8838363 |
| 212232_at | formin binding protein 4 | 754.6269824 | 629.4921526 | 720.4461701 | 362.5521947 | 476.7965782 | 355.0208951 |
| 218210_at | Fructosamine-3-kinase-related protein [BLAST] | 438.2094159 | 520.3366835 | 396.8084818 | 287.8518742 | 294.6041838 | 319.3348121 |
| 241696_at | Full-length cDNA clone CS0DD002YG23 of Neuroblastoma Cot 50-normalized of Homo sapiens (human) | 47.36091849 | 57.37478337 | 55.57460884 | 26.80178155 | 22.56113688 | 32.96781549 |
| 241434_at | Full-length cDNA clone CS0DF034YF04 of Fetal brain of Homo sapiens (human) | 357.0106651 | 274.6016868 | 334.2209788 | 186.0607559 | 181.01636 07 | 141.4285474 |
| 223042_s_at | FUN14 domain containing 2 | 2697.187411 | 2211.625954 | 2610.287463 | 1503.165652 | 1498.52318 | 1801.897189 |
| 215744_at | fusion (involved in t(12;16) in malignant liposarcoma) | 38.18500662 | 31.896 29451 | 37.83206467 | 53.19798295 | 48.10303992 | 52.26485206 |
| 226470_at | gamma-glutamyltransferase-like 3 | 123.2894868 | 138.57577996 | 111.8590258 | 63.83088253 | 77.15295726 | 83.8193768 |
| 209329_x_at | gb:BC000587.1 /DB_XREF=gi:12653618 /FEA=FLmRNA /CNT=102 /TID=Hs.227152.1 /TIER=FL+Stack /STK=36 /UG=Hs.227152 /LL=5648 /UG_GENE=MASP1 /DEF=Homo sapiens, clone MGC:2198, mRNA, complete cds. /PROD=Unk | 1534.645674 | 1375.268399 | 1373.087042 | 1161.014826 | 1145.992525 | 1080.16079 |

FIG 5, Page 12

| | | | | | | | | |
|---|---|---|---|---|---|---|---|---|
| 200070_at | gb:BC001393.1 /DB_XREF=gi:12655084 /FEA=FLmRNA /CNT=168 /TID=Hs.4973.1 /TIER=FL+Stack /STK=71 /UG=Hs.4973 /LL=27013 /UG_GENE=CGI-57 /DEF=Homo sapiens, hypothetical protein, clone MGC:782, mRNA, co ... | 574.7009898 | 432.0241309 | 499.9657159 | 199.8425282 | 237.7801193 | 209.0745621 | |
| 201003_x_at | gb:NM_003349.2 /DB_XREF=gi:12025659 /GEN=UBE2V1 /FEA=FLmRNA /CNT=348 /TID=Hs.75875.0 /TIER=FL /STK=0 /UG=Hs.75875 /LL=7335 /DEF=Homo sapiens ubiquitin-conjugating enzyme E2 variant 1 (UBE2V1), trans | 1125.469094 | 892.25265 | 1070.23816 | 583.0109826 | 621.3486733 | 518.5308117 | |
| 200053_at | gb:NM_004890.1 /DB_XREF=gi:4757715 /GEN=SPAG7 /FEA=FLmRNA /CNT=129 /TID=Hs.90436.0 /TIER=FL /STK=0 /UG=Hs.90436 /LL=9552 /DEF=Homo sapiens sperm associated antigen 7 (SPAG7), mRNA. /PROD=sperm ass ... | 1841.232354 | 1584.69748 | 1803.960477 | 1276.22816 | 1390.619322 | 1266.60325 | |

FIG 5, Page 13

| | | | | | | | | |
|---|---|---|---|---|---|---|---|---|
| 200085_s_at | gb:NM_007108.1 /DB_XREF=gi:6005889 /GEN=TCEB2 /FEA=FLmRNA /CNT=162 /TID=Hs.172772.2 /TIER=FL+Stack /STK=43 /UG=Hs.172772 /LL=6923 /DEF=Homo sapiens transcription elongation factor B (SIII), polype... | 4779.014495 | 4619.495289 | 5306.94056 | 3503.451105 | 3795.014968 | 3933.799045 | |
| 222604_at | general transcription factor IIIC, polypeptide 3, 102kDa | 486.1476918 | 391.9791197 | 462.8610278 | 201.8115665 | 278.224002 | 274.6569492 |
| 204222_s_at | GLI pathogenesis-related 1 (glioma) | 683.6501225 | 980.0651201 | 607.4519926 | 3942.820629 | 2629.825807 | 4778.504069 |
| 204221_x_at | GLI pathogenesis-related 1 (glioma) | 558.7729385 | 503.1815706 | 403.5902241 | 2661.721271 | 1972.901781 | 3476.67771 |
| 227022_at | glucosamine-6-phosphate deaminase 2 | 621.5561054 | 770.7537313 | 775.2372838 | 474.645897 | 497.973791 | 493.2327342 |
| 223079_s_at | glutaminase | 914.4219719 | 887.5230612 | 767.7488473 | 556.2055416 | 483.0485326 | 379.5105328 |
| 200736_s_at | glutathione peroxidase 1 | 8058.909583 | 5362.087365 | 6355.587428 | 2556.062722 | 2847.984084 | 2454.809039 |
| 244680_at | glycine receptor, beta | 135.897445 | 107.8063406 | 93.63514771 | 34.12383647 | 50.89639856 | 26.02824292 |
| 201554_x_at | glycogenin | 2174.872421 | 1726.492083 | 2220.457766 | 1317.51564 | 1439.321182 | 1275.282819 |
| 211275_s_at | glycogenin | 3447.635512 | 2793.646301 | 3347.380633 | 2233.038958 | 2281.585697 | 1929.898597 |
| 208693_s_at | glycyl-tRNA synthetase | 3017.635829 | 2808.804109 | 3418.249086 | 5110.175705 | 4795.582764 | 6054.459901 |
| 236124_at | Golgi phosphoprotein 3 (coat-protein) [BLAST] | 173.4784776 | 187.2275272 | 191.3669577 | 91.17512401 | 113.1815242 | 116.7397179 |
| 204224_s_at | GTP cyclohydrolase 1 (dopa-responsive dystonia) | 358.458385 | 425.0966971 | 262.0593725 | 103.3416555 | 130.2331251 | 102.6856013 |
| 224681_at | guanine nucleotide binding protein (G protein) alpha 12 | 715.3336934 | 605.9392697 | 701.4179463 | 986.8554952 | 995.9708546 | 1225.663983 |
| 208886_at | H1 histone family, member 0 | 1919.741045 | 928.2066 | 1754.027443 | 271.3209612 | 407.3854965 | 361.3833507 |
| 225245_x_at | H2A histone family, member J | 2866.421656 | 2270.422495 | 3544.725015 | 652.4676295 | 697.7957415 | 788.3490499 |
| 224301_x_at | H2A histone family, member J | 2671.557992 | 1732.652768 | 2713.411533 | 794.4533486 | 664.6711278 | 947.1070721 |

FIG 5, Page 14

| | | | | | | |
|---|---|---|---|---|---|---|
| 212525_s_at | H2A histone family, member X | 132.4614925 | | 178.2518608 | 55.44863814 | 52.48595132 | 68.60840248 |
| 211948_x_at | HBxAg transactivated protein 2 | 518.6265082 | 548.0664202 | 649.0561173 | 362.5872907 | 409.7086044 | 386.9003151 |
| 212785_s_at | HDCMA18P protein | 965.1407272 | 834.007225 | 1058.403204 | 545.6299059 | 648.7544307 | 609.2775334 |
| 208814_at | heat shock 70kDa protein 4 | 272.7850338 | 383.1423903 | 307.3116435 | 562.7203245 | 559.91555 | 574.5475486 |
| 200942_s_at | heat shock factor binding protein 1 | 4017.354757 | 3769.03155 | 3996.162748 | 2998.195585 | 2722.112399 | 2286.90214 |
| 202299_s_at | hepatitis B virus x interacting protein | 4388.532735 | 3483.132572 | 3981.809541 | 2494.542913 | 2473.322768 | 2298.384179 |
| 202300_at | hepatitis B virus x interacting protein | 4093.828794 | 3223.574502 | 3052.583711 | 2115.043773 | 2066.661703 | 1721.722156 |
| 209961_s_at | hepatocyte growth factor (hepapoietin A; scatter factor) | 60.46952221 | 54.36373306 | | 165.8817518 | 151.8646631 | |
| 238565_at | HepG2 partial cDNA, clone hmd2d12m5 | 55.45350331 | | 50.40969008 | 153.9060915 | | 139.3545956 |
| 220387_s_at | HERV-H LTR-associating 3 | 428.438535 | 297.3335987 | 423.5080577 | 177.4273467 | 173.0596712 | 164.1397208 |
| 234665_x_at | HERV-H LTR-associating 3 | 454.7262836 | 292.3751224 | 370.4500537 | 183.000148 | 175.0662495 | 155.0131513 |
| 212552_at | hippocalcin-like 1 [BLAST] | 629.813111 | 367.8217683 | 459.2728114 | 1163.491569 | 1384.999011 | 1271.188365 |
| 225222_at | hippocampus abundant transcript 1 | 2048.986609 | 1709.169364 | 1743.765854 | 1128.972521 | 1380.048134 | 1159.606177 |
| 226136_at | HIV-1 rev binding protein 2 | 410.6581968 | 560.9040121 | 356.5370426 | 1888.077618 | 1589.899532 | 3240.69104 |
| 226142_at | HIV-1 rev binding protein 2 | 467.7618189 | 1047.41758 | 448.1080343 | 3318.883559 | 2693.429419 | 4086.74494 |
| 214085_x_at | HIV-1 rev binding protein 2 | 870.6025369 | 1094.67711 | 788.7848548 | 4327.851793 | 3467.515488 | 5617.924322 |
| 207180_s_at | HIV-1 Tat interactive protein 2, 30kDa | 416.9809443 | 377.7015912 | 469.0950782 | 205.857013 | 218.6586264 | 244.415328 |
| 209399_at | holocarboxylase synthetase (biotin-[propionyl-Coenzyme A-carboxylase (ATP-hydrolysing)] ligase) | 40.87810763 | | 48.6116846 | 120.3924929 | 117.7465206 | 176.9197735 |
| 227396_at | Homo sapiens, clone IMAGE:4454331, mRNA | 139.0487327 | 115.5106194 | 108.4068879 | 201.9885171 | 174.2517344 | 211.3256335 |
| 229213_at | Homo sapiens, clone IMAGE:4824541, mRNA | 94.73699187 | 82.56699146 | 85.99424509 | 52.42700772 | 58.2217255 | 45.68275336 |

FIG 5, Page 15

| | | | | | | | |
|---|---|---|---|---|---|---|---|
| 1570185_at | Homo sapiens, clone IMAGE:5766850, mRNA | 146.2518455 | 155.6164422 | 129.4173989 | 94.87469221 | 100.7311784 | 105.1997977 |
| 223993_s_at | HSPC163 protein | 3739.426107 | 3193.428927 | 3589.020536 | 2672.033199 | 2364.982916 | 2429.772063 |
| 203644_s_at | HSV-1 stimulation-related gene 1 | 182.5921335 | 192.9271949 | 178.3779561 | 77.50236238 | 60.02564347 | 65.85501967 |
| 236273_at | Hypothetical gene supported by AB051480; NM_017940 | 73.55814286 | 81.40564179 | 47.22162579 | 173.3947841 | 169.0477657 | 214.5869053 |
| 238021_s_at | Hypothetical gene supported by AF275804 | 1228.887321 | 1718.289776 | 1298.440342 | 2526.896918 | 2800.926451 | 3838.336182 |
| 239466_at | Hypothetical LOC344595 | 54.40231965 | 78.6107259 | 46.40735201 | 129.4094384 | 126.6345948 | 130.6230747 |
| 227862_at | Hypothetical LOC388610 | 2161.646727 | 2747.161613 | 1719.383949 | 720.3486127 | 686.2126289 | 505.6691139 |
| 48117_at | Hypothetical protein BC011981 | 77.21401502 | 92.27793624 | 78.62395905 | 119.3324482 | 152.3479296 | 141.9529064 |
| 214733_s_at | Hypothetical protein DJ167A19.1 | 455.0288626 | 399.9857222 | 457.0241842 | | 231.6909866 | 273.0443946 |
| 221031_s_at | Hypothetical protein DKFZp434F0318 | 174.7305724 | 90.24977639 | 122.8985144 | 981.2369528 | 516.25785 | 405.6026374 |
| 227170_at | Hypothetical protein DKFZp547K054 | 109.7600944 | 69.41511751 | 83.11459973 | 37.73650282 | 37.10144084 | 42.89537574 |
| 213079_at | Hypothetical protein DT1P1A10 | 626.0819408 | 423.3130243 | 554.0397436 | 243.5008724 | 253.6136132 | 267.7477891 |
| 218008_at | Hypothetical protein FLJ10099 | 2120.255214 | 1412.527146 | 1909.02969 | 1065.239965 | 955.7463574 | 919.0371884 |
| 219060_at | Hypothetical protein FLJ10204 | 223.259704 | 302.1861922 | 225.2168494 | 468.8933605 | 381.5076479 | 456.1961622 |
| 218040_at | Hypothetical protein FLJ10330 | 331.8316943 | 310.8383715 | 345.8834127 | 244.569101 | 269.1662678 | 259.3807754 |
| 46947_at | Hypothetical protein FLJ10613 | 56.18106126 | 42.62332294 | 47.79136107 | 88.02325592 | 91.03224455 | 74.33315127 |
| 1555803_a_at | Hypothetical protein FLJ10726 | 154.6583913 | 153.9143112 | 170.7791707 | 215.3283881 | 247.5579857 | 250.0268466 |
| 232057_at | Hypothetical protein FLJ13291 | 349.2757287 | 244.371161 | 423.1761912 | 106.3821167 | 118.2093403 | 138.2045424 |
| 219338_s_at | Hypothetical protein FLJ20156 | 203.3318479 | 163.5433877 | 211.4087834 | 274.3466028 | 302.9744017 | 321.7473202 |

FIG 5, Page 16

| | | | | | | |
|---|---|---|---|---|---|---|
| 225637_at | Hypothetical protein FLJ20186 | 838.1578242 | 562.1563178 | 887.0618887 | 303.8904198 | 291.8106177 | 286.3431165 |
| 223009_at | Hypothetical protein FLJ20625 | 3069.831452 | 3040.476935 | 3038.882559 | 2013.344459 | 2298.108015 | 2286.624085 |
| 235294_at | Hypothetical protein FLJ21168 | 136.0712874 | 111.5142445 | 129.8687982 | 237.3548626 | 180.5292493 | 247.4337157 |
| 219254_at | Hypothetical protein FLJ22222 | | 132.893406 | 125.0649972 | 83.17950285 | 71.63231965 | 85.30729525 |
| 228341_at | Hypothetical protein FLJ31265 | 427.6502721 | 340.2990958 | 285.1385158 | 132.951274 | 165.2729426 | 136.9026431 |
| 221791_s_at | Hypothetical protein HSPC016 | 9426.223698 | 11451.25671 | 10466.13811 | 7167.496479 | 7872.074994 | 7687.577493 |
| 224871_at | Hypothetical protein LOC127262 | 1622.083345 | 1521.089743 | 1646.333198 | 1250.345908 | 1091.385747 | 1157.522349 |
| 227086_at | Hypothetical protein LOC128977 | 174.1290541 | 157.3778403 | 210.0930215 | 81.68961822 | 108.0734686 | 86.85765174 |
| 227840_at | Hypothetical protein LOC130355 | 504.3884525 | 562.3000148 | 537.2375558 | 349.6001475 | 306.5906463 | 371.8839944 |
| 212155_at | Hypothetical protein LOC149603 | 504.9062981 | 667.6408133 | 538.7166923 | 868.3376022 | 830.9391699 | 937.5864113 |
| 244231_at | Hypothetical protein LOC149684 | 68.27864478 | 75.54002781 | 68.16231731 | 236.3326812 | 193.3262207 | 341.1618267 |
| 203447_at | Hypothetical protein LOC253039 | 971.4788184 | 1007.168209 | 1081.204292 | 805.3308488 | 731.8365618 | 763.9702311 |
| 226430_at | Hypothetical protein LOC253981 | 1077.388177 | 1174.687618 | 1051.65796 | 918.525477 | 870.1049315 | 812.8342313 |
| 209158_s_at | Hypothetical protein LOC284356 | 204.2681699 | 205.3257691 | 206.7032203 | 321.3004084 | 372.6794512 | 386.6131732 |
| 218288_s_at | Hypothetical protein MDS025 | 1088.499195 | 1171.743884 | 958.9944214 | 1715.993051 | 1913.277299 | 1890.623596 |
| 225772_s_at | Hypothetical protein MGC14288 | 1267.486553 | 1028.658533 | 1048.497942 | 527.1530184 | 558.9621456 | 405.3155306 |
| 224443_at | Hypothetical protein MGC14801 | 132.4580818 | 102.5613072 | 108.6827071 | 69.82490513 | 79.32299042 | 68.81337331 |
| 229650_s_at | Hypothetical protein MGC2747 | 1120.041509 | 866.5680776 | 1040.72349 | 545.8581285 | 531.1497329 | 520.5515962 |

FIG 5, Page 17

| | | | | | | | |
|---|---|---|---|---|---|---|---|
| 219097_x_at | Hypothetical protein MGC2747 | 1810.197328 | 1767.010796 | 1757.97879 | 877.1408597 | 1009.692708 | 995.4461788 |
| 226175_at | Hypothetical protein MGC29649 | 414.4183508 | 429.2282508 | 424.1663015 | 297.9852223 | 296.7661713 | 286.7721702 |
| 1552310_at | Hypothetical protein MGC29937 | 380.0880683 | 381.4652636 | 371.7630763 | 428.9266703 | 452.1088967 | 468.2067845 |
| 224706_at | Hypothetical protein MGC33867 | 783.7601412 | 569.398291 | 737.2357048 | 333.0276873 | 323.8543707 | 409.6552734 |
| 235486_at | Hypothetical protein MGC34830 | 45.62108312 | 88.19383038 | 59.75018522 | 272.5165631 | 211.961628 | 216.0187603 |
| 231258_at | Hypothetical protein MGC8721 | 79.16870466 | 80.00755647 | 93.53077258 | 52.81974557 | 62.60299771 | 61.70350147 |
| 226802_s_at | Hypothetical protein similar to KIAA0187 gene product | 293.4084782 | 281.2283104 | 269.3831357 | 452.6080296 | 377.1823537 | 411.3282414 |
| 202993_at | IlvB (bacterial acetolactate synthase)-like | 532.1858646 | 486.349875 | 511.128437 | 377.2260609 | 379.3048317 | 383.5273424 |
| 31861_at | immunoglobulin mu binding protein 2 | 262.5560574 | 211.8077524 | 208.986949 | 156.8522141 | 129.370322 | 149.0181893 |
| 200994_at | importin 7 | 1400.374409 | 1430.489348 | 1674.887059 | 2334.491634 | 2043.748602 | 2591.686315 |
| 200993_at | importin 7 | 1823.712977 | 1669.678404 | 1753.562475 | 2674.012647 | 2314.664993 | 2835.09986 |
| 210511_s_at | inhibin, beta A (activin A, activin AB alpha polypeptide) | 197.1064343 | 431.9711908 | 139.8710651 | 4065.966214 | 1611.611257 | 4835.730763 |
| 209171_at | inosine triphosphatase (nucleoside triphosphate pyrophosphatase) | 1094.501216 | 931.9496997 | 1069.966189 | 763.9046618 | 734.0782616 | 756.6739717 |
| 209185_s_at | insulin receptor substrate 2 | 5356.659381 | 5990.283964 | 3368.47457 | 1008.98906 | 1982.892387 | 1315.903305 |
| 209184_s_at | insulin receptor substrate 2 [BLAST] | 1284.299254 | 918.8645416 | 842.5251094 | 159.9313565 | 305.3151345 | 219.4492307 |
| 227372_s_at | Insulin receptor tyrosine kinase substrate | 415.6679409 | 259.1012802 | 401.7983002 | 115.1475546 | 125.1302556 | 92.64846718 |
| 205302_at | insulin-like growth factor binding protein 1 | 388.3751523 | 540.6959846 | 88.43938903 | 4448.681186 | 4589.170916 | 7460.199367 |
| 232912_at | Intimal thickness-related receptor | 23.99973168 | 27.64268704 | 30.18091089 | 76.05484721 | 60.98911234 | 98.68427584 |
| 210878_s_at | jumonji domain containing 1B | 1060.256012 | 645.6809154 | 907.8879673 | 209.9053677 | 330.8899841 | 368.9486247 |

FIG 5, Page 18

| | | | | | | | |
|---|---|---|---|---|---|---|---|
| 1552717_s_at | KARP-1-binding protein | 234.8531754 | 226.9072794 | 174.0251301 | 564.5059091 | 405.7515877 | 409.6011681 |
| 212746_s_at | KARP-1-binding protein | 1008.985211 | 838.1506302 | 751.1664994 | 2250.514267 | 1669.493704 | 1938.418594 |
| 226874_at | kelch-like 8 (Drosophila) [BLAST] | 378.6445204 | 386.6968778 | 352.8395874 | 274.8390532 | 286.3330128 | 286.2446888 |
| 36888_at | KIAA0841 | 147.2414175 | 161.6645655 | 136.872748 | 116.9078383 | 107.0876228 | 111.3450665 |
| 212402_at | KIAA0853 | 1206.150418 | 1045.395772 | 1118.435622 | 693.5715325 | 755.1172358 | 763.0043824 |
| 206468_s_at | KIAA0859 | 369.974303 | 311.0484692 | 353.012756 | 224.0770948 | 163.7569681 | 163.766729 |
| 227479_at | KIAA1244 | 411.4118041 | 335.937953 | 325.7651365 | 234.3032934 | 250.8615994 | 239.8516298 |
| 227895_at | KIAA1838 | 344.2513341 | 308.2936924 | 361.6983184 | 221.5953912 | 231.5676146 | 180.045681 |
| 234994_at | KIAA1913 | 1349.614625 | 1250.430572 | 1192.452529 | 5315.657853 | 3398.833077 | 3598.006234 |
| 201795_at | lamin B receptor | 526.657055 | 604.0131229 | 706.215078 | 345.1955147 | 375.3082643 | 393.8573803 |
| 210396_s_at | LAT1-3TM protein | 939.4736277 | 893.0328577 | 1028.406446 | 1911.939391 | 1484.600911 | 1404.714823 |
| 202729_s_at | latent transforming growth factor beta binding protein 1 | 2069.365604 | 1811.332751 | 2226.982109 | 3743.686569 | 3465.006474 | 4296.937361 |
| 200923_at | lectin, galactoside-binding, soluble, 3 binding protein | 277.7885303 | 467.4688279 | 338.6591307 | 803.3697887 | 771.5627084 | 1127.338778 |
| 211354_s_at | Leptin receptor | 348.8439712 | 401.2398138 | 1087.637416 | 60.25187127 | 57.8923451 | 81.28035863 |
| 211355_x_at | Leptin receptor | 438.0418664 | 481.0817969 | 985.5303212 | 96.38708789 | 86.9181001 | 128.3933661 |
| 211356_x_at | Leptin receptor | 533.0750413 | 520.4907863 | 1293.217863 | 110.7421824 | 109.8894446 | 128.1992533 |
| 205953_at | leucine-rich repeats and immunoglobulin-like domains 2 | 130.0762929 | 112.5092382 | 130.0366649 | 67.23678421 | 88.04481073 | 84.03604415 |
| 232018_at | leukocyte receptor cluster (LRC) member 1 | 43.11164861 | 59.88575704 | 48.80917141 | 81.4080485 | 81.42920726 | 84.09930079 |
| 224673_at | leukocyte receptor cluster (LRC) member 8 | 140.9709779 | 161.3534311 | 142.3644382 | 99.30922511 | 116.1289968 | 101.9913436 |
| 208858_s_at | Likely ortholog of mouse membrane bound C2 domain containing protein | 897.3060455 | 931.8230576 | 1053.054476 | 682.6123076 | 544.547865 | 594.4282059 |
| 219760_at | lin-7 homolog B (C. elegans) | 43.20456452 | 67.28752384 | 52.92529382 | 159.1453634 | 113.5592356 | 182.18277 |
| 227567_at | LOC440460 [BLAST] | 847.8687511 | 784.8016594 | 882.4351307 | 1050.34493 | 996.3375572 | 1042.477244 |
| 201412_at | low density lipoprotein receptor-related protein 10 | 2812.823669 | 2913.774313 | 3246.5158 | 1943.44132 | 2278.315505 | 2217.029913 |
| 203005_at | lymphotoxin beta receptor (TNFR superfamily, member 3) | 997.1788228 | 971.6849809 | 773.9589389 | 280.0006294 | 489.7657855 | 375.7491248 |

FIG 5, Page 19

| | | | | | | | |
|---|---|---|---|---|---|---|---|
| 227476_at | lysophosphatidylglycerol acyltransferase 1 | 208.1294076 | 217.9468265 | 213.4098495 | 409.9180885 | 293.644178 | 350.5807297 |
| 200904_at | major histocompatibility complex, class I, E | 1451.016697 | 1822.947007 | 1450.798074 | 350.6027968 | 707.5225384 | 319.8657641 |
| 207565_s_at | major histocompatibility complex, class I-related | 343.6164885 | 323.643648 | 572.9468098 | 115.5148606 | 161.9653327 | 160.425452 |
| 213333_at | malate dehydrogenase 2, NAD (mitochondrial) | 147.5854274 | 133.3545766 | 161.1423709 | 265.6886094 | 264.0683879 | 374.1527066 |
| 218061_at | male-enhanced antigen | 1410.015037 | 1308.125031 | 1444.201636 | 1837.314645 | 1635.335673 | 1823.740804 |
| 220189_s_at | mannosyl (alpha-1,3-)-glycoprotein beta-1,4-N-acetylglucosaminyltransferase, isoenzyme B | 1138.649435 | 952.9867697 | 1214.771332 | 555.3082331 | 675.4695233 | 616.6358999 |
| 220945_x_at | MANSC domain containing 1 | 1239.998783 | 839.9402233 | 787.7526998 | 327.0671248 | 492.4959591 | 363.1279907 |
| 209467_s_at | MAP kinase interacting serine/threonine kinase 1 | 457.17981 | 364.1150894 | 497.9395991 | 213.3110617 | 247.7263749 | 269.654177 |
| 208795_s_at | MCM7 minichromosome maintenance deficient 7 (S. cerevisiae) | 133.9429189 | 139.8972123 | 138.6061988 | | 296.3730365 | 233.3640138 |
| 228743_at | mediator of RNA polymerase II transcription, subunit 31 homolog (yeast) | 134.2978611 | 130.6053244 | 106.7606027 | 232.8423764 | | 220.6386591 |
| 202593_s_at | Membrane interacting protein of RGS16 | 1411.868572 | 1181.397518 | 1305.870826 | 741.554335 | 819.3160179 | 964.2699333 |
| 222400_s_at | Membrane-type 1 matrix metalloproteinase cytoplasmic tail binding protein-1 | 3302.786867 | 3445.374164 | 3096.600539 | 2087.516088 | 2461.53834 | 1942.370345 |
| 217761_at | Membrane-type 1 matrix metalloproteinase cytoplasmic tail binding protein-1 | 2474.432806 | 2674.693621 | 2457.468785 | 1532.470183 | 1659.95065 | 1750.99232 |
| 200899_s_at | meningioma expressed antigen 5 (hyaluronidase) | 2130.196519 | 2036.028334 | 1663.343427 | 725.7508982 | 923.6563192 | 906.6087405 |
| 200898_s_at | meningioma expressed antigen 5 (hyaluronidase) | 771.1945186 | 812.8621382 | 767.5929083 | 367.8031773 | 354.9223836 | 406.6237526 |

FIG 5, Page 20

| | | | | | | | |
|---|---|---|---|---|---|---|---|
| 204326_x_at | metallothionein 1X | 8372.2156 | 4388.654108 | 4679.929668 | 1321.516683 | 1061.016155 | 690.7262418 |
| 204656_at | mitochondrial carrier triple repeat 1 | 82.33974033 | | 66.73880652 | 243.2295579 | 180.1304373 | 233.2211783 |
| 221692_s_at | mitochondrial ribosomal protein L34 | 1560.934904 | 1028.062745 | 1275.651991 | 549.8545337 | 719.9695006 | 597.4272293 |
| 236910_at | mitochondrial ribosomal protein L39 | 33.82081498 | 31.75926458 | | 23.26957473 | 23.85216526 | 20.89460886 |
| 203152_at | mitochondrial ribosomal protein L40 | 905.9600833 | 1151.001837 | 1087.523325 | 681.232304 | 717.1396939 | 713.5009397 |
| 227131_at | mitogen-activated protein kinase kinase kinase 3 | 343.0245206 | 323.6049147 | 396.5805456 | 181.6598604 | 220.4472623 | 228.6854086 |
| 214949_at | MRNA; cDNA DKFZp586L141 (from clone DKFZp586L141) | 613.3781023 | 567.719579 | 522.2225479 | 809.8344109 | 726.4894303 | 865.7820921 |
| 205145_s_at | myosin, light polypeptide 5, regulatory | 79.11598466 | 77.41825922 | 74.61515207 | 258.3876566 | 256.7964061 | 186.2162595 |
| 205090_s_at | N-acetylglucosamine-1-phosphodiester alpha-N-acetylglucosaminidase | 250.0528383 | 263.3263924 | 241.9730303 | 146.3525125 | 169.67404 | 115.6319136 |
| 215069_at | N-myristoyltransferase 2 | 57.81474367 | 53.09237188 | 42.04586088 | 113.6109057 | 99.09990312 | 86.12736906 |
| 202263_at | NAD(P)H quinone oxidoreductase type 3, polypeptide A2 | 1390.56097 | 1118.338564 | 1374.96874 | 766.4817542 | 773.7434424 | 608.2667607 |
| 209224_s_at | NADH dehydrogenase (ubiquinone) 1 alpha subcomplex, 2, 8kDa | 3186.775379 | 2079.288399 | 2519.115512 | 1425.960497 | 1335.115458 | 1227.826571 |
| 204125_at | NADH dehydrogenase (ubiquinone) 1 alpha subcomplex, assembly factor 1 | 1583.976006 | 1067.205495 | 1545.393409 | 648.9307843 | 612.6601883 | 662.6698189 |
| 203371_s_at | NADH dehydrogenase (ubiquinone) 1 beta subcomplex, 3, 12kDa | 2179.112939 | 1685.958416 | 1936.118428 | 1216.453474 | 1334.589066 | 1264.190905 |
| 203621_at | NADH dehydrogenase (ubiquinone) 1 beta subcomplex, 5, 16kDa | 3134.71022 | 3222.212901 | 3155.315461 | 2809.32784 | 2927.181551 | 2731.989917 |

FIG 5, Page 21

| | | | | | | |
|---|---|---|---|---|---|---|
| 228523_at | nanos homolog 1 (Drosophila) | 46.58379826 | 28.35526905 | 57.32044792 | 170.0951967 | 273.3771221 | 138.8418869 |
| 222018_at | nascent-polypeptide-associated complex alpha polypeptide | 193.3279722 | 182.2734865 | 208.2189448 | | 124.1126822 | 128.3743273 |
| 204310_s_at | natriuretic peptide receptor B/guanylate cyclase B (atrionatriuretic peptide receptor B) | 244.1475349 | 356.0394306 | 259.1017744 | 97.93839563 | 122.0553162 | 134.5447629 |
| 222422_s_at | Nedd4 family interacting protein 1 | 1015.441745 | 676.0869277 | 829.340762 | 453.1820437 | 356.073217 | 398.6560831 |
| 201840_at | neural precursor cell expressed, developmentally down-regulated 8 | 4113.631684 | 4463.533787 | 3747.12988 | 3160.115683 | 3056.00334 | 2845.11738 |
| 212678_at | neurofibromin 1 (neurofibromatosis, von Recklinghausen disease, Watson disease) | 354.2538384 | 322.1122089 | 297.052724 | 211.3202928 | 244.1930588 | 234.2767045 |
| 224771_at | neuron navigator 1 | 462.6864797 | 582.0013231 | 718.8758655 | 1591.034847 | 1706.586966 | 2712.361126 |
| 224773_at | neuron navigator 1 | 396.9271361 | 615.1331573 | 397.5685206 | 1290.532043 | 986.8653772 | 1511.391456 |
| 243357_at | neuronal growth regulator 1 | 453.6970721 | 575.0162209 | 1093.59401 | 173.909658 | 150.5210491 | 123.2921323 |
| 229461_x_at | neuronal growth regulator 1 | 1277.713894 | 1583.778885 | 2524.206564 | 376.7495125 | 217.4264719 | 367.2719777 |
| 1553194_at | neuronal growth regulator 1 | 227.7797285 | 324.6600841 | 579.1473912 | 82.81840301 | 68.910663342 | 75.46776966 |
| 202238_s_at | nicotinamide N-methyltransferase | 7126.831934 | 11671.64593 | 8401.21703 | 2756.198059 | 3239.498302 | 3879.439076 |
| 219680_at | NOD9 protein | 468.6298269 | 387.7395395 | 363.8570026 | 264.2967752 | 265.7195236 | 269.3580888 |
| 212133_at | non imprinted in Prader-Willi/Angelman syndrome 2 | 139.5760481 | 136.1872193 | 170.5026012 | 267.8559492 | 291.742305 | 308.5678332 |
| 208698_s_at | non-POU domain containing, octamer-binding | 1121.30478 | 1170.724643 | 1301.899769 | 1548.650992 | 1575.935182 | 1488.969485 |
| 1560631_at | Nuclear domain 10 protein | 42.80603332 | 37.28643897 | 41.82536045 | | 22.92246127 | 26.51194223 |
| 212808_at | Nuclear factor of activated T cells, cytoplasmic, calcineurin-dependent 2 interacting protein | 129.0652621 | 117.2396626 | 128.2278654 | 61.43077075 | 82.25003482 | 75.17985779 |
| 209062_x_at | nuclear receptor coactivator 3 | 268.0019772 | 298.9863644 | 314.5427794 | 126.2183284 | 180.0930778 | 139.3005827 |

FIG 5, Page 22

| | | | | | | | |
|---|---|---|---|---|---|---|---|
| 221923_s_at | nucleophosmin (nucleolar phosphoprotein B23, numatrin) | 1137.233216 | 1459.157496 | 1321.061794 | 2556.077348 | 2317.893411 | 2715.209293 |
| 1556121_at | nucleosome assembly protein 1-like 1 | 176.4433495 | 156.4786947 | 131.0504309 | 294.7687298 | 256.5456285 | 366.4237586 |
| 201414_s_at | nucleosome assembly protein 1-like 4 | 421.2087232 | 419.2607982 | 406.4394019 | 455.1792509 | 447.6819562 | 452.1250657 |
| 223100_s_at | nudix (nucleoside diphosphate linked moiety X)-type motif 5 | 1873.414854 | 1553.27766 | 1575.37544 | 755.9498115 | | 774.5492787 |
| 226287_at | NY-REN-41 antigen | 102.9984201 | 122.4756641 | 88.67150812 | 168.319271 | 196.6999813 | 222.6091276 |
| 201246_s_at | OTU domain, ubiquitin aldehyde binding 1 | 145.2645602 | 107.122709 | 153.7535931 | 53.50061635 | 57.07813941 | 47.44845368 |
| 214078_at | p21 (CDKN1A)-activated kinase 3 | 35.9643137 | 62.97593362 | 56.05208551 | 259.8062203 | 201.9633803 | 211.4046503 |
| 236277_at | p21 (CDKN1A)-activated kinase 3 | 150.1864522 | 100.6655395 | 129.5595357 | 506.1991361 | 438.468178 | 462.8082813 |
| 209490_s_at | Palmitoyl-protein thioesterase 2 | 112.8817993 | 109.534855 | 75.19839378 | 286.5959618 | 191.9307131 | 280.1757219 |
| 210355_at | parathyroid hormone-like hormone | 27.84036166 | 36.91017904 | 48.72800099 | 208.5846399 | 92.33762164 | 168.5321771 |
| 222171_s_at | PBX/knotted 1 homeobox 2 | 36.547743033 | 55.15116961 | 48.57868769 | 109.2994974 | 116.2194587 | 190.2313471 |
| 207239_s_at | PCTAIRE protein kinase 1 | 118.8910232 | 134.1145169 | 121.5886858 | 186.2605734 | 167.5123422 | 199.9527165 |
| 36829_at | period homolog 1 (Drosophila) | 331.5942765 | 255.8789388 | 233.5899033 | | 97.9534344 | 97.02630878 |
| 242760_x_at | phosphatidylinositol glycan, class B | 288.8476183 | 326.1966373 | 258.6149536 | 120.4567491 | 173.3524566 | 146.0989893 |
| 214151_s_at | phosphatidylinositol glycan, class B | 583.3641511 | 714.5363107 | 579.9178345 | 1144.118091 | 1060.165519 | 1438.421695 |
| 221511_x_at | Phosphatidylinositol glycan, class B | 800.1084005 | 902.4788578 | 817.8526658 | 1498.881928 | 1235.01254 | 1638.447648 |
| 222156_x_at | Phosphatidylinositol glycan, class B | 654.5857483 | 646.5559002 | 522.8462048 | 1311.180039 | 912.3631775 | 1151.96106 |
| 213889_at | phosphatidylinositol glycan, class L | 393.8778517 | 207.8866995 | 301.5016595 | 95.79765594 | 110.8962189 | 104.4099489 |
| 209998_at | phosphatidylinositol glycan, class O | 320.9419487 | 314.5265814 | 375.4195945 | 184.3584116 | 217.0482764 | 232.8124008 |

FIG 5, Page 23

| | | | | | | |
|---|---|---|---|---|---|---|
| 202743_at | phosphoinositide-3-kinase, regulatory subunit 3 (p55, gamma) [BLAST] | 156.069967 | 158.3102315 | 154.1854398 | 190.2516671 | 200.1450242 | 180.3851178 |
| 212740_at | phosphoinositide-3-kinase, regulatory subunit 4, p150 | 629.8233219 | 543.2368611 | 739.9775404 | 281.1222572 | 387.5079432 | 353.9902502 |
| 223373_s_at | phospholipase A2, group XIIA | 402.5826776 | 399.2538063 | 411.7491696 | 322.1756499 | 318.7127838 | 310.5904995 |
| 220892_s_at | phosphoserine aminotransferase 1 | 298.1635992 | 346.7492229 | 617.6446758 | 2901.922698 | 2112.93397 | 3632.92708 |
| 222687_s_at | phytoceramidase, alkaline | 205.906099 | 144.4590729 | 185.4940744 | 109.4773124 | 102.9340525 | 91.28548857 |
| 201860_s_at | plasminogen activator, tissue | 359.3686958 | 145.830189 | 197.2580006 | 5206.389931 | 1573.059699 | 2184.879147 |
| 40472_at | PLSC domain containing protein | 69.79238339 | 153.3010976 | 146.9170533 | 565.764638 | 350.4274684 | 585.3698568 |
| 208644_at | poly (ADP-ribose) polymerase family, member 1 | 338.5574102 | 362.726671 | 363.6800751 | 267.2812991 | 248.0145315 | 282.9307477 |
| 224427_s_at | poly(A) polymerase gamma | 301.3870988 | 227.2679728 | 298.2112318 | 132.804783 | 144.8558344 | 115.6605887 |
| 213887_s_at | polymerase (RNA) II (DNA directed) polypeptide E, 25kDa | 1683.574046 | 1346.168337 | 1567.374539 | 904.1651947 | 1030.266184 | 953.8105337 |
| 202306_at | polymerase (RNA) II (DNA directed) polypeptide G | 2639.145698 | 3132.447991 | 2517.710491 | 1796.496562 | 1717.401017 | 1894.149116 |
| 211730_s_at | polymerase (RNA) II (DNA directed) polypeptide L, 7.6kDa | 8360.510723 | 11000.00175 | 10047.42516 | 5250.107331 | 6065.631304 | 5647.334279 |
| 212199_at | PP784 protein | 2414.231775 | 1854.123701 | 2196.201839 | 959.8750975 | 1178.064473 | 1233.704109 |
| 203460_s_at | presenilin 1 (Alzheimer disease 3) | 1491.33636 | 1254.807548 | 1683.53471 | 657.7816287 | 689.5570025 | 894.6439513 |
| 207782_s_at | presenilin 1 (Alzheimer disease 3) | 1081.453851 | 701.7498112 | 909.2435685 | 437.3825282 | 431.4472899 | 449.5082902 |
| 200634_at | profilin 1 | 2244.4646 | 2552.924955 | 2764.44024 | 6855.520014 | 4706.233119 | 5550.170564 |
| 243773_at | programmed cell death 2 | 45.82928407 | 36.37951433 | 46.13657001 | 66.63638156 | 69.51193541 | 88.94222854 |
| 227751_at | programmed cell death 5 | 97.51062046 | 114.221564 | 134.3917739 | 62.29622234 | 63.64126867 | 62.81892646 |
| 240931_s_at | programmed cell death 6 | 15.85638811 | 16.08439704 | | 22.29516058 | 23.91887354 | |

FIG 5, Page 24

| | | | | | | | |
|---|---|---|---|---|---|---|---|
| 202927_at | protein (peptidyl-prolyl cis/trans isomerase) NIMA-interacting 1 | 893.893025 | 746.1686228 | 880.3547365 | 533.5912968 | 501.09487 | 481.4806553 |
| 213465_s_at | protein phosphatase 1, regulatory subunit 7 | 1787.573798 | 1700.931745 | 1891.759852 | 1412.582378 | 1337.792632 | 1347.845389 |
| 208616_s_at | protein tyrosine phosphatase type IVA, member 2 | 4974.950957 | 4230.553521 | 5256.685499 | 7229.142477 | 7674.370255 | 7082.898257 |
| 208615_s_at | protein tyrosine phosphatase type IVA, member 2 | 731.0030061 | 978.9997165 | 1033.287983 | 2093.153699 | 2337.430031 | 2697.0498 |
| 208617_s_at | protein tyrosine phosphatase type IVA, member 2 | 1077.053785 | 1902.742635 | 1334.193932 | 3146.865086 | 4018.404656 | 3983.332569 |
| 216988_s_at | protein tyrosine phosphatase type IVA, member 2 | 2514.906397 | 2315.96333 | 2652.353274 | 4118.888023 | 3791.722917 | 3962.270907 |
| 226006_at | Purkinje cell protein 2 | 1654.011398 | 1264.259627 | 1508.176289 | 618.5524513 | 912.9972636 | 685.5774779 |
| 223108_s_at | Putative S1 RNA binding domain protein | 334.9398674 | 322.695476 | 326.5293571 | 531.8053517 | 453.0742256 | 481.1350201 |
| 218511_s_at | pyridoxine 5'-phosphate oxidase | 418.5291336 | 347.455625 | 424.14102 | 290.4741277 | 288.6193468 | 288.0233611 |
| 226452_at | pyruvate dehydrogenase kinase, isoenzyme 1 | 149.0154892 | 162.3479233 | 134.0548001 | 266.7443839 | 341.4467959 | 317.4458689 |
| 213866_at | pyruvate dehydrogenase kinase, isoenzyme 2 | 34.97194322 | 34.78298373 | | 61.91668199 | 62.77963858 | |
| 226090_x_at | RAB, member of RAS oncogene family-like 3 | 249.1490091 | 251.2945189 | 249.747427 | 201.09208 | 213.4661311 | 212.427167 |
| 1556123_a_at | RAB11B, member RAS oncogene family | 166.183946 | 154.312022 | 175.9556226 | 73.34162691 | 99.68911598 | 77.35438416 |
| 228521_s_at | RAB4B, member RAS oncogene family | 254.6550386 | 283.9105516 | 278.2924669 | 131.8950651 | 117.1889684 | 116.2787154 |
| 201276_at | RAB5B, member RAS oncogene family | 894.161171 | 820.2025602 | 819.3328174 | 551.7397657 | 523.5305164 | 414.4981929 |
| 211961_s_at | RAB7, member RAS oncogene family [BLAST] | 2451.948726 | 2432.158803 | 2306.830844 | 1620.435146 | 1813.393009 | 1594.379516 |
| 211955_at | RAN binding protein 5 | 775.6610321 | 935.1414164 | 968.0670594 | 1958.733421 | 2149.565139 | 2293.28926 |

FIG 5, Page 25

| | | | | | | |
|---|---|---|---|---|---|---|
| 211952_at | RAN binding protein 5 | 160.2954601 | 196.2353135 | 229.703319 | 683.2733822 | 558.1814803 | 871.0572291 |
| 211953_s_at | RAN binding protein 5 | 1075.138811 | 946.4416243 | 1145.995804 | 2710.591101 | 2336.013837 | 3730.980212 |
| 211954_s_at | RAN binding protein 5 | 1130.443675 | 996.7699836 | 1279.208067 | 2609.548227 | 2823.474601 | 3209.990468 |
| 223554_s_at | RAN guanine nucleotide release factor | 148.8757163 | 106.1790986 | 133.8375127 | | 56.27479447 | 47.19403923 |
| 218526_s_at | RAN guanine nucleotide release factor | 648.0674185 | 605.439042 | 594.3122881 | 317.3886562 | 415.7555572 | 371.6879212 |
| 204337_at | regulator of G-protein signalling 4 | 2610.102012 | 3389.811346 | 2805.294548 | 11394.29415 | 12416.90438 | 6747.490942 |
| 204339_s_at | regulator of G-protein signalling 4 | 987.9770282 | 1345.780683 | 1079.502228 | 11209.43965 | 8169.161006 | 3437.123646 |
| 211753_s_at | relaxin 1 | 19.09872233 | 19.37414929 | | 14.19865131 | 14.65914766 | |
| 201529_s_at | replication protein A1, 70kDa | 907.2293101 | 701.0120268 | 827.1772564 | 538.5543685 | 509.4648023 | 554.4493844 |
| 201485_s_at | reticulocalbin 2, EF-hand calcium binding domain | 2596.047455 | 2528.395076 | 2440.459304 | 1690.234292 | 1545.280667 | 1421.087475 |
| 203344_s_at | retinoblastoma binding protein 8 | 521.8056141 | 458.3355801 | 509.6905358 | 633.6879765 | 635.0173884 | 608.9470043 |
| 209284_s_at | Retinoblastoma-associated protein 140 | 360.502487 | 443.2579913 | 356.5936605 | 586.3090313 | 582.0027107 | 570.9480046 |
| 225171_at | Rho GTPase activating protein 18 | 114.891152 | 185.19288 | 116.188706 | 521.7449064 | 419.1686456 | 626.0374601 |
| 225173_at | Rho GTPase activating protein 18 | 65.09324807 | 97.4339311 | 77.00164389 | 273.3772524 | 239.9826194 | 269.411782 |
| 216247_at | ribosomal protein S20 | 52.3656083 | 68.13385122 | 71.58294572 | 101.2567701 | 131.4074828 | 124.6461634 |
| 206918_s_at | RNA binding motif protein 12 | 1384.000157 | 1016.527903 | 1156.010995 | 533.4137299 | 754.0608159 | 622.2666402 |
| 225751_at | RNA binding motif protein 17 | 379.9345889 | 463.4595368 | 465.7822465 | 293.2228789 | 317.2692692 | 279.4916006 |
| 225326_at | RNA binding motif protein 27 | 943.9744374 | 772.717705 | 879.3629219 | 527.8409533 | 524.1344912 | 473.112512 |
| 207836_s_at | RNA binding protein with multiple splicing | 319.8134527 | 342.5491979 | 282.5170059 | 464.7656847 | 445.618615 | 469.4099043 |
| 217609_at | RPL13-2 pseudogene | 30.22987406 | 32.20144501 | | 55.45511631 | 58.45815589 | 57.06026066 |
| 207974_s_at | S-phase kinase-associated protein 1A (p19A) | 5988.650332 | 6173.790993 | 5924.940288 | 4388.788041 | 4644.356067 | 4493.632183 |

FIG 5, Page 26

| | | | | | | | | |
|---|---|---|---|---|---|---|---|---|
| 203226_s_at | sarcoma amplified sequence | 995.2444982 | 1091.948458 | 883.6334775 | 458.8772519 | 455.0770336 | 472.3539847 | |
| 32099_at | scaffold attachment factor B2 | 698.9899497 | 509.7481394 | 674.8575096 | 326.1863717 | 399.3450082 | 359.8055873 | |
| 219349_s_at | SEC5-like 1 (S. cerevisiae) | 241.8139712 | 241.4983545 | 250.4748071 | 187.6547582 | 194.8963912 | 173.6087293 | |
| 218407_x_at | Secreted protein of unknown function | 1069.129789 | 935.2172242 | 1077.989933 | 656.7047934 | 709.3615832 | 554.966757 | |
| 227034_at | septin 10 | 467.3099226 | 421.2991145 | 394.784917 | 761.1536503 | 624.339409 | 752.8256469 | |
| 204614_at | serine (or cysteine) proteinase inhibitor, clade B (ovalbumin), member 2 | 64.223341223 | 57.34056818 | 80.98880629 | 9710.115556 | 5230.267549 | 965.6355851 | |
| 225095_at | serine palmitoyltransferase, long chain base subunit 2 | 102.3597722 | 149.8608881 | 114.6123645 | 335.0256436 | 278.584959 | 338.4665335 | |
| 227785_at | serologically defined colon cancer antigen 8 | 153.8050692 | 182.5593993 | 148.6743845 | 282.5956902 | 330.2629276 | 266.1150103 | |
| 1553034_at | serologically defined colon cancer antigen 8 | 73.91720488 | 109.1746418 | 87.73048023 | 184.5563129 | 249.3399995 | 208.9773825 | |
| 202060_at | SH2 domain binding protein 1 (tetratricopeptide repeat containing) | 1937.355005 | 1711.230099 | 1728.497051 | 1026.570134 | 1207.243674 | 1161.761892 | |
| 204979_s_at | SH3 domain binding glutamic acid-rich protein | 152.2628133 | 109.9424856 | 119.0666134 | 44.9814139 | 43.14226921 | 39.53206452 | |
| 204657_s_at | SHB (Src homology 2 domain containing) adaptor protein B | 93.62876316 | | 106.6974453 | 180.3807311 | 178.9522494 | 192.7541382 | |
| 214853_s_at | SHC (Src homology 2 domain containing) transforming protein 1 | 6780.466512 | 5944.579875 | 6224.913176 | 3828.271981 | 4230.012923 | 3983.79605 | |
| 221551_x_at | sialyltransferase 7D ((alpha-N-acetylneuraminyl-2,3-beta-galactosyl-1,3)-N-acetyl galactosaminide alpha-2,6-sialyltransferase) | 129.0089009 | 153.5278742 | 177.2573742 | 286.3495339 | 236.4209357 | 255.8725942 | |
| 230290_at | signal peptide, CUB domain, EGF-like 3 | 315.81107575 | 353.6239844 | | 1716.634678 | 1429.694228 | | |

FIG 5, Page 27

| | | | | | | | | |
|---|---|---|---|---|---|---|---|---|
| 225289_at | signal transducer and activator of transcription 3 (acute-phase response factor) | 832.1255142 | 864.8970093 | 751.6677661 | 431.2453103 | 453.4040266 | 461.2911421 |
| 211456_x_at | Similar to 60S ribosomal protein L35 | 7705.38417 | 5573.477047 | 9144.350822 | 3261.218403 | 3132.663087 | 2469.675303 |
| 227116_at | Similar to C10orf94 protein | 912.2039636 | 941.6187419 | 801.8741195 | 435.2074571 | 568.8650232 | 490.8213478 |
| 224890_s_at | Similar to CG14977-PA | 1028.495699 | 1062.000649 | 913.1675017 | 569.7451152 | 721.1689877 | 554.8106479 |
| 1555841_at | Similar to RIKEN cDNA 5730528L13 gene | 421.3907308 | 309.7071502 | 475.2403821 | 769.9257772 | 858.1957907 | 906.8123789 |
| 235536_at | Similar to RIKEN cDNA E030024N20 gene | 104.2748161 | 100.8809585 | 99.29161086 | 65.58248094 | 79.73497818 | 67.46901742 |
| 224878_at | Similar to ubiquitin binding protein | 1484.127392 | 1025.734886 | 1373.299194 | 657.3135088 | 711.4279117 | 675.1301268 |
| 201138_s_at | Sjogren syndrome antigen B (autoantigen La) | 2457.903565 | 2799.979681 | 2611.512518 | 1866.307764 | 1981.914018 | 1917.031532 |
| 241900_at | SMAD specific E3 ubiquitin protein ligase 2 | 40.87453097 | 45.28883445 | 44.87484325 | 125.7270291 | 73.69653955 | 101.2306524 |
| 204790_at | SMAD, mothers against DPP homolog 7 (Drosophila) | 134.8277955 | 83.02690049 | 115.053922 | 502.1370167 | 463.1699032 | 826.0436565 |
| 208916_at | solute carrier family 1 (neutral amino acid transporter), member 5 | 302.6744872 | 423.0111623 | 244.551492 | 970.479204 | 813.2851229 | 1138.586455 |
| 203123_s_at | solute carrier family 11 (proton-coupled divalent metal ion transporters), member 2 | 386.7066507 | 394.6080034 | 456.0245623 | 202.86641 | 243.9392344 | 205.5635269 |
| 203124_s_at | solute carrier family 11 (proton-coupled divalent metal ion transporters), member 2 | 730.0168719 | 574.0798058 | 641.2139462 | 350.9943848 | 397.585014 | 314.5970789 |
| 203125_x_at | solute carrier family 11 (proton-coupled divalent metal ion transporters), member 2 | 285.1012639 | 232.3109382 | 291.8868798 | 141.9151413 | 139.5681282 | 120.4180994 |

FIG 5, Page 28

| | | | | | | | |
|---|---|---|---|---|---|---|---|
| 241866_at | solute carrier family 16 (monocarboxylic acid transporters), member 7 | 39.88438325 | 52.81035187 | 50.36070203 | 108.4817644 | 108.3399152 | 124.9931569 |
| 230494_at | solute carrier family 20 (phosphate transporter), member 1 | 267.8379408 | 179.8894115 | 238.9335123 | 662.3425387 | 714.3264595 | 796.6463565 |
| 209910_at | solute carrier family 25 (mitochondrial carrier; Graves disease autoantigen), member 16 | | 42.17957954 | 44.90027126 | 66.00630017 | 63.55962824 | 72.98591766 |
| 232432_s_at | solute carrier family 30 (zinc transporter), member 5 | 1293.797031 | 1300.881445 | 1267.525839 | 1042.585616 | 982.7175376 | 1128.119043 |
| 208921_s_at | sorcin | 2627.176189 | 2919.485535 | 2927.48864 | 2126.148516 | 2023.435657 | 1962.695702 |
| 224818_at | sortilin 1 | 869.3733585 | 1548.712285 | 1031.222146 | 374.9283437 | 326.0851323 | 407.055006 |
| 212797_at | sortilin 1 | 179.0654342 | 257.735843 | 190.0344283 | 83.2623606 | 68.62669262 | |
| 215820_x_at | sorting nexin 13 | 92.21547519 | | 87.44818511 | 147.8638085 | 141.7240335 | |
| 202358_s_at | sorting nexin 19 | 585.8504299 | 546.5928878 | 549.4378079 | 421.2952976 | 428.2606306 | 355.8676619 |
| 238923_at | speckle-type POZ protein | 39.66777444 | 38.36507941 | 42.6648252 | 60.69895692 | 69.31079949 | 78.77237517 |
| 1555883_s_at | spindlin family, member 3 | 183.6427311 | 150.7040405 | 157.5302525 | 83.46122976 | 100.3078485 | 91.98460511 |
| 215004_s_at | splicing factor 4 [BLAST] | 217.5917959 | 213.7078122 | 204.1052803 | 139.8669301 | 152.3983537 | 156.3524227 |
| 222311_s_at | splicing factor, arginine/serine-rich 15 | 83.49490517 | 87.26261527 | 92.73209011 | 61.0118877 | 53.80325244 | 42.05168552 |
| 213850_s_at | splicing factor, arginine/serine-rich 2, interacting protein | 953.249915 | 993.6242144 | 1003.048863 | 582.7530544 | 599.1183603 | 707.6149847 |
| 209376_x_at | splicing factor, arginine/serine-rich 2, interacting protein | 568.4688563 | 562.8539667 | 582.6635845 | 313.2958767 | 349.5921459 | 384.6588414 |
| 213152_s_at | Splicing factor, arginine/serine-rich, 46kD | 1130.516986 | 729.3296996 | 873.3554934 | 447.9634 | 491.1315512 | 486.2847127 |
| 204914_s_at | SRY (sex determining region Y)-box 11 | 85.71872207 | 210.7619854 | 105.198644 | 833.5464347 | 568.2455409 | 906.9174587 |
| 209478_at | stimulated by retinoic acid 13 | 1227.125959 | 870.0078507 | 1095.821371 | 458.1135857 | 352.2087209 | 366.1947664 |

FIG 5, Page 29

| | | | | | | |
|---|---|---|---|---|---|---|
| 201093_x_at | succinate dehydrogenase complex, subunit A, flavoprotein (Fp) | 891.9119223 | 1169.397331 | 980.9450327 | 560.4313423 | 696.8603855 | 542.3705607 |
| 210131_x_at | succinate dehydrogenase complex, subunit C, integral membrane protein, 15kDa | 1358.46331 | 1348.758336 | 1380.849882 | 1068.76993 | 1109.927694 | 1133.270142 |
| 203615_x_at | sulfotransferase family, cytosolic, 1A, phenol-preferring, member 1 | 109.2155674 | 106.8533454 | 104.060982 | 204.6364888 | 160.2355464 | 249.2831743 |
| 200642_at | superoxide dismutase 1, soluble (amyotrophic lateral sclerosis 1 (adult)) | 8105.325271 | 7115.571948 | 8177.033423 | 5940.165213 | 5952.930787 | 6067.667838 |
| 206020_at | suppressor of cytokine signaling 6 | 181.0187775 | 167.5214484 | 137.0393429 | 253.1258788 | 302.3208056 | 243.5512695 |
| 213936_x_at | surfactant, pulmonary-associated protein B | 82.72131237 | 75.32299374 | 73.35512735 | 110.9694282 | 132.7226109 | 131.3475309 |
| 204295_at | surfeit 1 | 1211.67746 | 1286.749358 | 1329.562867 | 888.790615 | 812.2104515 | 849.6450614 |
| 203019_x_at | synovial sarcoma, X breakpoint 2 interacting protein | 38.54669984 | 53.64897728 | 36.27477613 | 97.44015696 | 122.4018675 | 96.36107751 |
| 1552618_at | syntaxin 6 | 522.9768609 | 594.8362239 | 531.3447881 | 334.047471 | 262.4088676 | 213.529453 |
| 221449_s_at | T-cell immunomodulatory protein | 1681.666894 | 1988.929227 | 1791.358964 | 1227.405688 | 1395.299375 | 1281.295269 |
| 201999_s_at | t-complex-associated-testis-expressed 1-like 1 | 3150.023811 | 4048.623868 | 4215.069006 | 6475.262577 | 6843.774883 | 7032.612662 |
| 201023_at | TAF7 RNA polymerase II, TATA box binding protein (TBP)-associated factor, 55kDa | 3457.262811 | 2695.483841 | 3671.994933 | 2126.069439 | 1939.659415 | 2041.842326 |
| 235762_at | taste receptor, type 2, member 14 | 57.95678392 | 62.37314673 | 48.30132772 | 121.4422636 | 96.05407993 | 97.9132739 |
| 1556178_x_at | taube nuss homolog (mouse) | 110.7497867 | 58.13442312 | 74.54548481 | 27.09196022 | 24.96944896 | 30.49177892 |
| 44696_at | TBC1 domain family, member 13 | 255.0431783 | 252.4033166 | 274.8171681 | 204.8952347 | 227.2368727 | 209.1350854 |

FIG 5, Page 30

| | | | | | | | |
|---|---|---|---|---|---|---|---|
| 218466_at | TBC1 domain family, member 17 | 175.0124144 | 203.7424836 | 189.8111924 | 122.3407155 | 131.0943686 | 125.624614 |
| 208838_at | TBP-interacting protein | 746.6188467 | 839.7552059 | 651.3808572 | 1158.734513 | 1145.217919 | 1187.846077 |
| 208839_s_at | TBP-interacting protein | 732.3123583 | 861.3271091 | 644.9814727 | 1146.649549 | 1127.452208 | 1171.437739 |
| 204281_at | TEA domain family member 4 | | 80.56281029 | 104.0811297 | 363.2958146 | | 343.6428692 |
| 203235_at | thimet oligopeptidase 1 | 89.61664705 | 75.05044849 | 83.29389042 | 111.0176436 | 113.701358 | 118.856673 |
| 208864_s_at | thioredoxin | 7932.288202 | 8721.682019 | 8328.440377 | 6834.206861 | 6391.967198 | 6298.85512 |
| 201008_s_at | thioredoxin interacting protein | 7759.266648 | 3709.724176 | 5678.105629 | 744.0631227 | 886.0692779 | 354.0555802 |
| 201009_s_at | thioredoxin interacting protein | 5938.522595 | 2944.053432 | 4891.818362 | 714.1067951 | 740.6154129 | 436.5788506 |
| 201010_s_at | thioredoxin interacting protein | 7840.165842 | 5168.623236 | 6155.859338 | 990.0577277 | 1173.632238 | 614.2371364 |
| 203887_s_at | thrombomodulin | 83.88591026 | 91.62227749 | 178.1542258 | 1516.289963 | 594.0666395 | 2829.099811 |
| 227338_at | thyroid hormone receptor associated protein 3 | 1207.866698 | 1093.157629 | 948.6144092 | 683.5458138 | 770.1526965 | 669.4304579 |
| 213043_s_at | thyroid hormone receptor associated protein 4 | 363.8984716 | 372.0562198 | 403.7515267 | 162.5258396 | 202.3437522 | 193.3127621 |
| 1316_at | Thyroid hormone receptor, alpha (erythroblastic leukemia viral (v-erb-a) oncogene homolog, avian) | 38.68774268 | 41.43738777 | 35.87061313 | 46.80095623 | 48.95048601 | 48.51340876 |
| 239080_at | TIMM9 | 15.34563253 | 18.63947278 | 21.88710573 | 40.915462 | 30.73096554 | 41.30380624 |
| 229055_at | Transcribed locus | 77.96517144 | 47.69000204 | 53.10674089 | 395.0073006 | 425.446096 | 297.7033063 |
| 236117_at | Transcribed locus | 242.9962004 | | 220.770525 | 98.13604522 | | 87.75252907 |
| 239370_at | Transcribed locus | 78.80949477 | 155.2830316 | 66.86673231 | 1084.788711 | 410.218627 | 702.3071754 |
| 235466_s_at | Transcribed locus | 65.85674681 | 82.65195842 | 59.50989135 | 143.0088959 | 186.8450983 | 130.3134452 |
| 230449_x_at | Transcribed locus | 190.9103364 | 164.3150563 | 146.9291033 | 109.5339671 | 93.19736672 | 94.13412714 |
| 243378_at | Transcribed locus | 28.07023169 | 28.20541602 | 41.98785898 | 11.20163748 | 9.839745846 | 16.01488818 |
| 237652_at | Transcribed locus | 36.14133242 | 35.32051137 | 40.41659412 | 58.05730002 | 50.27168938 | 49.02398488 |
| 230493_at | Transcribed locus | 201.77683 | 394.2527221 | 261.4602521 | 2571.748187 | 2839.102899 | 1475.618586 |
| 240214_at | Transcribed locus | 57.36023053 | 60.0110764 | 65.6324416 | 171.5043272 | 155.5361391 | 186.3661166 |
| 244397_at | Transcribed locus | 69.26259636 | 70.30111013 | 60.94838224 | 111.1014751 | 112.1032912 | 111.7094579 |
| 235630_at | Transcribed locus | | 35.27109747 | 33.40055706 | 52.75373547 | 52.68777018 | 56.31119303 |
| 211704_s_at | Transcribed locus | 306.2233353 | 293.527844 | 403.5038247 | 151.5132796 | 137.2503095 | 191.589648 |
| 242007_at | Transcribed sequences | 180.0420752 | 132.3994183 | 117.4615325 | 29.03655478 | 49.08007369 | 55.43682073 |

FIG 5, Page 31

| | | | | | | | |
|---|---|---|---|---|---|---|---|
| 205255_x_at | transcription factor 7 (T-cell specific, HMG-box) | 103.8766082 | 204.8534227 | 125.6165274 | 690.9518929 | 540.1715674 | 536.2135774 |
| 207627_s_at | transcription factor CP2 | 256.4962117 | 281.5430853 | 262.6331897 | 193.5955887 | 174.6296201 | 195.4853647 |
| 228834_at | transducer of ERBB2, 1 | 1869.17998 | 2877.621303 | 1589.458365 | 610.1456625 | 787.2258675 | 551.06798 |
| 202704_at | transducer of ERBB2, 1 | 2670.432104 | 2743.031832 | 2530.896795 | 874.5707014 | 798.9101768 | 1016.145532 |
| 208943_s_at | Translocation protein 1 | 2934.094669 | 2521.311075 | 2899.619678 | 1952.664391 | 2126.608843 | 2023.960603 |
| 222477_s_at | transmembrane 7 superfamily member 3 | 1315.67618 | 1206.894876 | 1221.790007 | 568.3206019 | 587.5082303 | 528.8504559 |
| 209149_s_at | transmembrane 9 superfamily member 1 | 945.0792329 | 964.224874 | 961.8195606 | 819.2933588 | 719.686327 | 737.1017797 |
| 201078_at | transmembrane 9 superfamily member 2 | 4505.815093 | 4282.516591 | 4309.412989 | 3734.451012 | 3905.461008 | 3942.978559 |
| 219074_at | transmembrane protein 34 | 919.9649533 | 878.4949535 | 1133.400923 | 414.0027877 | 401.6368203 | 536.1793165 |
| 222987_s_at | transmembrane protein 9 | 714.3346344 | 658.1766385 | 700.8134994 | 441.5359978 | 556.5562723 | 494.3867566 |
| 223384_s_at | tripartite motif-containing 4 | 915.851087 | 759.213276 | 842.7010931 | 412.2351948 | 574.9139574 | 482.1273791 |
| 58308_at | tripartite motif-containing 62 | 99.22866074 | 84.71509995 | 86.42513808 | 56.53280185 | 59.3759915 | 60.60409638 |
| 223436_s_at | TRNA splicing 2' phosphotransferase 1 | 108.8408333 | 169.8714057 | 118.7980286 | 296.9678903 | 337.8109436 | 294.357888 |
| 1555374_at | tubulin tyrosine ligase | 49.31723955 | 44.63490934 | 42.18301897 | 81.03326836 | 88.26459374 | 65.21736657 |
| 221473_x_at | tumor differentially expressed 1 | 2768.286749 | 2615.979368 | 2429.070049 | 1662.602003 | 1885.954991 | 1472.948619 |
| 207643_s_at | tumor necrosis factor receptor superfamily, member 1A | 2394.994075 | 2382.873732 | 2168.39941 | 833.9583111 | 1293.326399 | 943.7611036 |
| 207536_s_at | tumor necrosis factor receptor superfamily, member 9 | 13.03584058 | 20.72678669 | 15.62996047 | 36.75770797 | 30.23282922 | 36.82971101 |
| 224836_at | tumor protein p53 inducible nuclear protein 2 [BLAST] | 413.2574398 | 376.2258431 | 472.4114233 | 201.5001141 | 195.5522975 | 246.3355901 |
| 210609_s_at | tumor protein p53 inducible protein 3 | 1240.303919 | 1024.319405 | 1016.439688 | 392.4085006 | 512.5769938 | 382.4371009 |
| 200599_s_at | tumor rejection antigen (gp96) 1 | 11248.22634 | 11008.04035 | 13028.61155 | 6429.548466 | 5348.660327 | 7283.903021 |
| 216449_x_at | tumor rejection antigen (gp96) 1 | 12606.70604 | 7312.097603 | 15410.08498 | 3423.073874 | 2638.959455 | 3117.832303 |
| 200598_s_at | tumor rejection antigen (gp96) 1 | 10303.44332 | 6711.628315 | 13240.85182 | 3698.116936 | 2465.093855 | 3504.376727 |

FIG 5, Page 32

| | | | | | | | |
|---|---|---|---|---|---|---|---|
| 239451_at | tumor rejection antigen (gp96) 1 | 527.6753645 | 375.9242158 | 860.2193084 | 68.08831721 | 57.52183153 | 64.44191863 |
| 217914_at | two pore segment channel 1 | 116.615093 | 142.3389837 | 122.0583427 | 243.7462208 | 396.3608672 | 252.7851313 |
| 205546_s_at | tyrosine kinase 2 | 375.6865993 | 377.5883239 | 437.8958874 | 256.4428915 | 233.2089457 | 231.9306287 |
| 215884_s_at | ubiquilin 2 | 1896.320751 | 1736.688458 | 1760.597817 | 1341.946114 | 1505.143791 | 1465.945966 |
| 202090_s_at | Ubiquinol-cytochrome c reductase (6.4kD) subunit | 4345.984022 | 3980.256728 | 4369.193667 | 3402.027336 | 3482.405179 | 3379.543468 |
| 223701_s_at | ubiquitin specific protease 47 | 686.3595627 | 812.401409 | 688.6592882 | 283.0662317 | 414.9771733 | 387.1535161 |
| 223117_s_at | ubiquitin specific protease 47 | 836.079351 | 941.5365787 | 694.4289594 | 349.3921649 | 464.0490834 | 473.2533058 |
| 221518_s_at | ubiquitin specific protease 47 [BLAST] | 1255.350359 | 1521.358132 | 1225.499181 | 654.871098 | 672.0893113 | 796.4435314 |
| 230761_at | ubiquitin specific protease 7 (herpes virus-associated) | 83.24477421 | 87.10734001 | 78.18821544 | 36.9930013 | 55.47339147 | 49.04219852 |
| 213535_s_at | ubiquitin-conjugating enzyme E2I (UBC9 homolog, yeast) | 2507.974992 | 2313.206337 | 2595.556058 | 1785.461141 | 1782.42517 | 2023.628636 |
| 221746_at | ubiquitin-like 4 | 179.50605 | 169.2101888 | 166.1971008 | 228.8827574 | 207.3677189 | 224.9478864 |
| 218011_at | ubiquitin-like 5 | 3124.538568 | 2901.25996 | 3780.428709 | 2175.128589 | 2074.201389 | 2025.91201 |
| 212008_at | UBX domain containing 2 | 964.7468635 | 965.5992101 | 907.6468658 | 716.0322612 | 739.4368208 | 640.3645114 |
| 1555561_a_at | UBX domain containing 2 | 108.9454607 | 112.6980248 | 107.131393 | 195.3451269 | 173.0930956 | 197.9596158 |
| 218801_at | UDP-glucose ceramide glucosyltransferase-like 2 | 285.0869898 | 393.6985286 | 325.5506868 | 531.3313599 | 610.5277864 | 637.0284322 |
| 214169_at | UDP-glucose ceramide glucosyltransferase-like 2 | 142.0209496 | 87.3755764 | 145.1993248 | 34.9883395 | 39.27469377 | 42.11820982 |
| 208970_s_at | unc-84 homolog A (C. elegans) | 3941.155227 | 2972.94196 | 3758.457225 | 1876.476953 | 2184.023971 | 1609.00746 |
| 208971_at | uroporphyrinogen decarboxylase | 1737.327882 | 1298.028676 | 1382.221436 | 758.5080246 | 896.3241962 | 773.7877176 |
| 218415_at | uroporphyrinogen decarboxylase | 271.9395647 | 273.6951157 | 231.8093397 | 129.1063794 | 117.2841708 | 136.5957786 |
| 223346_at | vacuolar protein sorting 33B (yeast) | 275.6815742 | 238.448994 | 285.3670279 | 197.5447154 | 189.9045301 | 165.857154 |
| | vacuolar protein sorting protein 18 | | | | | | |

FIG 5, Page 33

| | | | | | | | |
|---|---|---|---|---|---|---|---|
| 201831_s_at | Vesicle docking protein p115 | 714.940175 | 782.6968653 | 675.4266868 | 1320.306723 | 1119.747271 | 1333.577603 |
| 242356_at | vesicle transport through interaction with t-SNAREs homolog 1A (yeast) | 39.54819429 | 44.99301921 | 36.9456868 | 55.26215404 | 55.29381071 | 53.80855053 |
| 201557_at | vesicle-associated membrane protein 2 (synaptobrevin 2) | 133.6163086 | 146.71141726 | 136.0354114 | 104.3619159 | 104.5200849 | 104.1052526 |
| 218851_s_at | WD repeat domain 33 | 149.3942726 | | 212.7948752 | 25.17964857 | 28.56759368 | 41.40459112 |
| 231960_at | WD repeat domain 9 | 109.9628282 | 111.9042126 | 84.10780277 | 43.21218776 | 61.81531998 | 52.01878187 |
| 231227_at | wingless-type MMTV integration site family, member 5A | 155.7586814 | 111.8222815 | 128.101971 | 428.8074469 | 277.2745322 | 287.5848931 |
| 204710_s_at | WIPI49-like protein 2 | 1903.914318 | 1472.961261 | 1670.702586 | 997.2078282 | 1121.163633 | 1120.446947 |
| 208453_s_at | X-prolyl aminopeptidase (aminopeptidase P) 1, soluble | 646.4742053 | 774.5245337 | 615.503143 | 1039.830117 | 997.0689902 | 1088.880235 |
| 225959_s_at | zinc and ring finger 1 | 106.2031506 | 154.5505373 | 108.1427517 | 257.2168762 | 214.0846787 | 260.3250736 |
| 226897_s_at | zinc finger CCCH type domain containing 7 | 743.9616577 | 647.9771902 | 754.9804223 | 469.677012 | 480.9783497 | 418.9826031 |
| 218348_s_at | zinc finger CCCH type domain containing 7 | 1149.954577 | 1298.367904 | 1140.322951 | 799.9256726 | 820.007814 | 746.8520734 |
| 213051_at | zinc finger CCCH type, antiviral 1 | 794.6628664 | 757.6841926 | 804.2421442 | 434.8278555 | 588.447188 | 465.6703204 |
| 225634_at | zinc finger CCCH type, antiviral 1 | 928.8202511 | 882.1524133 | 1008.463329 | 492.7456577 | 495.3561338 | 626.1270218 |
| 1569312_at | zinc finger protein 146 | 65.41463947 | 71.75946205 | 85.89453716 | 121.4661821 | 134.2106693 | 138.685731 |
| 235164_at | zinc finger protein 25 (KOX 19) | 138.9487166 | 139.9820241 | 118.8706726 | 188.0869999 | 207.6269481 | 230.1041139 |
| 213698_at | zinc finger protein 258 | 955.7709674 | 1131.720297 | 1137.412723 | 524.9241043 | 557.4125371 | 533.6874824 |
| 219924_s_at | zinc finger protein 258 | 668.8347593 | 729.3509141 | 736.1783243 | 310.0922432 | 273.9114529 | 331.1199504 |
| 211975_at | Zinc finger protein 289, ID1 regulated | 731.7060598 | 550.010035 | 839.713963 | 343.8226725 | 387.3882254 | 387.7265975 |
| 224276_at | zinc finger protein 33a (KOX 31) | 13.54642578 | 13.51772142 | | 23.38669058 | 23.007810381 | |
| 236562_at | zinc finger protein 439 | 98.10067464 | 95.33435253 | | 66.23993693 | 74.16289247 | 65.03814635 |
| 218735_s_at | zinc finger protein 544 | 143.3303043 | 222.9380054 | 160.7440712 | 340.4763378 | 319.7222713 | 324.6963117 |

FIG 5, Page 34

| 1553286_at | zinc finger protein 555 | 134.9737505 | 120.23828 | 136.8063233 | 73.30302797 | 79.9182577 | 95.71555871 |
| 1569366_a_at | zinc finger protein 569 | 51.75305031 | 57.10460045 | 51.224858796 | 81.66808025 | 80.51411436 | 75.35018767 |
| 236155_at | zinc finger, CCHC domain containing 6 | 178.3917359 | 217.4549849 | 236.0118391 | 102.0272899 | 100.7228211 | 105.0546255 |
| 238800_s_at | zinc finger, CCHC domain containing 6 | 127.2855723 | 139.6974973 | 143.8109602 | 63.50921641 | 92.05186964 | 79.95530725 |
| 236243_at | zinc finger, CCHC domain containing 6 | 136.9184418 | 181.6155153 | 149.4144339 | 56.32660776 | 63.88876938 | 83.57604461 |
| 1555562_a_at | zinc finger, CCHC domain containing 7 | 117.0740237 | 113.0453341 | 118.9287291 | 154.9821096 | 193.9550218 | 164.4180424 |
| 235068_at | zinc finger, DHHC domain containing 21 | 124.0041316 | 137.9822394 | 138.0582537 | 187.7067537 | 188.2194243 | 202.0766651 |
| 228005_at | zinc finger, X-linked, duplicated B | 531.0800877 | 364.2026062 | 488.5514918 | 249.9304145 | 187.1665609 | 240.7717828 |
| 202939_at | zinc metallopeptidase (STE24 homolog, yeast) | 2880.445214 | 2911.818084 | 2869.408338 | 2583.521832 | 2522.109499 | 2555.492375 |
| 222606_at | Zwilch | 381.6681325 | 390.4539169 | 302.2194797 | 637.1611886 | 531.1983634 | 701.2169634 |

FIG 5, Page 35

```
SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
aaagaggtcc tgatggagag c                                          21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
tagatgtagt agagcggcac ct                                         22

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
aacgccttct tatcgtggtg                                            20

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
gtgagagcct caagactgg                                             19
```

DIFFERENTIATION OF MULTI-LINEAGE PROGENITOR CELLS TO RESPIRATORY EPITHELIAL CELLS

CROSS-REFERENCE TO RELATED APPLICATIONS

This application claims benefit of U.S. Application No. 60/792,511, filed Apr. 17, 2006, which is incorporated by reference in its entirety.

TECHNICAL FIELD

The invention relates to respiratory epithelial cells, and more particularly, to differentiating multi-lineage progenitor cells (MLPC) from human blood to respiratory epithelial cells, and use of such cells for regenerative therapies.

BACKGROUND

Progenitor cells capable of hematopoietic reconstitution after mycloablative therapy have been identified in a number of sources including the bone marrow, umbilical cord and placental blood, and in the peripheral blood of subjects treated with stem cell-mobilizing doses of granulocyte-colony stimulation factor. These cells, often referred to as hematopoietic stem cells (HSC), are identified by the presence of cell surface glycoproteins such as CD34 and CD133. HSC represent a very small percentage of the total population of cells given as part of a 'bone marrow transplant' and are considered to be the life-saving therapeutic portion of this treatment responsible for the restoration of the blood-forming capacity of patients given myeloablative doses of chemotherapy or radiation therapy. Stem cell therapies via bone marrow transplantation have become a standard treatment for a number of intractable leukemias and genetic blood disorders.

Recent studies have suggested the presence of a more primitive cell population in the bone marrow capable of self-renewal as well as differentiation into a number of different tissue types other than blood cells. These multi-potential cells were discovered as a minor component in the CD34-plastic-adherent cell population of adult bone marrow, and are variously referred to as mesenchymal stem cells (MSC) (Pittenger, et al., *Science* 284: 143-147 (1999)) or multi-potent adult progenitor cells (MAPC) cells (Furcht, L. T., et al., U.S. patent publication 20040107453 A1). MSC cells do not have a single specific identifying marker, but have been shown to be positive for a number of markers, including CD29, CD90, CD105, and CD73, and negative for other markers, including CD14, CD3, and CD34. Various groups have reported to differentiate MSC cells into myocytes, neurons, pancreatic beta-cells, liver cells, bone cells, and connective tissue. Another group (Wernet et al., U.S. patent publication 20020164794 A1) has described an unrestricted somatic stem cell (USSC) with multi-potential capacity that is derived from a $CD45^-/CD34^-$ population within cord blood.

SUMMARY

The invention is based on the discovery that respiratory epithelial cells can be obtained by inducing differentiation of multi-lineage progenitor cells (MLPC) from human fetal blood. As described herein, fetal blood MLPC are distinguished from bone marrow-derived MSC, HSC, and USSC on the basis of their immunophenotypic characteristics, gene expression profile, morphology, and distinct growth pattern.

The invention provides methods for developing monotypic clonal cell lines from individual cells. The invention also provides methods for cryopreserving MLPC (e.g., for cord blood banking) and methods of using MLPC in regenerative therapies.

In one aspect, the invention features a composition that includes a purified population of human fetal blood MLPC or a clonal line of human fetal blood MLPC and a differentiation medium effective to induce differentiation of the MLPC into cells having a respiratory epithelial cell phenotype, wherein the MLPC are positive for CD9, negative for CD45, negative for CD34, and negative for SSEA-4. The differentiation medium can include hydrocortisone, epidermal growth factor, insulin, triiodothyronine, transferrin, and bovine serum albumin. In some embodiments, the differentiation medium further includes retinoic acid, pituitary extract, epinephrine, and/or an antibiotic.

The invention also features a composition that includes a mixture of MLPC and cells having a respiratory epithelial cell phenotype. The composition further can include a culture medium or a differentiation medium. The differentiation medium can include hydrocortisone, epidermal growth factor, insulin, triiodothyronine, transferrin, and bovine serum albumin. In some embodiments, the differentiation medium further includes retinoic acid, pituitary extract, epinephrine, and/or an antibiotic. The culture medium or the differentiation medium can include a cryopreservative.

In another aspect, the invention features a method of producing a population of cells having a respiratory epithelial cell phenotype. The method includes culturing a purified population of MLPC or a clonal line of MLPC with a differentiation medium effective to induce differentiation of the MLPC into cells having the respiratory epithelial cell phenotype, wherein the MLPC are positive for CD9, negative for CD45, negative for CD34, and negative for SSEA-4. The differentiation medium can include hydrocortisone, epidermal growth factor, insulin, triiodothyronine, transferrin, and bovine serum albumin. In some embodiments, the differentiation medium further includes retinoic acid, pituitary extract, epinephrine, and/or an antibiotic. The method further can include testing the cells having the respiratory epithelial cell phenotype for surfactant protein C (e.g., by staining with an antibody having binding affinity for prosurfactant protein C).

In yet another aspect, the invention features a method for producing a population of cells having a respiratory epithelial cell phenotype from human fetal blood. The method includes contacting a human fetal blood sample with a composition, the composition including dextran, anti-glycophorin A antibody, anti-CD15 antibody, and anti-CD9 antibody; allowing the sample to partition into an agglutinate and a supernatant phase; recovering cells from the supernatant phase; purifying MLPC from the recovered cells by adherence to a solid substrate, wherein the MLPC are positive for CD9 and positive for CD45; culturing the MLPC such that the MLPC obtain a fibroblast morphology; and culturing the MLPC having the fibroblast morphology with a differentiation medium effective to induce differentiation of the MLPC into cells having the respiratory epithelial cell phenotype. The method further can include testing the cells having the respiratory epithelial cell phenotype for surfactant protein C. The method also can include producing a clonal line of MLPC from the MLPC having the fibroblast morphology before culturing with the differentiation medium.

The invention also features a clonal population of cells having a respiratory epithelial cell phenotype and compositions containing such clonal populations. Such cells can have enhanced expression of mRNA for a lysosomal ATPase relative to a clonal population of MLPC. In one embodiment, a composition includes a clonal population of cells having a respiratory epithelial cell phenotype and a culture medium. Such compositions further can include a cryopreservative (e.g., dimethylsulfoxide (DMSO) such as 1 to 10% DMSO). The cryopreservative can be fetal bovine serum, human serum, or human serum albumin in combination with one or more of the following: DMSO, trehalose, and dextran. For example, the cryopreservative can be human serum, DMSO, and trehalose, or fetal bovine serum and DMSO.

The invention also features an article of manufacture that includes a clonal population of cells having a respiratory epithelial cell phenotype. The clonal population can be housed within a container (e.g., a vial or a bag). The container further can include a cryopreservative.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a schematic of a cell separation procedure for purifying MLPC from fetal blood.

FIG. 2A shows an early culture of MLPC isolated from umbilical cord blood demonstrating the cells in the leukocyte morphology phase. FIG. 2B shows a culture of MLPC beginning to change their morphology from leukocyte to fibroblast morphology. FIG. 2C shows a later culture of MLPC in logarithmic growth phase. FIG. 2D shows a fully confluent culture of MLPC.

FIG. 5 is a table that lists the genes that are differentially expressed between MPLC induced in SAGM™ (both mixed cell and clonal line C3) and control MLPC.

DETAILED DESCRIPTION

Figure 2A:
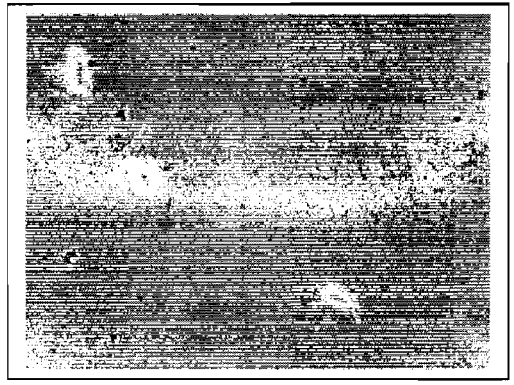
FIG. 2A-2D are photomicrographs depicting the morphology of developing MLPC.
Figure 2B:
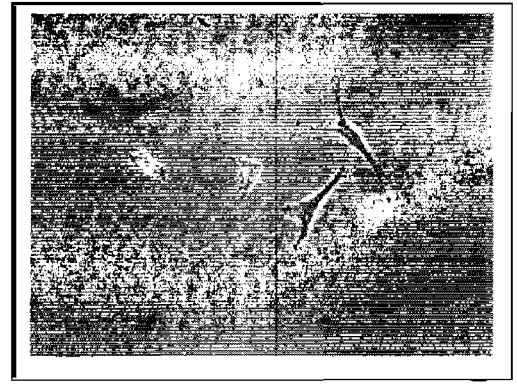

In general, the invention provides purified populations of MLPC from human fetal blood (e.g., umbilical cord blood ("cord blood"), placental blood, or the blood from a fetus) and clonal MLPC lines derived from individual MLPC. Fetal blood provides a source of cells that is more immature than adult bone marrow and has a higher percentage of cells bearing immature cell surface markers. Consequently, there may be advantages in the expansion and differentiation capacity of the progenitor cells from fetal blood. As described herein, MLPC have immunophenotypic characteristics and a gene expression profile distinct from bone marrow derived MSC's, bone marrow-derived HSC, and umbilical cord blood-derived HSC and USSC. The cells described herein have the capacity to self renew and differentiate into diverse cells and tissue types. For example, MLPC are capable of differentiating to respiratory epithelial cells as shown below. MLPC can be used to develop cellular therapies and establish cryopreserved cell banks for future regenerative medicine procedures. MLPC also can be modified such that the cells can produce one or more polypeptides or other therapeutic compounds of interest.

Cell Separation Compositions

MLPC can be isolated from fetal blood (e.g., cord blood) using the negative selection process and cell separation compositions disclosed in U.S. Pat. No. 7,160,723. Such cell compositions can include dextran and one or more antibodies against (i.e., that have binding affinity for) a cell surface antigen.

Dextran is a polysaccharide consisting of glucose units linked predominantly in alpha (1 to 6) mode. Dextran can cause stacking of erythrocytes (i.e., rouleau formation) and thereby facilitate the removal of erythroid cells from solution. Antibodies against cell surface antigens can facilitate the removal of blood cells from solution via homotypic agglutination (i.e., agglutination of cells of the same cell type) and/or heterotypic agglutination (i.e., agglutination of cells of different cell types).

For example, a cell separation composition can include dextran and antibodies against glycophorin A, CD15, and CD9. Cell separation compositions also can contain antibodies against other blood cell surface antigens including, for example, CD2, CD3, CD4, CD8, CD72, CD16, CD41a, HLA Class I, HLA-DR, CD29, CD11a, CD11b, CD11c, CD19, CD20, CD23, CD39, CD40, CD43, CD44, CDw49d, CD53, CD54, CD62L, CD63, CD66, CD67, CD81, CD82, CD99, CD100, Leu-13, TPA-1, surface Ig, and combinations thereof. Thus, cell separation compositions can be formulated to selectively agglutinate particular types of blood cells.

Typically, the concentration of anti-glycophorin A antibodies in a cell separation composition ranges from 0.1 to 15 mg/L (e.g., 0.1 to 10 mg/L, 1 to 5 mg/L, or 1 mg/L). Anti-glycophorin A antibodies can facilitate the removal of red cells from solution by at least two mechanisms. First, anti-glycophorin A antibodies can cause homotypic agglutination of erythrocytes since glycophorin A is the major surface glycoprotein on erythrocytes. In addition, anti-glycophorin A antibodies also can stabilize dextran-mediated rouleau formation. Exemplary monoclonal anti-glycophorin A antibodies include, without limitation, 107FMN (Murine IgG1 isotype), YTH89.1 (Rat IgG2b isotype), 2.2.2.E7 (Murine IgM isotype; BioE, St. Paul, Minn.), and E4 (Murine IgM isotype). See e.g., M. Vanderlaan et al., *Molecular Immunology* 20:1353 (1983); Telen M. J. and Bolk, T. A., *Transfusion* 27: 309 (1987); and Outram S. et al., *Leukocyte Research*. 12:651 (1988).

The concentration of anti-CD 15 antibodies in a cell separation composition can range from 0.1 to 15 mg/L (e.g., 0.1 to 10, 1 to 5, or 1 mg/L). Anti-CD15 antibodies can cause homotypic agglutination of granulocytes by crosslinking CD 15 molecules that are present on the surface of granulocytes.

Anti CD15 antibodies also can cause homotypic and heterotypic agglutination of granulocytes with monocytes, NK-cells and B-cells by stimulating expression of adhesion molecules (e.g., L-selectin and beta-2 integrin) on the surface of granulocytes that interact with adhesion molecules on monocytes, NK-cells and B-cells. Heterotypic agglutination of these cell types can facilitate the removal of these cells from solution along with red cell components. Exemplary monoclonal anti-CD15 antibodies include, without limitation, AHN1.1 (Murine IgM isotype), FMC-10 (Murine IgM isotype), BU-28 (Murine IgM isotype), MEM-157 (Murine IgM isotype), MEM-158 (Murine IgM isotype), 324.3.B9 (Murine IgM isotype; BioE, St. Paul, Minn.), and MEM-167 (Murine IgM isotype). See e.g., *Leukocyte typing IV* (1989); *Leukocyte typing II* (1984); *Leukocyte typing VI* (1995); Solter D. et al., *Proc. Natl. Acad. Sci. USA* 75:5565 (1978); Kannagi R. et al., *J. Biol. Chem.* 257:14865 (1982); Magnani, J. L. et al., *Arch. Biochem. Biophys* 233:501 (1984); Eggens I. et al., *J. Biol. Chem.* 264:9476 (1989).

The concentration of anti-CD9 antibodies in a cell separation composition can range from 0.1 to 15, 0.1 to 10, 1 to 5, or 1 mg/L. Anti-CD9 antibodies can cause homotypic agglutination of platelets. Anti-CD9 antibodies also can cause heterotypic agglutination of granulocytes and monocytes via platelets that have adhered to the surface of granulocytes and monocytes. CD9 antibodies can promote the expression of platelet p-selectin (CD62P), CD41/61, CD31, and CD36, which facilitates the binding of platelets to leukocyte cell surfaces. Thus, anti-CD9 antibodies can promote multiple cell-cell linkages and thereby facilitate agglutination and removal from solution. Exemplary monoclonal anti-CD9 antibodies include, without limitation, MEM-61 (Murine IgG1 isotype), MEM-62 (Murine IgG1 isotype), MEM-192 (Murine IgM isotype), FMC-8 (Murine IgG2a isotype), SN4 (Murine IgG1 isotype), 8.10.E7 (Murine IgM isotype; BioE, St. Paul, Minn.), and BU-16 (Murine IgG2a isotype). See e.g., *Leukocyte typing VI* (1995); *Leukocyte typing II* (1984); Von dem Bourne A. E. G. Kr. and Moderman P. N. (1989) In *Leukocyte typing IV* (ed. W. Knapp, et al), pp. 989-92, Oxford University Press, Oxford; Jennings, L. K., et al. In *Leukocyte typing V*, ed. S. F. Schlossmann et al., pp. 1249-51, Oxford University Press, Oxford (1995); Lanza F. et al., *J. Biol. Chem.* 266:10638 (1991); Wright et al., *Immunology Today* 15:588 (1994); Rubinstein E. et al., *Seminars in Thrombosis and Hemostasis* 21:10 (1995).

In some embodiments, a cell separation composition contains antibodies against CD41, which can selectively agglutinate platelets. In some embodiments, a cell separation composition contains antibodies against CD3, which can selectively agglutinate T-cells. In some embodiments, a cell separation composition contains antibodies against CD2, which can selectively agglutinate T-cells and NK cells. In some embodiments, a cell separation composition contains antibodies against CD72, which can selectively agglutinate B-cells. In some embodiments, a cell separation composition contains antibodies against CD16, which can selectively agglutinate NK cells and neutrophilic granulocytes. The concentration of each of these antibodies can range from 0.01 to 15 mg/L. Exemplary anti-CD41 antibodies include, without limitation, PLT-1 (Murine IgM isotype), CN19 (Murine $IgG_1$ isotype), and 8.7.C3 (Murine IgG1 isotype). Non-limiting examples of anti-CD3 antibodies include OKT3 (Murine $IgG_1$), HIT3a (Murine IgG2a isotype), SK7 (Murine $IgG_1$) and BC3 (Murine $IgG_{2a}$). Non-limiting examples of anti-CD2 antibodies include 7A9 (Murine IgM isotype), T11 (Murine $IgG_1$ isotype), and Leu5b (Murine $IgG_{2a}$ Isotype). Non-limiting examples of anti-CD72 antibodies include BU-40 (Murine $IgG_1$ isotype) and BU-41 (Murine $IgG_1$ isotype). Non-limiting examples of anti-CD16 antibodies include 3G8 (Murine IgG).

As mentioned above, cell separation compositions can be formulated to selectively agglutinate particular blood cells. As an example, a cell separation composition containing antibodies against glycophorin A, CD15, and CD9 can facilitate the agglutination of erythrocytes, granulocytes, NK cells, B cells, and platelets. T cells, NK cells and rare precursor cells such as MLPC then can be recovered from solution. If the formulation also contained an antibody against CD3, T cells also could be agglutinated, and NK cells and rare precursors such as MLPC could be recovered from solution.

Cell separation compositions can contain antibodies against surface antigens of other types of cells (e.g., cell surface proteins of tumor cells). Those of skill in the art can use routine methods to prepare antibodies against cell surface antigens of blood, and other, cells from humans and other mammals, including, for example, non-human primates, rodents (e.g., mice, rats, hamsters, rabbits and guinea pigs), swine, bovines, and equines.

Typically, antibodies used in the composition are monoclonal antibodies, which are homogeneous populations of antibodies to a particular epitope contained within an antigen. Suitable monoclonal antibodies are commercially available, or can be prepared using standard hybridoma technology. In particular, monoclonal antibodies can be obtained by techniques that provide for the production of antibody molecules by continuous cell lines in culture, including the technique described by Kohler, G. et al., *Nature,* 1975, 256:495, the human B-cell hybridoma technique (Kosbor et al., *Immunology Today* 4:72 (1983); Cole et al., *Proc. Natl. Acad. Sci. USA* 80:2026 (1983)), and the EBV-hybridoma technique (Cole et al., "Monoclonal Antibodies and Cancer Therapy," Alan R. Liss, Inc., pp. 77-96 (1983)).

Antibodies can be of any immunoglobulin class including IgG, IgM, IgE, IgA, IgD, and any subclass thereof Antibodies of the IgG and IgM isotypes are particularly useful in cell separation compositions of the invention. Pentameric IgM antibodies contain more antigen binding sites than IgG antibodies and can, in some cases (e.g., anti-glycophorin A and anti-CD 15), be particularly useful for cell separation reagents. In other cases (e.g., anti-CD9 antibodies), antibodies of the IgG isotype are particularly useful for stimulating homotypic and/or heterotypic agglutination.

Antibodies against cell surface antigens can be provided in liquid phase (i.e., soluble). Liquid phase antibodies typically are provided in a cell separation composition at a concentration between about 0.1 and about 15 mg/l (e.g., between 0.25 to 10, 0.25 to 1, 0.5 to 2, 1 to 2, 4 to 8, 5 to 10 mg/l).

Antibodies against cell surface antigens also can be provided in association with a solid phase (i.e., substrate-bound). Antibodies against different cell surface antigens can be covalently linked to a solid phase to promote crosslinking of cell surface molecules and activation of cell surface adhesion molecules. The use of substrate-bound antibodies can facilitate cell separation (e.g., by virtue of the mass that the particles contribute to agglutinated cells, or by virtue of properties useful for purification).

In some embodiments, the solid phase with which a substrate-bound antibody is associated is particulate. In some embodiments, an antibody is bound to a latex microparticle such as a paramagnetic bead (e.g., via biotin-avidin linkage, covalent linkage to COO groups on polystyrene beads, or covalent linkage to $NH_2$ groups on modified beads). In some embodiments, an antibody is bound to an acid-etched glass particle (e.g., via biotin-avidin linkage). In some embodiments, an antibody is bound to an aggregated polypeptide such as aggregated bovine serum albumin (e.g., via biotin-avidin linkage, or covalent linkage to polypeptide COO groups or $NH_2$ groups). In some embodiments, an antibody is covalently linked to a polysaccharide such as high molecular weight (e.g., >1,000,000 $M_r$) dextran sulfate. In some embodiments, biotinylated antibodies are linked to avidin particles, creating tetrameric complexes having four antibody molecules per avidin molecule. In some embodiments, antibodies are bound to biotinylated agarose gel particles (One Cell Systems, Cambridge, Mass., U.S.A.) via biotin-avidin-biotinylated antibody linkages. Such particles typically are about 300-500 microns in size, and can be created in a sonicating water bath or in a rapidly mixed water bath.

Cell-substrate particles (i.e., particles including cells and substrate-bound antibodies) can sediment from solution as an agglutinate. Cell-substrate particles also can be removed from solution by, for example, an applied magnetic field, as when the particle is a paramagnetic bead. Substrate-bound antibodies typically are provided in a cell separation composition at a concentration between about 0.1 and about $50.0 \times 10^9$ particles/1 (e.g., between 0.25 to $10.0 \times 10^9$, 1 to $20.0 \times 10^9$, 2 to $10.0 \times 10^9$, 0.5 to $2 \times 10^9$, 2 to $5 \times 10^9$, 5 to $10 \times 10^9$, and 10 to $30 \times 10^9$ particles/1), where particles refers to solid phase particles having antibodies bound thereto.

Cell separation compositions also can contain divalent cations (e.g., $Ca^{+2}$ and $Mg^{+2}$). Divalent cations can be provided, for example, by a balanced salt solution (e.g., Hank's balanced salt solution). $Ca^{+2}$ ions reportedly are important for selectin-mediated and integrin-mediated cell-cell adherence.

Cell separation compositions also can contain an anticoagulant such as heparin. Heparin can prevent clotting and non-specific cell loss associated with clotting in a high calcium environment. Heparin also promotes platelet clumping. Clumped platelets can adhere to granulocytes and monocytes and thereby enhance heterotypic agglutination more so than single platelets. Heparin can be supplied as a heparin salt (e.g., sodium heparin, lithium heparin, or potassium heparin).

Populations and Clonal Lines of MLPC

MLPC can be purified from human fetal blood using a cell separation composition described above. As used herein, "purified" means that at least 90% (e.g., 91, 92, 93, 94, 95, 96, 97, 98, or 99%) of the cells within the population are MLPC. As used herein, "MLPC" refers to fetal blood cells that are positive for CD9 and typically display a constellation of other markers such as CD13, CD73, and CD105. "MLPC population" refers to the primary culture obtained from the human fetal blood and uncloned progeny thereof. "Clonal line" refers to a cell line derived from a single cell. As used herein, a "cell line" is a population of cells able to renew themselves for extended periods of times in vitro under appropriate culture conditions. The term "line," however, does not indicate that the cells can be propagated indefinitely. Rather, clonal lines described herein typically can undergo 75 to 100 doublings before senescing.

Typically, an MLPC population is obtained by contacting a fetal blood sample with a cell separation composition described above and allowing the sample to partition into an agglutinate and a supernatant phase. For example, the sample can be allowed to settle by gravity or by centrifugation. Preferably, MLPC are purified from an umbilical cord blood sample that is less than 48 hours old (e.g., less than 24, 12, 8, or 4 hours post-partum). After agglutination, unagglutinated cells can be recovered from the supernatant phase. For example, cells in the supernatant phase can be recovered by centrifugation then washed with a saline solution and plated on a solid substrate (e.g., a plastic culture device such as a chambered slide or culture flask), using a standard growth medium with 10% serum (e.g., DMEM with 10% serum; RPMI-1640 with 10% serum, or mesenchymal stem cell growth medium with 10% serum (catalog #PT-3001, Cambrex, Walkersville, Md.). MLPC attach to the surface of the solid substrate while other cells, including T cells, NK cells and $CD34^+$ HSC, do not and can be removed with washing. The MLPC change from the leukocyte morphology to the fibroblastic morphology between 3 days and 2 weeks post initiation of culture after which the cells enter logarithmic growth phase and will continue growing logarithmically as long as cultures are maintained at cell concentrations of less than about $1.5 \times 10^5$ cells/$cm^2$. In some of the example herein, this is referred to as a "mixed cell line."

Clonal lines can be established by harvesting the MLPC then diluting and re-plating the cells on a multi-well culture plate such that a single cell can be found in a well. Cells can be transferred to a larger culture flask after a concentration of 1 to $5 \times 10^5$ cells/75 $cm^2$ is reached. Cells can be maintained at a concentration between $1 \times 10^5$ and $5 \times 10^5$ cells/75 $cm^2$ for logarithmic growth. See, e.g., U.S. Patent Publication No. 2005-0255592-A.

MLPC can be assessed for viability, proliferation potential, and longevity using techniques known in the art. For example, viability can be assessed using trypan blue exclusion assays, fluorescein diacetate uptake assays, or propidium iodide uptake assays. Proliferation can be assessed using thymidine uptake assays or MTT cell proliferation assays. Longevity can be assessed by determining the maximum number of population doublings of an extended culture.

MLPC can be immunophenotypically characterized using known techniques. For example, the cell culture medium can be removed from the tissue culture device and the adherent cells washed with a balanced salt solution (e.g., Hank's balanced salt solution) and bovine serum albumin (e.g., 2% BSA). Cells can be incubated with an antibody having binding affinity for a cell surface antigen such as CD9, CD45, CD13, C73, CD105, or any other cell surface antigen. The antibody can be detectably labeled (e.g., fluorescently or enzymatically) or can be detected using a secondary antibody that is detectably labeled. Alternatively, the cell surface antigens on MLPC can be characterized using flow cytometry and fluorescently labeled antibodies.

As described herein, the cell surface antigens present on MLPC can vary, depending on the stage of culture. Early in culture when MLPC display a leukocyte-like morphology, MLPC are positive for CD9 and CD45, SSEA-4 (stage-specific embryonic antigen-4), CD34, as well as CD13, CD29, CD44, CD73, CD90, CD105, stem cell factor, STRO-1 (a cell surface antigen expressed by bone marrow stromal cells), SSEA-3 (galactosylgloboside), and CD133, and are negative for CD15, CD38, glycophorin A (CD235a), and lineage markers CD2, CD3, CD4, CD5, CD7, CD8, CD10, CD11b, CD16, CD19, CD20, CD21, CD22, CD33, CD36, CD41, CD61, CD62E, CD72, HLA-DR, and CD102. After transition to the fibroblastic morphology, MLPC remain positive for CD9, CD13, CD29, CD73, CD90, and CD105, and become negative for CD34, CD41, CD45, stem cell factor, STRO-1, SSEA-3, SSEA-4, and CD133. At all times during in vitro culture, the undifferentiated MLPC are negative for CD15, CD38, glycophorin A (CD235a), and lineage markers CD2, CD3, CD4, CD5, CD7, CD8, CD10, CD11b, CD16, CD19, CD20, CD21, CD22, CD33, CD36, CD41, CD61, CD62E, CD72, HLA-DR, and CD102.

Bone marrow-derived MSC and MAPC as well as the cord blood-derived USSC have been described as being derived from a CD45⁻/CD34⁻ cell population. MLPC are distinguished from those cell types as being a CD45⁺/CD34⁺ derived cell. Additionally, the presence and persistence of CD9 on the fetal blood-derived MLPC at all stages of maturation further distinguishes MLPC from MSC and MAPC, which do not possess CD9 as a marker. CD9 is expressed as a marker on human embryonic stem cells. MLPC, which share the hematopoietic markers CD45, CD133, CD90 and CD34 during their leukocyte morphology phase, can be distinguished from HSC by their obligate plastic adherence and the presence of mesenchymal associated markers CD105, CD29, CD73, CD13 and embryonic associated markers SSEA-3 and SSEA-4. Additionally using currently available technology, HSC are unable to be cultured in vitro without further differentiation while MLPC can be expanded for many generations without differentiation. MLPC also differ from MSC and USSC by their more gracile in vitro culture appearance, thread-like cytoplasmic projections and their preference for low density culture conditions for optimal growth.

MLPC also can be characterized based on the expression of one or more genes. Methods for detecting gene expression can include, for example, measuring levels of the mRNA or protein of interest (e.g., by Northern blotting, reverse-transcriptase (RT)-PCR, microarray analysis, Western blotting, ELISA, or immunohistochemical staining). The gene expression profile of MLPC is significantly different than other cell types. Microarray analysis indicated that the MLPC lines have an immature phenotype that differs from the phenotypes of, for example, CD133+HSC, lineage negative cells (Forrz et al., $Stem\ Cells$, 22(1):100-108 (2004)), and MSC (catalog #PT-2501, Cambrex, Walkersville, Md., U.S. Pat. No. 5,486, 359), which demonstrate a significant degree of commitment down several lineage pathways.

Comparison of the gene expression profile of MLPC and MSC demonstrates MSC are more committed to connective tissue pathways. There are 80 genes up-regulated in MSC, and 152 genes up-regulated in MLPC. In particular, the following genes were up-regulated in MLPC when compared with MSC, i.e., expression was decreased in MSC relative to MLPC: ITGB2, ARHGAP9, CXCR4, INTEGRINB7, PECAM1, PRKCB_1, PRKCB_3, IL7R, AIF1, CD45_EX10-11, PLCG2, CD37, PRKCB_2, TCF2_1, RNF138, EAAT4, EPHA1, RPLP0, PTTG, SERPINA1_2, ITGAX, CD24, F11RPL4, ICAM1, LMO2, HMGB2, CD38, RPL7A, BMP3, PTHR2, S100B, OSF, SNCA, GRIK1, HTR4, CHRM1, CDKN2D, HNRPA1, IL6R, MUSLAMR, ICAM2, CSK, ITGA6, MMP9, DNMT1, PAK1, IKKB, TFRC_MIDDLE, CHI3L2, ITGA4, FGF20, NBR2, TNFRSF1B, CEBPA_3, CDO1, NFKB1, GATA2, PDGFRB, ICSBP1, KCNE3, TNNC1, ITGA2B, CCT8, LEFTA, TH, RPS24, HTR1F, TREM1, CCNB2, SELL, CD34, HMGIY, COX7A2, SELE, TNNT2, SEM2, CHEK1, CLCN5, F5, PRKCQ, ITGAL, NCAM2, ZNF257-MGC12518-ZNF92-ZNF43-ZNF273-FLJ90430, CDK1, RPL6, RPL24, IGHA1-IGHA2_M, PUM2, GJA7, HTR7, PTHR1, MAPK14, MSI2_1, KCNJ3, CD133, SYP, TFRC_5PRIME, TDGF1-TDGF3_2, FLT3, HPRT, SEMA4D, ITGAM, KIAA0152_3, ZFP42, SOX20, FLJ21190, CPN2, POU2F2, CASP8_1, CLDN10, TREM2, TERT, OLIG1, EGR2, CD44_EX3-5, CD33, CNTFR, OPN, COL9A1_2, ROBO4, HTR1D_1, IKKA, KIT, NPPA, PRKCH, FGF4, CD68, NUMB, NRG3, SALL2, NOP5, HNF4G, FIBROMODULIN, CD58, CALB1, GJB5, GJA5, POU5F_1, GDF5, POU6F1, CD44_EX16-20, BCAN, PTEN1-PTEN2, AGRIN, ALB, KCNQ4, DPPA5, EPHB2, TGFBR2, and ITGA3. See, e.g., U.S. Patent Publication No. 2006-0040392-A1.

MLPC express a number of genes associated with "stemness," which refers to the ability to self-renew undifferentiated and ability to differentiate into a number of different cell types. Genes associated with "stemness" include the genes known to be over-expressed in human embryonic stem cells, including, for example, POU5F (October 4), TERT, and ZFP42. For example, 65 genes associated with protein synthesis are down-regulated, 18 genes linked with phosphate metabolism are down-regulated, 123 genes regulating proliferation and cell cycling are down-regulated, 12 different gene clusters associated with differentiation surface markers are down-regulated, e.g., genes associated with connective tissue, including integrin alpha-F, laminin and collagen receptor, ASPIC, thrombospondins, endothelium endothelin-1 and -2 precursors, epidermal CRABP-2, and genes associated with adipocytes, including, for example, the leptin receptor, and 80 genes linked to nucleic acid binding and regulation of differentiation are up-regulated. Thus, the immaturity of a population of MLPC can be characterized based on the expression of one or more genes (e.g., one or more of CXCR4, FLT3, TERT, KIT, POU5F, or hematopoietic CD markers such as CD9, CD34, and CD133). See, e.g., U.S. Patent Publication No. 2006-0040392-A1.

MLPC can be cryopreserved by suspending the cells (e.g. $5 \times 10^6$ to $2 \times 10^7$ cells/mL) in a cryopreservative such as dimethylsulfoxide (DMSO, typically 1 to 10%) or in fetal bovine serum, human serum, or human serum albumin in combination with one or more of DMSO, trehalose, and dextran. For example, (1) fetal bovine serum containing 10% DMSO; (2) human serum containing 10% DMSO and 1% Dextran; (3) human serum containing 1% DMSO and 5% trehalose; or (4) 20% human serum albumin, 1% DMSO, and 5% trehalose can be used to cryopreserve MLPC. After adding cryopreservative, the cells can be frozen (e.g., to −90° C.). In some embodiments, the cells are frozen at a controlled rate (e.g., controlled electronically or by suspending the cells in a bath of 70% ethanol and placed in the vapor phase of a liquid nitrogen storage tank. When the cells are chilled to −90° C., they can be placed in the liquid phase of the liquid nitrogen storage tank for long term storage. Cryopreservation can allow for long-term storage of these cells for therapeutic use.

Differentiation of MLPC

MLPC are capable of differentiating into a variety of cells, including cells of each of the three embryonic germ layers (i.e., endoderm, ectoderm, and mesoderm). As used herein, "capable of differentiating" means that a given cell, or its progeny, can proceed to a differentiated phenotype under the appropriate culture conditions. For example, MLPC can differentiate into cells having an osteocytic phenotype, cells having an adipocytic phenotype, cells having a neurocytic phenotype, cells having a myocytic phenotype, cells having an endothelial phenotype, cells having a hepatocytic/pancreatic precursor phenotype (also known as an oval cell), cells having a respiratory epithelial cell phenotype, as well as other cell types. A clonal population of differentiated cells (e.g., cells having a respiratory epithelial cell phenotype) is obtained when a clonal line of MLPC is differentiated.

Differentiation can be induced using one or more differentiation agents, including without limitation, $Ca^{2+}$, an epidermal growth factor (EGF), a platelet derived growth factor (PDGF), a keratinocyte growth factor (KGF), a transforming growth factor (TGF), cytokines such as an interleukin, an interferon, or tumor necrosis factor, retinoic acid, transferrin, hormones (e.g., androgen, estrogen, insulin, prolactin, triiodothyronine, hydrocortisone, or dexamethasone), sodium butyrate, TPA, DMSO, NMF (N-methyl formamide), DMF (dimethylformamide), or matrix elements such as collagen, laminin, heparan sulfate).

Determination that an MLPC has differentiated into a particular cell type can be assessed using known methods, including, measuring changes in morphology and cell surface markers (e.g., by flow cytometry or immunohistochemistry), examining morphology by light or confocal microscopy, or by measuring changes in gene expression using techniques such as polymerase chain reaction (PCR) or gene-expression profiling.

For example, MLPC can be induced to differentiate into cells having an osteocytic phenotype using an induction medium (e.g., Osteogenic Differentiation Medium, catalog #PT-3002, from Cambrex) containing dexamethasone, L-glutamine, ascorbate, and β-glycerophosphate (Jaiswal et al., *J. Biol. Chem.* 64(2):295-312 (1997)). Cells having an osteocytic phenotype contain deposits of calcium crystals, which can be visualized, for example, using Alizarin red stain.

MLPC can be induced to differentiate into cells having an adipocytic phenotype using an induction medium (e.g., Adipogenic Differentiation Medium, catalog #PT-3004, from Cambrex) containing insulin, L-glutamine, dexamethasone, indomethacin, and 3-isobutyl-1-methyl-xanthine. Cells having an adipocytic phenotype contain lipid filled liposomes that can be visualized with Oil Red stain. Such cells also contain trigycerides, which fluoresce green with Nile Red stain (Fowler and Greenspan, *Histochem. Cytochem.* 33:833-836 (1985)).

MLPC can be induced to differentiate into cells having a myocytic phenotype using an induction medium (e.g., SkGM™, catalog #CC-3160, from Cambrex) containing EGF, insulin, Fetuin, dexamethasone, and FGF-basic (Wernet, et al., U.S. patent publication 20020164794 A1). Cells having a myocytic phenotype express fast skeletal muscle myosin and alpha actinin.

MLPC can be induced to differentiate into cells having a neural stem cell phenotype (neurospheres) using an induction medium (e.g., NPMM™—Neural Progenitor Maintenance medium, catalog #CC-3209, from Cambrex) containing human FGF-basic, human EGF, NSF-1, and FGF-4 and a culture device pre-coated with poly-D-lysine and laminin (e.g., from BD Biosciences Discovery Labware, catalog #354688). Once cells have been differentiated into neurospheres, they can be further differentiated into motor neurons with the addition of brain-derived neurotrophic factor (BDNF) and neurotrophin-3 (NT-3), astrocytes with the addition of leukemia inhibitory factor (LIF), retinoic acid and ciliary neurotrophic factor, and oligodendrocytes with the addition of 3,3',5-triiodo-L-thyronine (T3). Neurocytic differentiation can be confirmed by the expression of nestin, class III beta-tubulin (tubulin β-4), glial fibrillary acidic protein (GFAP), and galactocerebroside (GalC). Neurospheres are positive for all such markers while some differentiated cell types are not. Differentiation into oligodendrocytes can be confirmed by positive staining for myelin basic protein (MBP).

MLPC can be induced to differentiate into cells having an endothelial phenotype using an endothelial growth medium (e.g., EGM™-MV, catalog #CC-3125, from Cambrex) containing heparin, bovine brain extract, epithelial growth factor (e.g., human recombinant epithelial growth factor), and hydrocortisone. Endothelial differentiation can be confirmed by expression of E-selectin (CD62E), ICAM-2 (CD102), CD34, and STRO-1.

MLPC can be induced to differentiate into cells having a hepatocyte/pancreatic precursor cell phenotype using an induction medium (e.g., HCM™—hepatocyte culture medium, catalog #CC-3198, from Cambrex) containing ascorbic acid, hydrocortisone, transferrin, insulin, EGF, hepatocyte growth factor, FGF-basic, fibroblast growth factor-4, and stem cell factor. Liver and pancreas cells share a common progenitor. Hepatocyte differentiation can be confirmed by expression of hepatocyte growth factor and human serum albumin. Pancreatic cell differentiation can be confirmed by production of insulin and pro-insulin.

MLPC can be induced to differentiate into cells having a respiratory epithelium phenotype. For example, MLPC can be induced to differentiate into type II alveolar cells, which also are known as type II pneumocytes. A medium can be used that contains one or more of pituitary extract (e.g. a bovine pituitary extract), steroid hormones (e.g. hydrocortisone, or a salt thereof such as the acetate), growth factors (e.g., epidermal growth factor, preferably human epidermal growth factor), catecholamines (e.g., epinephrine, either in racemic or enantiomeric form), iron-binding proteins (e.g., a transferrin), insulin, vitamins (e.g., retinoic acid), thyroid hormones (e.g., triiodothyronine), serum albumins (e.g., bovine or human serum albumin, including recombinant preparations), antibiotics (e.g., aminoglycoside antibiotics, such as gentamicin), and/or antifingals (e.g. amphotericin-B). For example, a medium can include hydrocortisone, epidermal growth factor, insulin, triiodothyronine, transferrin, and bovine serum albumin and in some embodiments, further can include retinoic acid, pituitary extract, and epinephrine. SAGM™ medium from Cambrex (catalog CC-3118) is particularly useful for differentiating MLPC into type II alveolar cells. Differentiation to respiratory epithelial cells (e.g., type II alveolar cells) can be confirmed, for example, by an epithelioid morphology as assessed by light microscopy and the presence of lamellar bodies and microvesicular bodies as assessed by transmission electron microscopy. Lamellar bodies are secretory lysosomes that serve as the storage form of lung surfactant, surfactant protein C (SPC), which is an integral membrane protein that is expressed only in type II alveolar cells. The presence of SPC mRNA can be detected by reverse-transcriptase PCR and the presence of SPC protein can be detected by immunofluorescence staining. Clonal populations of respiratory epithelial cells (i.e., a plurality of respiratory epithelial cells obtained from a clonal line of MLPC) are particularly useful, for example, in terminal airway models, chronic airway disease (e.g., COPD), lung injury (including injury induced by therapeutic means such as adiation for various diseases/illnesses), surfactant deficiency, alpha-1 anti-trypsin deficiency, and cystic fibrosis.

Modified Populations of MLPC

MLPC can be modified such that the cells can produce one or more polypeptides or other therapeutic compounds of interest. To modify the isolated cells such that a polypeptide or other therapeutic compound of interest is produced, the appropriate exogenous nucleic acid must be delivered to the cells. In some embodiments, the cells are transiently transfected, which indicates that the exogenous nucleic acid is episomal (i.e., not integrated into the chromosomal DNA). In other embodiments, the cells are stably transfected, i.e., the exogenous nucleic acid is integrated into the host cell's chromosomal DNA. The term "exogenous" as used herein with reference to a nucleic acid and a particular cell refers to any nucleic acid that does not originate from that particular cell as found in nature. In addition, the term "exogenous" includes a naturally occurring nucleic acid. For example, a nucleic acid encoding a polypeptide that is isolated from a human cell is an exogenous nucleic acid with respect to a second human cell once that nucleic acid is introduced into the second human cell. The exogenous nucleic acid that is delivered typically is part of a vector in which a regulatory element such as a promoter is operably linked to the nucleic acid of interest.

Cells can be engineered using a viral vector such as an adenovirus, adeno-associated virus (AAV), retrovirus, lentivirus, vaccinia virus, measles viruses, herpes viruses, or bovine papilloma virus vector. See, Kay et al. (1997) *Proc. Natl. Acad. Sci. USA* 94:12744-12746 for a review of viral and non-viral vectors. A vector also can be introduced using mechanical means such as liposomal or chemical mediated uptake of the DNA. For example, a vector can be introduced into an MLPC by methods known in the art, including, for example, transfection, transformation, transduction, electroporation, infection, microinjection, cell fusion, DEAE dextran, calcium phosphate precipitation, liposomes, LIPO-FECTIN™, lysosome fusion, synthetic cationic lipids, use of a gene gun or a DNA vector transporter.

A vector can include a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture.

MLPC also can have a targeted gene modification. Homologous recombination methods for introducing targeted gene modifications are known in the art. To create a homologous recombinant MLPC, a homologous recombination vector can be prepared in which a gene of interest is flanked at its 5' and 3' ends by gene sequences that are endogenous to the genome of the targeted cell, to allow for homologous recombination to occur between the gene of interest carried by the vector and the endogenous gene in the genome of the targeted cell. The additional flanking nucleic acid sequences are of sufficient length for successful homologous recombination with the endogenous gene in the genome of the targeted cell. Typically, several kilobases of flanking DNA (both at the 5' and 3' ends) are included in the vector. Methods for constructing homologous recombination vectors and homologous recombinant animals from recombinant stem cells are commonly known in the art (see, e.g., Thomas and Capecehi, 1987, *Cell* 51:503; Bradley, 1991, *Curr. Opin. Bio/Technol.* 2:823-29; and PCT Publication Nos. WO 90/11354, WO 91/01140, and WO 93/04169.

Methods of Using MLPC

The MLPC can be used in enzyme replacement therapy to treat specific diseases or conditions, including, but not limited to lysosomal storage diseases, such as Tay-Sachs, Niemann-Pick, Fabry's, Gaucher's, Hunter's, and Hurler's syndromes, as well as other gangliosidoses, mucopolysaccharidoses, and glycogenoses.

In other embodiments, the cells can be used as carriers in gene therapy to correct inborn errors of metabolism, adrenoleukodystrophy, cystic fibrosis, glycogen storage disease, hypothyroidism, sickle cell anemia, Pearson syndrome, Pompe's disease, phenylketonuria (PKIJ), porphyrias, maple syrup urine disease, homocystinuria, mucoplysaccharidenosis, chronic granulomatous disease and tyrosinemia and Tay-Sachs disease or to treat cancer, tumors or other pathological conditions.

MLPC can be used to repair damage of tissues and organs resulting from disease. In such an embodiment, a patient can be administered a population of MLPC to regenerate or restore tissues or organs which have been damaged as a consequence of disease. For example, a population of MLPC can be administered to a patient to enhance the immune system following chemotherapy or radiation, to repair heart tissue following myocardial infarction, or to repair lung tissue after lung injury or disease.

The cells also can be used in tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

MLPC also can be used in therapeutic transplantation protocols, e.g., to augment or replace stem or progenitor cells of the liver, pancreas, kidney, lung, nervous system, muscular system, bone, bone marrow, thymus, spleen, mucosal tissue, gonads, or hair.

Compositions and Articles of Manufacture

The invention also features compositions and articles of manufacture containing purified populations of MLPC or clonal lines of MLPC. In some embodiments, the purified population of MLPC or clonal line is housed within a container (e.g., a vial or bag). In some embodiments, the clonal lines have undergone at least 3 doublings in culture (e.g., at least 4, 5, 6, 7, 8, 9, 10, 15, 20, 25, 30, 35, 40, 45, or 50 doublings). In other embodiments, a culture medium (e.g., MSCGM™ medium or SAGM™) is included in the composition or article of manufacture. In some embodiments, the composition includes a mixed population of cells. For example, the composition can include MLPC and cells having a respiratory epithelial cell phenotype. In still other embodiments, the composition or article of manufacture can include one or more cryopreservatives or pharmaceutically acceptable carriers. For example, a composition can include serum and DMSO, a mixture of serum, DMSO, and trehalose, or a mixture of human serum albumin, DMSO, and trehalose.

Purified populations of MLPC or clonal MLPC lines can be combined with packaging material and sold as a kit. For example, a kit can include purified populations of MLPC or clone MLPC lines and a differentiation medium effective to induce differentiation of the MLPC into cells having a respiratory epithelial cell phenotype. The differentiation medium can include hydrocortisone, epidermal growth factor, insulin, triiodothyronine, transferrin, and bovine serum albumin, and in some embodiments, further include retinoic acid, pituitary extract, epinephrine, and/or an antibiotic. The packaging material included in a kit typically contains instructions or a label describing how the purified populations of MLPC or clonal lines can be grown, differentiated, or used. A label also can indicate that the MLPC have enhanced expression of, for example, CXCR4, FLT3, or CD133 relative to a population of MSC. Components and methods for producing such kits are well known.

In other embodiments, an article of manufacture or kit can include differentiated progeny of MLPC or differentiated progeny of clonal MLPC lines. For example, an article of manufacture or kit can include a clonal population of cells having a respiratory epithelial phenotype (e.g., type II alveolar cells) and a culture medium, and further can include one or more cryopreservatives. In some embodiments, the clonal population of cells is housed within a container such as a vial or bag.

An article of manufacture or kit also can include one or more reagents for characterizing a population of MLPC, a clonal MLPC line, or differentiated progeny of MLPC. For example, a reagent can be a nucleic acid probe or primer for detecting expression of a gene such as CXCR4, FLT3, CD133, CD34, TERT, KIT, POU5F, ICAM2, ITGAX, TFRC, KIT, IL6R, IL7R, ITGAM, FLT3, PDGFRB, SELE, SELL, TFRC, ITGAL, ITGB2, PECAM1, ITGA2B, ITGA3, ITGA4, ITGA6, ICAM1, CD24, CD44, CD45, CD58, CD68, CD33, CD37, or CD38. Such a nucleic acid probe or primer can be labeled, (e.g., fluorescently or with a radioisotope) to facilitate detection. A reagent also can be an antibody having specific binding affinity for a cell surface marker such as CD9, CD45, SSEA-4, CD34, CD13, CD29, CD41, CD44, CD73, CD90, CD105, stem cell factor, STRO-1, SSEA-3, CD133, CD15, CD38, glycophorin A (CD235a), CD2, CD3, CD4, CD5, CD7, CD8, CD10, CD11b, CD13, CD16, CD19, CD20, CD21, CD22, CD29, CD33, CD36, CD41, CD61, CD62E, CD72, CD73, CD90, HLA-DR, CD102, CD105, or a membrane protein such as prosurfactant protein C or surfactant protein C. An antibody can be detectably labeled (e.g., fluorescently or enzymatically).

The invention is further described in the following examples, which do not limit the scope of the invention described in the claims.

EXAMPLES

Example 1

Separating Blood Cells

This example describes the general method by which cells were separated using the cell separation reagents described below. Equal volumes of a cell separation reagent (see Table 1) and an acid citrate dextrose (ACD), CPDA (citrate, phosphate, dextrose, adenine) or heparinized umbilical cord blood sample were combined (25 ml each) in a sterile closed container (e.g., a 50 ml conical tube). Samples containing white blood cell counts greater than $20 \times 10^6$ cells/ml were combined one part blood with two parts cell separation reagent. Tubes were gently mixed on a rocker platform for 20 to 45 minutes at room temperature. Tubes were stood upright in a rack for 30 to 50 minutes to permit agglutinated cells to partition away from unagglutinated cells, which remained in solution. A pipette was used to recover unagglutinated cells from the supernatant without disturbing the agglutinate. Recovered cells were washed in 25 ml PBS and centrifuged at 500×g for 7 minutes. The cell pellet was resuspended in 4 ml PBS+2% human serum albumin.

TABLE 1

| Cell Separation Reagent | |
|---|---|
| Dextran (average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone 2.2.2.E7) | 0.1-15 mg/L (preferably about 0.25 mg/L) |
| Anti-CD15 (murine IgM monoclonal antibody, clone 324.3.B9) | 0.1-15 mg/L (preferably about 2.0 mg/L) |
| Anti-CD9 (murine IgM monoclonal antibody, clone 8.10.E7) | 0.1-15 mg/L (preferably about 2.0 mg/L) |

Cells also were recovered from the agglutinate using a hypotonic lysing solution containing EDTA and ethylene glycol-bis(2-aminoethylether)-N,N,N',N'-tetraacetic acid (EGTA). Agglutinated cells were treated with 25 ml VitaLyse® (BioE, St. Paul, Minn.) and vortexed. After 10 minutes, cells were centrifuged at 500×g for 7 minutes and the supernatant was removed. Cells were resuspended in 4 ml PBS.

Recoveries of erythrocytes, leukocytes, lymphocytes, monocytes, granulocytes, T cells, B cells, NK cells, hematopoietic stem cells, and non-hematopoietic stem cells were determined by standard flow cytometry and immunophenotyping. Prior to flow cytometry, leukocyte recovery (i.e., white blood cell count) was determined using a Coulter Onyx Hematology Analyzer. Cell types were identified and enumerated by combining hematology analysis with flow cytometry analysis, identifying cells on the basis of light scattering properties and staining by labeled antibodies.

As shown in Table 2, 99.9% of erythrocytes were removed, 99.8% monocytes and granulocytes, 74% of B cells, 64.9% of NK cells, and 99.4% of the platelets were removed from the cord blood.

TABLE 2

| | Recovery of Cells | |
|---|---|---|
| | Before separation | After separation |
| Erythrocytes per ml | $4.41 \times 10^9$ | $0.006 \times 10^9$ |
| Leukocytes per ml | $5.9 \times 10^6$ | $1.53 \times 10^6$ |
| Lymphocytes (%) | 28.7 | 99.0 |
| Monocytes (%) | 8.69 | 0.12 |
| Granulocytes (%) | 62.5 | .083 |
| T Cells (CD3+) | 19.7 | 83.2 |
| B Cells (CD19+) | 4.46 | 8.10 |
| NK Cells (CD16+) | 3.15 | 8.43 |
| Platelets per ml | $226 \times 10^6$ | $1.4 \times 10^6$ |

Example 2

Purification of MLPC

The cell separation reagent of Table 3 was used to isolate MLPC from the non-agglutinated supernatant phase. See FIG. 1 for a schematic of the purification.

TABLE 3

| Cell Separation Reagent | |
|---|---|
| Dextran (average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone 2.2.2.E7) | 0.1-15 mg/L (preferably about 0.25 mg/L) |
| Anti-CD15 (murine IgM monoclonal antibody, clone 324.3.B9) | 0.1-15 mg/L (preferably about 2.0 mg/L) |
| Anti-CD9 (murine IgM monoclonal antibody, clone 8.10.E7) | 0.1-15 mg/L (preferably about 2.0 mg/L) |

Briefly, 50-150 ml of CPDA anti-coagulated umbilical cord blood (<48 hours old) was gently mixed with an equal volume of cell separation composition described in Table 3 for 30 minutes. After mixing was complete, the container holding the blood/cell separation composition mixture was placed in an upright position and the contents allowed to settle by normal 1×g gravity for 30 minutes. After settling was complete, the non-agglutinated cells were collected from the supernatant. The cells were recovered from the supernatant by centrifugation then washed with PBS. Cells were resuspended in complete MSCGM™ (Mesenchymal stem cell growth medium, catalog #PT-3001, Cambrex, Walkersville, Md.) and adjusted to 2-9×10⁶ cells/ml with complete MSCGM™. Cells were plated in a standard plastic tissue culture flask (e.g., Corning), chambered slide, or other culture device and allowed to incubate overnight at 37° C. in a 5% $CO_2$ humidified atmosphere. All subsequent incubations were performed at 37° C. in a 5% $CO_2$ humidified atmosphere unless otherwise noted. MLPC attached to the plastic during this initial incubation. Non-adherent cells (T-cells, NK-cells and CD34+ hematopoietic stem cells) were removed by vigorous washing of the flask or well with complete MSCGM™.

MLPC cultures were fed periodically by removal of the complete MSCGM™ and addition of fresh complete MSCGM™. Cells were maintained at concentrations of $1×10^5$-$1×10^6$ cells/75 cm² by this method. When cell cultures reached a concentration of $8×10^5$-$1×10^6$ cells/75 cm², cells were cryopreserved using 10% DMSO and 90% serum or expanded into new flasks. Cells were recovered from the adherent cultures by removal of the complete MSCGM™ and replacement with PBS+0.1% EGTA. Cells were incubated for 15-60 minutes at 37° C. then collected from the flask and washed in complete MSCGM™. Cells were then replated at $1×10^5$ cells/mL. Cultures that were allowed to achieve confluency were found to have diminished capacity for both proliferation and differentiation. Subsequent to this finding, cultures were not allowed to achieve higher densities than $1×10^6$ cells/75 cm².

Example 3

Morphology of MLPC and Development to Fibroblastic Morphology

Cord blood derived MLPC isolated and cultured according to Examples 1 and 2 were cultured in standard MSCGM™ until confluency. Depending on the donor, MLPC cultures achieved confluency in 2-8 weeks. The morphology of these cells during growth and cultural maturation is shown in FIG. 2A-2D.

Figure 2C:
Figure 2D:
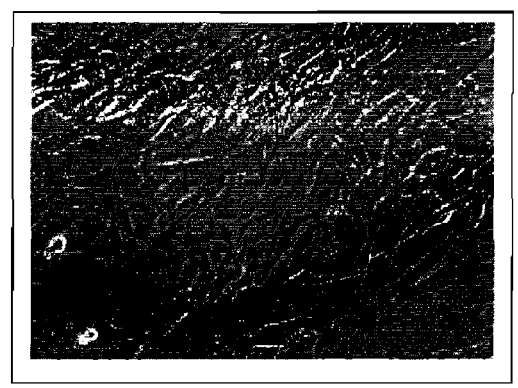

In the early stage shown in FIG. 2A, the cells are dividing very slowly and resemble circulating leukocytes but with dendritic cytoplasmic extensions. Many cells still exhibit the small round cell morphology that these cells would exhibit in circulation. As culture continues, the leukocyte-like cells start to change their morphology from the leukocyte-like appearance to a flatter, darker more fibroblast-like appearance (see FIG. 2B). When cells are dividing, they round up, divide, and then reattach to the culture vessel surface and spread out again. This slowly continues until the cells fill the available surface. FIG. 2C shows the morphology of cell cultures during logarithmic growth. FIG. 2D shows the morphology of a fully confluent culture of MLPC. With the exception of the two cells in active division seen in the lower left corner of the picture, all of the cells have a fibroblast-like morphology.

In summary, early during culture, cells appeared small and round, but had cytoplasmic projections, both finger-like and highly elongate projections, which help distinguish them from the other blood cells. Shortly after the initiation of the culture, the cells began to spread and flatten, taking on a morphology consistent with fibroblasts. Eventually, upon confluency, the cells grew in largely parallel orientation. Repeated growth of cultures to confluency resulted in their having diminished proliferation and differentiating capacity.

Example 4

Immunophenotyping of Cells by Immunofluorescent Microscopy

In order to determine the surface markers present on MLPC, freshly isolated cells were plated in 16 well chamber slides and grown to confluency. At various times during the culture (from 3 days post plating to post confluency), cells were harvested and stained for the following markers: CD45-FITC (BD/Pharmingen), CD34-PE (BD/Pharmingen), CD4-PE (BioE), CD8-PE (BioE), anti-HLA-DR-PE (BioE), CD41-PE (BioE), CD9-PE (Ancell), CD105-PE (Ancell), CD29-PE (Coulter), CD73-PE (BD/Pharmingen), CD90-PE (BD/Pharmingen), anti-hu Stem Cell Factor-FITC (R&D Systems), CD14-PE (BD/Pharmingen), CD15-FITC (Ancell), CD38-PE (BD/Pharmingen), CD2-PE (BD/Pharmingen), CD3-FITC (BD/Pharmingen), CD5-PE (BD/Pharmingen), CD7-PE (BD/Pharmingen), CD16-PE (BD/Pharmingen), CD20-FITC (BD/Pharmingen), CD22-FITC (BD/Pharmingen), CD19-PE (BD/Pharmingen), CD33-PE (BD/Pharmingen), CD10-FITC (BD/Pharmingen), CD61-FITC (BD/Pharmingen), CD133-PE (R&D Systems), anti-STRO-1 (R&D Systems) and Goat anti-mouse IgG(H+L)-PE (BioE), SSEA-3 (R&D Systems) and goat anti-rat IgG (H+L)-PE (BioE), SSEA-4 (R&D Systems) and goat anti-mouse IgG(H+L)-PE (BioE). The cell surface markers also were assessed in bone marrow MSC (Cambrex, Walkersville, Md.) and cord blood HSC (obtained from the non-adherent cells described above).

Briefly, cell culture medium was removed from the wells and the cells were washed 3× with Hank's Balanced Salt Solution+2% BSA. Cells were then stained with the antibodies for 20 minutes in the dark at room temperature. After incubation, the cells were washed 3× with Hank's Balanced Salt Solution+2% BSA and the cells were directly observed for fluorescence by fluorescent microscopy. Results obtained comparing cord blood derived MLPC with bone marrow-derived MSC's and cord blood derived hematopoietic stem cells (HSC) are outlined in Table 4.

TABLE 4

| Cell Marker | Early MLPC (Leukocyte morphology) | Mature MLPC (Fibroblast morphology) | Cord Blood HSC | Bone Marrow MSC |
| --- | --- | --- | --- | --- |
| CD2 | Negative | Negative | Negative | Negative |
| CD3 | Negative | Negative | Negative | Negative |
| CD4 | Negative | Negative | Negative | Negative |
| CD5 | Negative | Negative | Negative | Negative |
| CD7 | Negative | Negative | Negative | Negative |
| CD8 | Negative | Negative | Negative | Negative |
| CD9 | Positive | Positive | Negative | Negative |
| CD10 | Negative | Negative | Negative | Negative |
| CD13 | Positive | Positive | Negative | Positive |
| CD14 | Negative | Negative | Negative | Negative |
| CD15 | Negative | Negative | Negative | Negative |
| CD16 | Negative | Negative | Negative | Negative |
| CD19 | Negative | Negative | Negative | Negative |
| CD20 | Negative | Negative | Negative | Negative |
| CD22 | Negative | Negative | Negative | Negative |
| CD29 | Positive | Positive | Positive | Positive |
| CD33 | Negative | Negative | Variable | Negative |
| CD34 | Positive | Negative | Positive | Negative |
| CD36 | Negative | Negative | Negative | Negative |
| CD38 | Negative | Negative | Variable | Negative |
| CD41 | Negative | Negative | Negative | Negative |

TABLE 4-continued

| Cell Marker | Early MLPC (Leukocyte morphology) | Mature MLPC (Fibroblast morphology) | Cord Blood HSC | Bone Marrow MSC |
|---|---|---|---|---|
| CD45 | Positive | Negative | Positive | Negative |
| CD61 | Negative | Negative | Variable | Negative |
| CD73 | Positive | Positive | Negative | Positive |
| Anti-HLA-DR | Negative | Negative | Variable | Negative |
| CD90 | Positive | Positive | Positive | Positive |
| CD105 | Positive | Positive | Negative | Positive |
| STRO-1 | Positive | Negative | Negative | Negative |
| SSEA-3 | Positive | Negative | Negative | Negative |
| SSEA-4 | Positive | Negative | Negative | Negative |
| SCF | Positive | Negative | Negative | Negative |
| Glycophorin A | Negative | Negative | Negative | Negative |
| CD133 | Positive | Negative | Positive | Negative |

Example 5

Clonal MLPC Cell Lines

After the second passage of MLPC cultures from Example 2, the cells were detached from the plastic surface of the culture vessel by substituting PBS containing 0.1% EGTA (pH 7.3) for the cell culture medium. The cells were diluted to a concentration of 1.3 cells/ml in complete MSCGM™ and distributed into a 96 well culture plate at a volume of 0.2 ml/well, resulting in an average distribution of approximately 1 cell/3 wells. After allowing the cells to attach to the plate by overnight incubation at 37° C., the plate was scored for actual distribution. Only the wells with 1 cell/well were followed for growth. As the cells multiplied and achieved concentrations of $1$-$5 \times 10^5$ cells/75 cm$^2$, they were transferred to a larger culture vessel in order to maintain the cells at a concentration between $1 \times 10^5$ and $5 \times 10^5$ cells/75 cm$^2$ to maintain logarithmic growth. Cells were cultured at 37° C. in a 5% $CO_2$ atmosphere.

At least 52 clonal cell lines have been established using this procedure and were designated: UM081704-1-E2, UM081704-1-B6, UM081704-1-G11, UM081704-1-G9, UM081704-1-E9, UM081704-1-E11, UM081704-1-G8, UM081704-1-H3, UM081704-1-D6, UM081704-1-H11, UM081704-1-B4, UM081704-1-H4, UM081704-1-C2, UM081704-1-G1, UM081704-1-E10, UM081704-1-B7, UM081704-1-G4, UM081704-1-F12, UM081704-1-H1, UM081704-1-D3, UM081704-1-A2, UM081704-1-B11, UM081704-1-D5, UM081704-1-E4, UM081704-1-C10, UM081704-1-A5, UM081704-1-E8, UM081704-1-C12, UM081704-1-E5, UM081704-1-A12, UM081704-1-C5, UM081704-1-A4, UM081704-1-A3, MH091404-2#1-1.G10, UM093004-1-A3, UM093004-1-B7, UM093004-1-F2, UM093004-1-A12, UM093004-1-G11, UM093004-1-G4, UM093004-1-B12, UM093004-2-A6, UM093004-2-A9, UM093004-2-B9, UM093004-2-C5, UM093004-2-D12, UM093004-2-H3, UM093004-2-H11, UM093004-2-H4, UM093004-2-A5, UM093004-2-C3, and UM093004-2-C10. The surface markers of clonal cell line UM081704-1-E8 were assessed according to the procedure outlined in Example 4 and found to be the same as the "mature MLPC" having fibroblast morphology, as shown in Table 4.

Example 6

Osteocytic Differentiation of MLPC

A population of MLPC and clonal cell line UM081704-1-E8 each were cultured in complete MSCGM™ and grown under logarithmic growth conditions outlined above. Cells were harvested by treatment with PBS+0.1% EGTA and replated at $5 \times 10^3$ to $2 \times 10^4$/ml in complete MSCGM™. The cells were allowed to adhere overnight and then the medium was replaced with Osteogenic Differentiation Medium (catalog #PT-3002, Cambrex,) consisting of complete MSCGM™ supplemented with dexamethasone, L-glutamine, ascorbate, and β-glycerophosphate. Cells were cultured at 37° C. in a 5% $CO_2$ atmosphere and fed every 3-4 days for 2-3 weeks. Deposition of calcium crystals was demonstrated by using a modification of the Alizarin red procedure and observing red staining of calcium mineralization by phase contrast and fluorescent microscopy.

Example 7

Adipocytic Differentiation of MLPC

A population of MLPC and clonal cell line UM081704-1-E8 each were plated in complete MSCGM™ at a concentration of $1 \times 10^4$ to $2 \times 10^5$ cells/mL medium and cultured at 37° C. in a 5% $CO_2$ atmosphere. Cells were allowed to re-adhere to the culture plate and were fed every 3-4 days until the cultures reached confluency. At 100% confluency, cells were differentiated by culture in Adipogenesis differentiation medium (catalog #PT-3004, Cambrex) consisting of complete MSCGM™ supplemented with hu-insulin, L-glutamine, dexamethasone, indomethacin, and 3-isobutyl-1-methyl-xanthine, for at least 14 days.

To assess differentiation, the cells were stained with Oil Red stain specific for lipid. Confluent cultures of MLPC display a fibroblast-like morphology and do not display any evidence of liposome development as assessed by Oil Red staining. In contrast, MLPC differentiated with Adipogenic medium for 3 weeks exhibit liposomes that are characteristic of adipocytes (i.e., bright white vessels in cytoplasm) and that stain red with the Oil Red stain. MLPC differentiated with Adipogenic medium also fluoresce green with Nile Red stain specific for trigycerides. Undifferentiated cells retain their fibroblast-like morphology and do not stain.

Example 8

Myocytic Differentiation of MLPC

MLPC (both a population and clonal cell line UM081704-1-E8) were plated in complete MSCGM™ at a concentration of $1.9 \times 10^4$ cells/well within a 4-chamber fibronectin pre-coated slide and allowed to attach to the plate for 24-48 hr at 37° C. in a 5% $CO_2$ atmosphere. Medium was removed and replaced with 10 µM 5-azacytidine (catalog #A 1287, Sigma Chemical Co.) and incubated for 24 hours. Cells were washed twice with PBS and fed with SkGM™ Skeletal Muscle Cell Medium (catalog #CC-3160, Cambrex) containing recombinant human epidermal growth factor (huEGF), human insulin, Fetuin, dexamethasone, and recombinant human basic fibroblast growth factor (100 ng/mL) (huFGF-basic, catalog #F0291, Sigma Chemical Co., St. Louis, Mo.). Cells were fed every 2-3 days for approximately 21 days. Control wells were fed with MSCGM™ while experimental wells were fed with SkGM™ (as described above).

Cultures were harvested 7 days post initiation of myocytic culture. Culture supernatant was removed and cells were fixed for 2 hours with 2% buffered formalin. Cells were permeabilized with PermaCyte™ (BioE, St. Paul, Minn.) and stained with mouse monoclonal antibody specific for human fast skeletal myosin (MY-32, catalog #ab7784, Abcam, Cambridge, Mass.) or mouse monoclonal antibody specific for alpha actinin (BM 75.2, catalog #ab11008, Abcam). Cells were incubated with the primary antibody for 20 minutes, washed with PBS and counter stained with goat anti-mouse IgG (H+L)-PE (BioE, St. Paul, Minn.). The myocytic culture contained fast skeletal muscle myosin and alpha actinin, which is indicative of the transdifferentiation of MLPC to skeletal muscle cells.

Example 9

Neurocytic Differentiation of MLPC

Bone marrow derived hMSC (Cambrex), cord blood MLPC, and MLPC clonal cell line were grown under logarithmic growth conditions described above. Cells were harvested as described above and replated at $0.8 \times 10^4$ cells per chamber in 4-chamber slides that were pre-coated with poly-D-lysine and laminin (BD Biosciences Discovery Labware, catalog #354688) in 0.5 mL of NPMM™ (catalog #CC-3209, Cambrex) containing huFGF-basic, huEGF, brain-derived neurotrophic factor, neural survival factor-1, fibroblast growth factor-4 (20 ng/mL), and 200 mM GlutaMax I Supplement (catalog #35050-061, Invitrogen, Carlsbad, Calif.). The medium was changed every 2-3 days for 21 days. Neurospheres developed after 4 to 20 days. Transformation of MLPC to neural lineage was confirmed by positive staining for nestin (monoclonal anti-human nestin antibody, MAB1259, clone 196908, R&D Systems), class III beta-tubulin (tubulin b-4) (monoclonal anti-neuron-specific class III beta-tubulin antibody, MAB1195, Clone TuJ-1, R&D Systems), glial fibrillary acidic protein (GFAP) (monoclonal anti-human GFAP, HG2b-GF5, clone GF5, Advanced Immunochemical, Inc.), and galactocerebroside (GalC) (mouse anti-human GalC monoclonal antibody MAB342, clone mGalC, Chemicon).

Cells were further differentiated into neurons by the addition of 10 ng/mL BDNF (catalog #B3795, Sigma Chemical Co.) and 10 ng/mL NT3 (catalog #N1905, Sigma Chemical Co.) to the neural progenitor maintenance medium and further culturing for 10-14 days. Neurospheres were further differentiated into astrocytes by the addition of $10^{-6}$ M retinoic acid (catalog #R2625, Sigma Chemical Co.), 10 ng/mL LIF (catalog #L5158, Sigma Chemical Co.) and 10 ng/mL CNTF (catalog #C3710, Sigma Chemical Co.) to the neural progenitor maintenance medium and further culturing for 10-14 days. Neurospheres were further differentiated into oligodendrocytes by the addition of $10^{-6}$ M T3 (catalog #T5516, Sigma Chemical Co.) to the neural progenitor maintenance medium and further culturing for 10-14 days. Differentiation to oligodendrocytes was confirmed by positive staining for myelin basic protein (MBP) (monoclonal anti-MBP, catalog #ab8764, clone B505, Abcam).

Example 10

Endothelial Differentiation of MLPC

MLPC were plated at $1.9 \times 10^4$ cells per well within a 4-chamber slide (2 cm$^2$). Cells were fed with 1 ml of endothelial growth medium-microvasculature (FGM™-MV, catalog #CC-3125, Cambrex) containing heparin, bovine brain extract, human recombinant epithelial growth factor and hydrocortisone. The cells were fed by changing the medium every 2-3 days for approximately 21 days. Morphological changes occurred within 7-10 days. Differentiation of MLPC's to endothelial lineage was assessed by staining for CD62E [E-selectin, mouse anti-human CD62E monoclonal antibody, catalog #551145, clone 68-5H11, BD Pharmingen] and CD102 [ICAM-2, monoclonal anti-human ICAM-2, MAB244, clone 86911, R&D Systems], CD34 [BD Pharmingen] and STRO-1 (R&D Systems]. Control MLPC cultures grown in MSCGM for 14 days were negative for CD62E staining and CD 102, CD34 and STRO-1, while differentiated cultures were positive for both CD62E, CD102, CD34, and STRO-1.

Example 11

Differentiation of MLPC into Hepatocyte/Pancreatic Precursor Cells

MLPC were plated at a concentration of $1 \times 10^5$ cells/cm$^2$ in vitro in HCM™ medium (catalog #CC-3198, Cambrex) containing ascorbic acid, hydrocortisone, transferrin, insulin, huEGF, recombinant human hepatocyte growth factor (40 ng/mL), huFGF-basic (20 ng/mL), recombinant human fibroblast growth factor-4 (20 ng/mL), and stem cell factor (40 ng/mL). Cells were cultured for 29 or more days to induce differentiation to precursor cells of both hepatocytes and pancreatic cells lineage. MLPC changed from a fibroblast morphology to a hepatocyte morphology, expressed cell surface receptors for Hepatocyte Growth Factor, and produced both human serum albumin, a cellular product of hepatocytes, and insulin, a cellular product of pancreatic islet cells, both confirmed by intracellular antibody staining on day 30.

Example 12

Differentiation of MLPC into Respiratory Epithelial Cells

MLPCs were isolated from 4 of 16 umbilical cord blood units (American Red Cross) and expanded as described in Example 2. In particular, following homo- and heterophilic aggregation of undesired cell populations and subsequent sedimentation by gravity, the supernatant containing stem cells was expressed. After overnight incubation (5% CO$_2$/37° C.) in a T-flask in MSCGM™, non-adherent cells were washed, leaving adherent cells to expand in culture. As MLPC colonies were observed, cells were further enriched by detachment (PBS/0.1% EGTA), generally at 60-70% confluence, and transfer to a new T-flask. Cloning was achieved by a standard limited-dilution technique as discussed in Example 5. Clonal cell lines UM081704-1 C3 and E8 were used.

For differentiation assays, cultures were grown to approximately 80% confluence in MSCGM™ before adding Small Airway Epithelial Growth Media (SAGM™; Cambrex, Inc. CC-3118), a maintenance media designed for cultivation of terminally differentiated airway epithelium. SAGM™ consists of basal medium plus the following factors: bovine pituitary extract, hydrocortisone, human epidermal growth factor, epinephrine, insulin, triiodothyronine, transferrin, gentamicin/amphotericin-B, retinoic acid and BSA-fatty acid free. SAGM™ was changed on days 3-4; cells were harvested (PBS/0.1% EGTA) on day 8, and analyzed by transmission electron microscopy (TEM) and reverse transcriptase (RT)-PCR. For immunofluorescence (IF) staining, MLPC were initially plated at $2\times10^4$/well in a non-coated four-well chamber slide (Lab-Tek II; Nalge Nunc International, Rochester, N.Y., USA) then cultured as described above. Clonal cell lines were differentiated as above; however, they were harvested on day 3 for analysis by TEM and RT-PCR.

Cells were visualized by light microscopy (Eclipse TS100; Nikon Inc., Melville, N.Y., USA) throughout culture. Upon harvest, a cell pellet was made and prepared for analysis by TEM. Briefly, the pellet was rinsed in PBS and fixed in 2.5% glutaraldehyde in 0.1 m PBS buffer for 30 min. The sample was then post-fixed in 1% osmium tetroxide in 0.1 m PBS (30 min) and rinsed in PBS (three washes, 10 min each). The cells were enrobed and pelleted in 2% molten agarose, chilled at 4° C. for 30 min, diced into 1-mm cubes for dehydration through graded ethanol, and embedded in EMbed812 epoxy resin (EMS, Hatfield, Pa., USA). Ultra-thin sections of silver-gold interference color were stained in 3% aqueous uranyl acetate (20 min) then in Sato triple lead stain (3 min) prior to examination using an FEI CM12 Electron Microscope (FEI Co., Hillsboro, Oreg., USA).

Total RNA was isolated from MLPC in culture by employing the method of Chomezynski (*BioTechniques* 15:532-7 (1993)). Briefly, TRI Reagent (Molecular Research Center, Cincinnati, Ohio, USA) was added directly to the cells in culture flasks, causing simultaneous cell lysis and RNA solubilization. Reverse transcription was accomplished in a reaction containing 2.5 µg RNA, 1.0 µL random hexamers (5 µm final), 1 µL reverse transcriptase (Superscript™ Life Technologies, Rockville, Md.), 8 µL dNTP (2.5 mm each), 4 µL MgCl$_2$ (1.5 mm) and 2 µL 10x/buffer in a final volume of 20 µL, with incubation at 42° C. for 45 min followed by 15 min at 70° C.

A two-step nested RT-PCR strategy was used to amplify the surfactant protein C cDNA. Table 5 contains the primer sequences and expected RT-PCR product sizes for surfactant protein C (SPC). One microliter from the cDNA pool was used in the first PCR amplification with the following conditions: 5 min hot start at 95° C., 30 cycles of 95° C. for 30 s, 57° C. for 30 s, 72° C. for 30 s and a final extension for 5 min at 72° C. Two microliters of each primer diluted to 20 pmol/mL were used in each reaction. One microliter of the product from the first reaction was used as a template for the nested reaction, with the same cycling conditions and primer concentrations outlined above. RT-PCR amplification of beta-globin, a housekeeping gene, was used to monitor the quality of the mRNA and control for the efficiency of the RT step. PCR products were electrophoresed on 2% agarose gels and visualized by ethidium bromide staining. Product sizes were compared to a 100-bp ladder (Invitrogen, Carlsbad, Calif., USA).

TABLE 5

|     |                 | Primer Sequence                                                                                                            | Product Size (bp) |
| --- | --------------- | -------------------------------------------------------------------------------------------------------------------------- | ----------------- |
| SPC | First primer    | 5'AAAGAGGTCCTGATGGAGAGC3' (forward; SEQ ID NO:1) 5'TAGATGTAGTAGAGCGGCACCT3' (reverse (SEQ ID NO:2)                          | 456               |
|     | Nested          | 5'AACGCCTTCTTATCGTGGTG3' (forward; SEQ ID NO:3) 5'GTGAGAGCCTCAAGACTGG3' (reverse (SEQ ID NO:4)                              | 313               |

Differentiated cells also were stained for proSPC using an immunostaining procedure similar to Ali et al. (Tissue Eng. 2002; 8:541-50) with minor modifications. Cells were washed with HBSS+1% BSA twice, treated with 4% paraformaldehyde and incubated at room temperature for 20 min. The cells then were washed twice with HBSS+1% BSA. The primary pro-SPC Ab (Chemicon, AB3428, Temecula, Calif., USA) was added to the cells at a 1:125 dilution and incubated overnight at 4° C. After the primary Ab incubation, slides were washed twice with HBSS+1% BSA. The secondary Alexa Fluor 594 goat anti-rabbit Ab (Invitrogen, A11072) then was added at a 1:50 dilution and incubated with the cells for 20 min. Final HBSS+1% BSA washes were performed, and cover slips were placed onto the glass slides. Cells were viewed under a fluorescence microscope (Eclipse E200; Nikon Inc., Melville, N.Y., USA).

Figure 3:
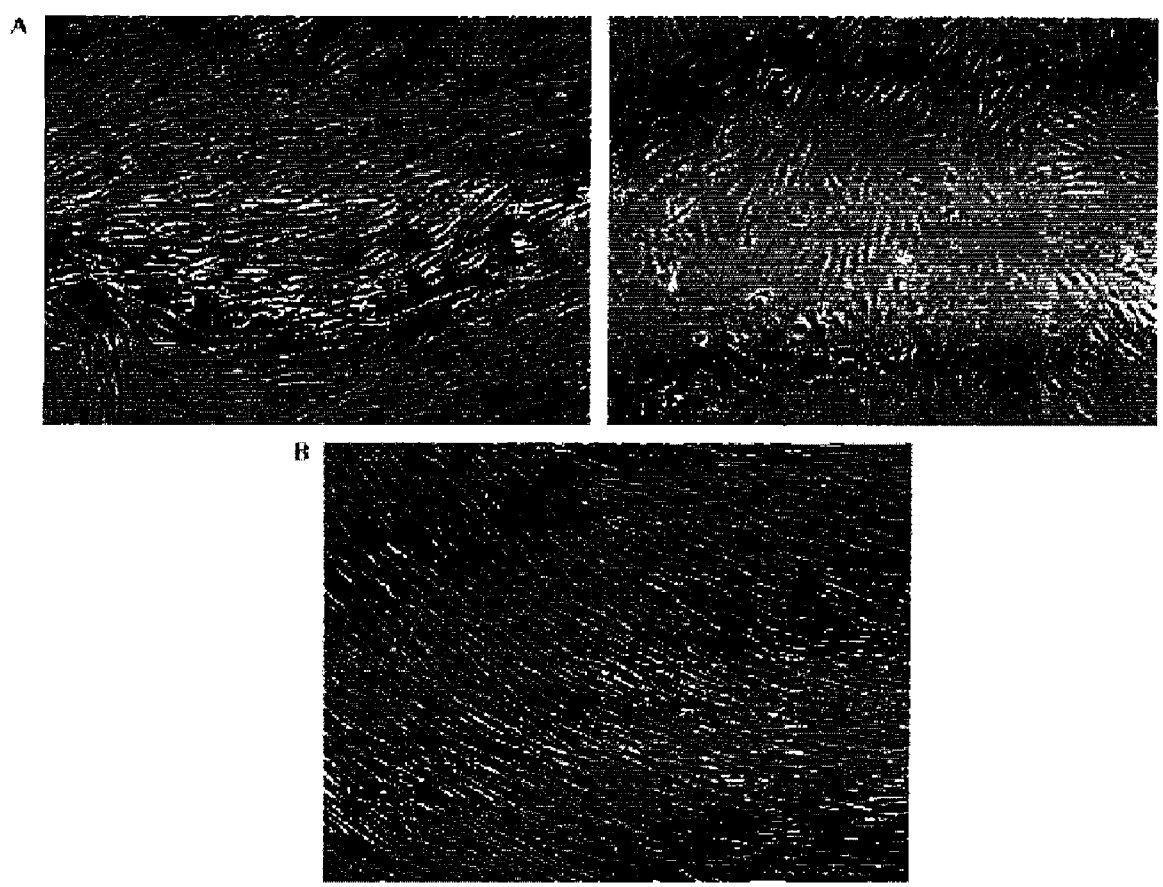
FIG. 3A-3B are light micrographs of MPLC induced in SAGM™ (3A) and control MLPC (i.e., cells held in MSCGM™).
Figure 4:
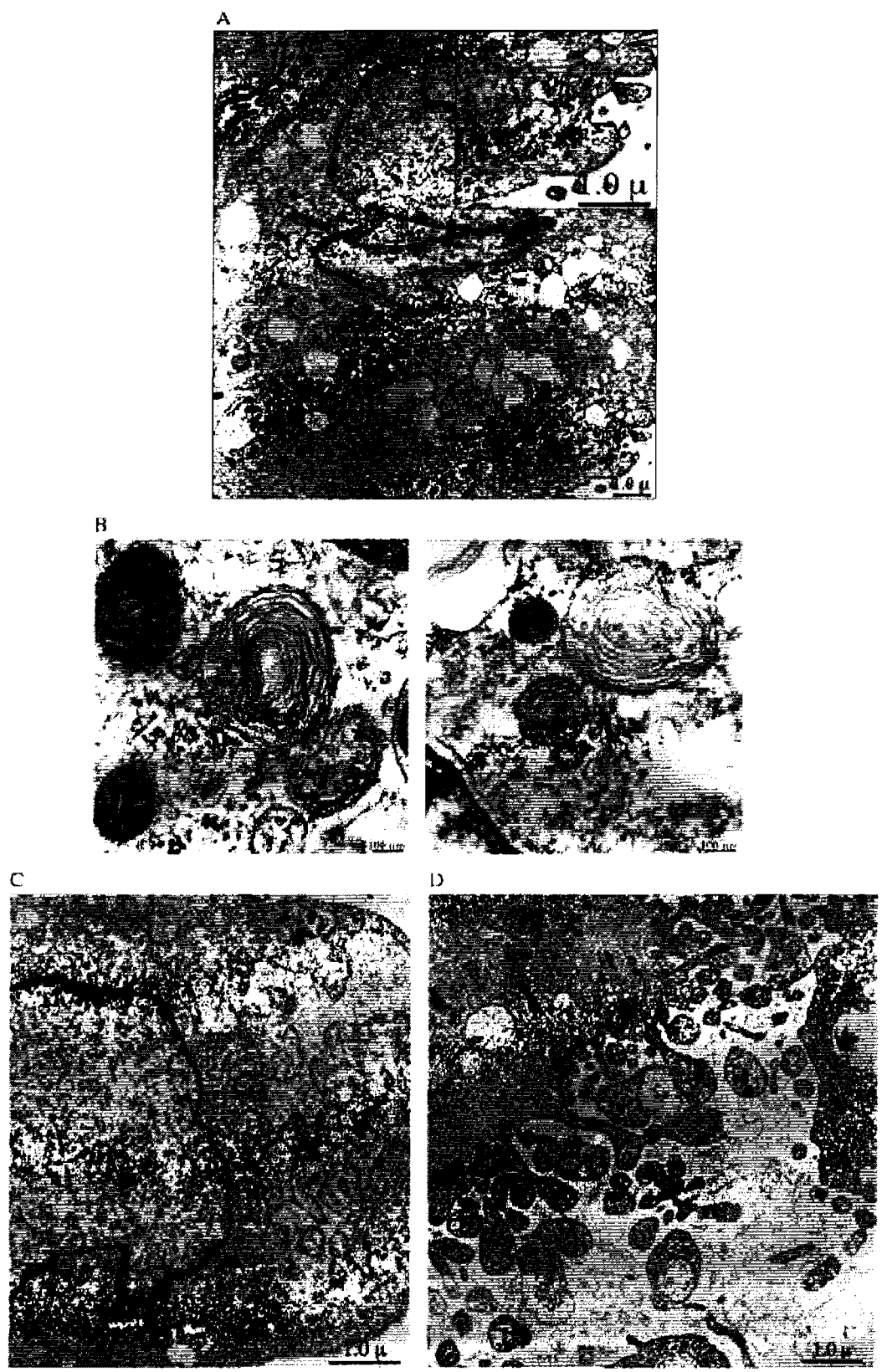
FIG. 4A-4D are transmission electron micrographs depicting the morphology of MLPC differentiated to type II alveolar cells. (A) Low power (6300×) micrograph of a differentiated cell. Three lamellar bodies (indicated by asterisks), numerous vacuoles, some multivesicular bodies, endocytic-type vesicles (enlarged inset) and abundant RER and mitochondria are noted. (B) Lamellar bodies (75 000×), one with multi-vesicular body fusing (indicated by asterisk). (C) Distended RER (10 000×). (D) Microvilli-like structures (10 000×).

By day 8 of culture (day 3 for clonal line UM081704-1 C3 and E8), cells in SAGM™ possessed a more epithelioid morphology; controls held in MSCGM™ maintained a fibroblast-like morphology (compare FIG. 3A and FIG. 3B). Ultrastructure consistent with type II alveolar cells was confirmed with a moderate number of cells from all mixed stem cell lines (n=2) and all clonal stem cell lines (n=2) tested by TEM. Differentiated cells showed lamellar bodies, multivesicular bodies and apparent lipid-laden vacuoles. Lamellar bodies are the organelles responsible for secretion of surfactant, with surfactant protein C (proSPC) being most specific for type II cells. Cells appeared metabolically active, with abundant mitochondria and distended rough endoplasmic reticulum (RER). Multiple small vesicles near the cell surface (appearing as endocytic vesicles originating from what resembled clathrin-coated pits) and throughout the cytoplasm were observed, suggestive of cellular product transport/trafficking (FIG. 4A-FIG. 4D). The ultrastructural findings of the control cells were substantially different from that of the test cells. RER was present, although not nearly as distended, and endocytic-type vesicles as well as multivesicular bodies were much less common. Rare organelles consistent with lamellar bodies were noted, however.

SPC mRNA was evident in RNA samples from mixed (n=4) and clonal (n=2) MLPC differentiated in SAGM™. However, SPC mRNA was not identified in RNA samples from MLPC controls. The presence of pro-SPC protein was confirmed by IF staining of both mixed (n=3) and clonal (n=2) stem cell lines. Essentially all the MLPC of each culture induced in SAGM™ were successfully differentiated. MLPC controls (maintained in MSCGM™) were negative. Table 6 summarizes all the results.

TABLE 6

| Cell ID | LM | TEM | IF | RT-PCR |
|---|---|---|---|---|
| MC1 | + | NA | + | + |
| Ctl MC1 | − | NA | − | − |
| MC2 | + | + | + | + |
| Ctl MC2 | − | * | − | − |
| MC3 | − | NA | § | + |
| Ctl MC3 | + | NA | − | − |
| MC4 | + | + | + | + |
| Ctl MC4 | − | NA | − | − |
| CC1 | + | + | + | + |
| Ctl CC1 | − | NA | − | − |
| CC2 | + | + | + | + |
| Ctl CC2 | − | NA | − | − |

MC, mixed stem cell line;
CC, clonal stem cell line;
Ctl, control;
LM, light microscopy changes;
TEM, transmission electron microscopy findings;
IF, IF (pro-SPC+);
RT-PCR, reverse transcriptase-polymerase chain reaction (SPC mRNA+);
NA, not applicable (i.e. not performed);
* rare lamellar-like bodies present;
§ in conclusive Example 13

Differential Gene Expression in Respiratory Epithelial Cells

Total RNA was isolated from cultured MLPC (3 control lines maintained in MSCGM™ and 3 induced/differentiated cell lines maintained in SAGM™ for either 3 days for clonal cell lines or 8 days for mixed cell lines). The TRI REAGENT (Molecular Research Center, Inc.) protocol was used to isolate the total RNA, which then was cleaned using the RNeasy mini kit protocol (Qiagen Inc.). Total RNA was used to synthesize double stranded cDNA according to the manufacturer's instructions (Affymetrix, Inc.). The first strand synthesis reaction was performed using 1 µg RNA, SuperScript II Reverse Transcriptase (Invitrogen), and T7-(dT)24 primer (Genset Corp.). Second strand synthesis reaction followed using E. coli DNA ligase, E. coli DNA polymerase I, and E. coli RNase H (Invitrogen). The double stranded cDNA was column-purified using the Affymetrix supplied module (Affymetrix, Inc.) and used as template in an in vitro T7 transcription reaction using the MEGAscript T7 high yield transcription kit (Ambion) and biotinylated nucleotides Biotin-11-CTP, Biotin-16-UTP (NEN, Perkin-Elmer, Boston, Mass.). A 20 µg cRNA aliquot was fragmented in 1× fragmentation buffer (40 mM Tris-acetate pH 8.1, 100 mM KOAc, 30 mM MgOAc) at 94° C. for 35 min. Assessment of fragmented, labeled cRNA was performed via use of an Agilent chip (Agilent Technologies, Inc). Fifteen µg of the fragmented cRNA was hybridized to a human GeneChip probe array (Affymetrix, U133 plus 2.0) for 16 hours at 45° C. The probe arrays were washed, stained, and scanned in an Affymetrix fluidics station and scanner following the manufacturer's protocols. CEL files were incorporated in Expressionist software Refiner (Genedata AG) and condensed using the Mas5 algorithm.

Over 23,000 data points were generated for each of the 6 samples (3 distinct biological replicates of control and induced samples). The data were grouped into control (maintained in MSCGM™) and induced (differentiated with SAGM™) for comparison of differential gene expression. Comparison of the two mixed MLPC (each with 1 control and 1 induced sample) was performed using Expressionist (Genedata AG) software and the Student's T-test. With a P value of 0.01 and an inter-group gap of 2.0, 373 genes were found to be differentially expressed between the control and induced groups. See Table 7. Two hundred and fifteen (215) genes were up-regulated in the induced MLPC relative to the control MLPC while 158 genes were down-regulated in the induced MLPC relative to the control MLPC. Functional categories of genes included those for: cell cycle control (P21, cyclin L1, cyclin M2 and cyclin M3); signaling (N-Myc and STAT interactor); protein protection (gp96-expressed in non-small cell lung cancers); and lamellar body formation and maintenance (V-ATPases). Additional genes that were noted to be differentially regulated, but were not included in the above list due to increased standard deviations, include: α-1 antitrypsin, a serine (or cysteine) protease inhibitor (expressed in lung epithelium) and LAMP-1 (required for the functioning of lysosomes and lamellar bodies).

Comparison of the two mixed MLPC lines and one clonal line (C3) (each with 1 control and 1 induced sample) also was performed using Expressionist (Genedata AG) software and the Student's T-test. With a P value of 0.01 and an inter-group gap of 1.0, 611 genes were found to be differentially expressed between the control and induced groups. See FIG. 5. As indicated in FIG. 5, the clonal and mixed lines produced similar results.

| Name | Description | UM102605 (Induced 1) | UM040505 (Induced 5) | UM102605 (Control 2)) | UM040505 (Control 6) |
|---|---|---|---|---|---|
| 218388_at | 6-phosphogluconolactonase | 232.9325485 | 192.0158453 | 995.7495684 | 1117.939752 |
| 218387_s_at | 6-phosphogluconolactonase | 257.3845942 | 244.8762365 | 841.478405 | 996.5209591 |
| 218795_at | acid phosphatase 6, lysophosphatidic | 431.7710248 | 360.5289608 | 115.7691221 | 130.837327 |
| 211160_x_at | actinin, alpha 1 | 787.1331545 | 853.4395645 | 2602.499925 | 2392.014111 |
| 206833_s_at | acylphosphatase 2, muscle type | 764.2784821 | 681.6869024 | 258.8335641 | 254.4796342 |
| 225711_at | ADP-ribosylation-like factor 6 interacting protein 6 | 48.07697872 | 42.9865854 | 160.3272601 | 164.5098752 |
| 217939_s_at | Aftiphilin protein | 1065.95031 | 1005.347289 | 409.0402229 | 426.3652704 |
| 205623_at | aldehyde dehydrogenase 3 family, memberA1 | 953.393562 | 690.0954687 | 54.16935048 | 69.89549312 |
| 205621_at | alkB, alkylation repair homolog (E. coli) | 1288.783721 | 1273.019042 | 294.9263359 | 322.679012 |
| 211071_s_at | ALL1-fused gene from chromosome 1q | 899.2506743 | 823.7948636 | 3548.384618 | 4720.905472 |
| 202631_s_at | amyloid beta precursor protein (cytoplasmic tail) binding protein 2 | 855.464105 | 729.5811818 | 314.3217782 | 317.2561076 |
| 214783_s_at | annexin A11 | 95.90794493 | 82.40065923 | 325.9812818 | 349.534973 |
| 223677_at | APG10 autophagy 10-like (S. cerevisiae) | 36.33807837 | 35.50750598 | 110.9272106 | 103.4972419 |
| 206632_s_at | apolipoprotein B mRNA editing enzyme, | 9.664322016 | 10.89275362 | 35.29102469 | 37.38934657 |

-continued

| Name | Description | UM102605 (Induced 1) | UM040505 (Induced 5) | UM102605 (Control 2)) | UM040505 (Control 6) |
|---|---|---|---|---|---|
| | catalytic polypeptide-like 3B | | | | |
| 224461_s_at | apoptosis-inducing factor (AIF)-like mitochondrion-associated inducer of death | 513.3964409 | 495.5737257 | 192.25735 | 194.1406353 |
| 208270_s_at | arginyl aminopeptidase (aminopeptidase B) | 1696.223538 | 1669.589236 | 796.9723521 | 786.2606108 |
| 201881_s_at | ariadne homolog, ubiquitin-conjugating enzyme E2 binding protein, 1 (*Drosophila*) | 922.406774 | 858.5993761 | 407.1602212 | 411.2896043 |
| 229906_at | armadillo repeat containing 7 | 125.3020944 | 131.2541807 | 35.86337013 | 40.87121772 |
| 234210_x_at | ARP2 actin-related protein 2 homolog (yeast) | 29.69008383 | 24.2813998 | 81.43013915 | 80.40166565 |
| 208832_at | ataxin 10 | 120.5425924 | 118.1035312 | 301.1527947 | 276.8752668 |
| 210337_s_at | ATP citrate lyase | 513.8681548 | 568.6822261 | 1253.264185 | 1199.518977 |
| 224729_s_at | ATP synthase mitochondrial F1 complex assembly factor 1 | 1255.707174 | 1240.473078 | 599.4950074 | 587.2925577 |
| 203926_x_at | ATP synthase, H+ transporting, mitochondrial F1 complex, delta subunit | 78.07592504 | 77.31024488 | 199.2234219 | 187.6067131 |
| 201089_at | ATPase, H+ transporting, lysosomal 56/58 kDa, V1 subunit B, isoform 2 | 2207.171658 | 2316.07487 | 880.2972277 | 952.8845308 |
| 210534_s_at | B9 protein | 129.8678693 | 132.8558971 | 296.9143684 | 314.578778 |
| 221534_at | Basophilic leukemia expressed protein BLES03 | 1544.741389 | 1484.274599 | 589.8298911 | 636.7915444 |
| 223566_s_at | BCL6 co-repressor | 358.8674739 | 336.1210975 | 112.7859217 | 120.0217524 |
| 219433_at | BCL6 co-repressor | 332.9484556 | 343.0678686 | 105.9881922 | 122.529171 |
| 213882_at | Beta-amyloid binding protein precursor | 335.9797646 | 334.3786318 | 97.2146078 | 119.0608225 |
| 201261_x_at | biglycan | 534.2168128 | 580.2160065 | 1367.653014 | 1415.496557 |
| 213905_x_at | biglycan | 689.682618 | 751.0970149 | 2319.290878 | 2536.17854 |
| 213015_at | bobby sox homolog (*Drosophila*) | 877.049267 | 879.6170622 | 400.7927428 | 395.8863844 |
| 203053_at | breast carcinoma amplified sequence 2 | 3480.894415 | 3018.17979 | 1304.405754 | 1413.751508 |
| 227775_at | bruno-like 6, RNA binding protein (*Drosophila*) | 48.4647729 | 47.85327245 | 15.85528425 | 16.07209581 |
| 207173_x_at | cadherin 11, type 2, OB-cadherin (osteoblast) | 2631.415103 | 3003.810787 | 7761.131625 | 8443.450055 |
| 244091_at | cadherin 13, H-cadherin (heart) | 33.96901546 | 36.92906882 | 128.3478857 | 105.1511507 |
| 231881_at | caldesmon 1 | 46.52898691 | 42.80777854 | 127.7260034 | 145.2901914 |
| 237289_at | cAMP responsive element binding protein 1 | 180.7212305 | 172.56377 | 423.9871386 | 441.7969349 |
| 212784_at | capicua homolog (*Drosophila*) | 406.4304869 | 352.0910103 | 124.5454008 | 116.5472173 |
| 209667_at | carboxylesterase 2 (intestine, liver) | 112.7791456 | 103.5310531 | 323.9581614 | 348.9358039 |
| 209668_x_at | carboxylesterase 2 (intestine, liver) | 119.6500997 | 108.7382766 | 249.4746245 | 274.2924492 |
| 212063_at | CD44 antigen (homing function and Indian blood group system) | 2634.037595 | 2719.95597 | 5610.952964 | 5913.712169 |
| 221973_at | CDNA clone IMAGE: 5217021, with apparent retained intron | 31.20045096 | 38.62239143 | 144.4386848 | 122.9141623 |
| 202254_at | CDNA clone IMAGE: 5286091, partial cds | 114.120576 | 115.9449115 | 332.7786234 | 288.1626577 |
| 238164_at | CDNA FLJ34168 fis, clone FCBBF3015131 | 40.0253295 | 39.56426461 | 99.6804649 | 104.2299267 |
| 235761_at | CDNA FLJ36553 fis, clone TRACH2008478 | 33.45491104 | 37.65451163 | 89.7167398 | 106.3847038 |
| 239218_at | CDNA FLJ43039 fis, clone BRTHA3003023 | 50.96439796 | 59.22154886 | 1234.031822 | 1299.337173 |
| 207428_x_at | Cell division cycle 2-like 1 (PITSLRE proteins) | 334.1540505 | 301.2454315 | 122.6580106 | 140.7735561 |
| 219345_at | CGI-143 protein | 217.2535038 | 231.9858212 | 94.29275541 | 106.493216 |
| 204233_s_at | choline kinase alpha | 151.9315166 | 152.2219424 | 40.16181352 | 49.92736209 |
| 1554015_a_at | Chromodomain helicase DNA binding protein 2 | 459.3545051 | 428.4685675 | 88.99415471 | 100.2801585 |
| 230129_at | chromosome 10 open reading frame 89 | 213.8602127 | 192.3380413 | 75.54370197 | 82.55289784 |
| 227575_s_at | chromosome 14 open reading frame 102 | 223.4110328 | 212.1355417 | 69.82154241 | 84.75695982 |
| 218363_at | chromosome 14 open reading frame 114 | 632.0921356 | 605.5669478 | 210.2187852 | 241.8470662 |
| 226510_at | chromosome 14 open reading frame 125 | 425.6674831 | 398.5952577 | 1035.589034 | 1180.384514 |
| 1553801_a_at | chromosome 14 open reading frame 126 | 88.36359773 | 90.74127223 | 272.9616014 | 238.0933743 |
| 220173_at | chromosome 14 open reading frame 45 | 54.96757309 | 69.32339267 | 335.5998069 | 324.6184429 |
| 214720_x_at | chromosome 2 open reading frame 26 | 269.4788494 | 231.7053493 | 876.1789865 | 896.5669926 |
| 225252_at | chromosome 20 open reading frame 139 [BLAST] | 2841.367338 | 2565.302235 | 907.9542057 | 938.6734357 |
| 212176_at | chromosome 6 open reading frame 111 | 1193.577193 | 917.3843541 | 244.8098056 | 250.9880697 |
| 219006_at | chromosome 6 open reading frame 66 | 2546.841914 | 2344.830228 | 1043.234093 | 1097.034308 |
| 223811_s_at | chromosome 7 open reading frame 20 | 208.0501268 | 224.4300787 | 88.77236542 | 98.68404055 |
| 222195_s_at | chromosome 9 open reading frame 156 | 372.1044786 | 442.4625058 | 105.1506995 | 114.4704679 |
| 218929_at | Collaborates/cooperates with ARF (alternate reading frame) protein | 767.9941676 | 703.3296567 | 217.0714609 | 234.9532008 |
| 225681_at | collagen triple helix repeat containing 1 | 112.9498023 | 91.85363974 | 4374.939275 | 3302.273493 |
| 211980_at | collagen, type IV, alpha 1 | 1024.639379 | 847.9758961 | 6648.737045 | 9046.585818 |
| 213454_at | cortistatin | 105.2292476 | 99.66126408 | 278.347012 | 334.6416587 |
| 205035_at | CTD (carboxy-terminal domain, RNA polymerase II, polypeptide A) phosphatase, subunit 1 | 140.6641832 | 130.6291789 | 41.37869608 | 37.31935456 |
| 1555411_a_at | cyclin L1 | 1169.349377 | 1185.584861 | 497.0597269 | 568.6358581 |
| 206818_s_at | cyclin M2 | 187.2519907 | 171.6483197 | 45.83260586 | 55.74967826 |
| 220739_s_at | cyclin M3 | 367.1340021 | 345.5729888 | 79.69282448 | 68.71058212 |
| 226402_at | cytochrome P450, family 2, subfamily U, polypeptide 1 | 1086.570608 | 921.9516542 | 433.1664952 | 435.3351025 |
| 228391_at | cytochrome P450, family 4, subfamily V, polypeptide 2 | 28.89487919 | 23.99399322 | 172.8163222 | 216.7516508 |

-continued

| Name | Description | UM102605 (Induced 1) | UM040505 (Induced 5) | UM102605 (Control 2)) | UM040505 (Control 6) |
|---|---|---|---|---|---|
| 226745_at | cytochrome P450, family 4, subfamily V, polypeptide 2 | 23.80146454 | 32.13094376 | 155.4500181 | 184.8334672 |
| 229069_at | Cytokine induced protein 29 kDa | 639.310702 | 603.7594342 | 157.3633575 | 148.2637704 |
| 215785_s_at | cytoplasmic FMR1 interacting protein 2 | 460.7090536 | 621.3575618 | 105.3024817 | 112.5414319 |
| 203409_at | Damage-specific DNA binding protein 2, 48 kDa | 1016.382983 | 1225.571644 | 313.0805287 | 273.942932 |
| 204556_s_at | DAZ interacting protein 1 | 84.882016 | 68.52169704 | 375.9731555 | 478.1446453 |
| 204017_at | DEAD (Asp-Glu-Ala-Asp) box polypeptide 17 | 1181.386815 | 1222.445602 | 5416.288392 | 4458.845304 |
| 224315_at | DEAD (Asp-Glu-Ala-Asp) box polypeptide 20 | 453.6237389 | 423.0020856 | 153.7217042 | 146.5277112 |
| 200694_s_at | DEAD (Asp-Glu-Ala-Asp) box polypeptide 24 | 3804.385791 | 3473.91027 | 1544.590396 | 1343.19512 |
| 223140_s_at | DEAH (Asp-Glu-Ala-His) box polypeptide 36 | 949.5964833 | 1026.46098 | 417.0638654 | 395.2788122 |
| 203891_s_at | death-associated protein kinase 3 | 61.64603663 | 66.70498666 | 160.3407923 | 151.6627604 |
| 201894_s_at | decorin | 924.4626646 | 964.0184557 | 2234.979859 | 2395.391532 |
| 219279_at | dedicator of cytokinesis 10 | 63.65659551 | 53.3733274 | 479.5280774 | 440.100973 |
| 230207_s_at | dedicator of cytokinesis 5 | 586.2539578 | 609.4120619 | 1312.2058 | 1346.233812 |
| 217989_at | dehydrogenase/reductase (SDR family) member 8 | 709.107603 | 779.6286902 | 214.4803112 | 203.4864548 |
| 237702_at | Developmentally regulated RNA-binding protein 1 | 125.9850242 | 164.1484088 | 31.82422295 | 30.50942785 |
| 229456_s_at | dimethylarginine dimethylaminohydrolase 1 | 263.4144274 | 276.16075 | 597.1113859 | 575.7482229 |
| 204676_at | DKFZP564K2062 protein | 531.916687 | 494.1461227 | 233.7018714 | 211.7278782 |
| 212019_at | DKFZP564M182 protein | 236.6069076 | 206.8752857 | 58.900413 | 56.7781286 |
| 222447_at | DORA reverse strand protein 1 | 171.796611 | 167.4894992 | 360.5746927 | 407.9805499 |
| 205399_at | doublecortin and CaM kinase-like 1 | 63.25160329 | 78.28379297 | 559.623007 | 474.6198699 |
| 203635_at | Down syndrome critical region gene 3 | 919.1761181 | 982.7995454 | 383.3816147 | 398.2462611 |
| 1554966_a_at | Downregulated in ovarian cancer 1 | 113.9272876 | 126.6199223 | 564.6160134 | 580.0677312 |
| 230740_at | EH-domain containing 3 | 126.9304595 | 113.4219961 | 260.4789195 | 264.0590701 |
| 222779_s_at | ELG protein | 392.5861129 | 398.1733467 | 163.192371 | 168.9795043 |
| 219432_at | Ellis van Creveld syndrome | 146.6229048 | 145.8486175 | 508.83624 | 502.194006 |
| 204400_at | embryonal Fyn-associated substrate | 121.6952961 | 146.777429 | 444.5472679 | 498.8250724 |
| 217820_s_at | enabled homolog (Drosophila) | 1471.607027 | 1274.451207 | 3221.804226 | 3212.759064 |
| 238633_at | enhancer of polycomb homolog 1 (Drosophila) | 135.7250543 | 142.727268 | 34.92156823 | 28.11186959 |
| 220161_s_at | erythrocyte membrane protein band 4, 1 like 4B | 121.0546093 | 130.4043852 | 358.4453949 | 348.6003656 |
| 202461_at | eukaryotic translation initiation factor 2B, subunit 2 beta, 39 kDa | 2843.407148 | 3556.705471 | 867.3005985 | 947.455723 |
| 208773_s_at | Eukaryotic translation initiation factor 4E binding protein 3 | 1098.837892 | 1021.596594 | 462.4052669 | 465.2668104 |
| 213648_at | exosome component 7 | 423.8884897 | 464.2974213 | 168.6006598 | 166.6020801 |
| 212231_at | F-box protein 21 | 930.1977924 | 1053.814481 | 420.1642051 | 455.5694504 |
| 225736_at | F-box protein 22 | 1268.242864 | 1121.378568 | 413.9025146 | 367.7677518 |
| 1555971_s_at | F-box protein 28 | 1879.177533 | 1568.841589 | 614.0488363 | 598.6611581 |
| 201863_at | family with sequence similarity 32, member A | 2452.190758 | 2555.084192 | 1194.023483 | 1110.886589 |
| 210933_s_at | fascin homolog 1, actin-bundling protein (Strongylocentrotus purpuratus) | 262.6023841 | 264.0720395 | 1371.854722 | 1553.005862 |
| 201798_s_at | fer-1-like 3, myoferlin (C. elegans) | 2200.569988 | 2396.095237 | 5661.197948 | 5925.273675 |
| 211864_s_at | fer-1-like 3, myoferlin (C. elegans) | 1027.84168 | 1181.135033 | 3563.257941 | 3862.424481 |
| 207813_s_at | ferredoxin reductase | 609.7294692 | 540.4387375 | 69.36303811 | 48.44418644 |
| 214752_x_at | filamin A, alpha (actin binding protein 280) | 546.8089976 | 537.6193919 | 1705.274056 | 1847.034309 |
| 1554424_at | FIP1 like 1 (S. cerevisiae) | 258.1721311 | 307.9459258 | 107.0021258 | 107.4949107 |
| 219390_at | FK506 binding protein 14, 22 kDa | 685.5104649 | 742.9630019 | 1826.742617 | 2206.550793 |
| 212472_at | Flavoprotein oxidoreductase MICAL2 [BLAST] | 617.6582237 | 600.6653218 | 2480.10282 | 1940.674297 |
| 1568868_at | FLJ16008 protein | 23.19738119 | 27.68243012 | 181.9925339 | 239.6403668 |
| 223492_s_at | FLJ40411 protein | 139.8293199 | 159.3622427 | 1082.157464 | 954.1421495 |
| 211799_x_at | FLJ45422 protein | 1120.050588 | 1272.015422 | 522.144114 | 550.9200605 |
| 214505_s_at | four and a half LIM domains 1 | 1506.520986 | 1663.963782 | 5704.984442 | 5317.107901 |
| 210299_s_at | four and a half LIM domains 1 | 2029.065652 | 2182.920341 | 6051.129229 | 5774.05538 |
| 229519_at | fragile X mental retardation, autosomal homolog 1 | 1594.089884 | 1510.538402 | 480.5925112 | 547.9676432 |
| 213750_at | Full length insert cDNA YH77E09 | 1497.598835 | 1221.946152 | 336.8906561 | 325.3936272 |
| 229201_at | Full-length cDNA clone CS0DF014YC15 of Fetal brain of Homo sapiens (human) | 17.4170403 | 20.88694349 | 51.05304258 | 49.59301904 |
| 225348_at | FUS interacting protein (serine-arginine rich) 1 | 63.4827541 | 62.86959978 | 316.7714761 | 363.2835153 |
| 218895_at | G patch domain containing 3 | 169.8660597 | 177.4372456 | 66.08317356 | 72.44871091 |
| 200070_at | gb: BC001393.1/DB_XREF = gi: 12655084 /FEA = FLmRNA /CNT = 168 /TID = Hs.4973.1 /TIER = FL + Stack /STK = 71 /UG = Hs.4973 /LL = 27013 /UG_GENE = CGI-57 /DEF = Homo sapiens, hypothetical protein, clone MGC: 782, mRNA, co . . . | 574.7009898 | 499.9657159 | 199.8425282 | 209.0745621 |
| 218343_s_at | general transcription factor IIIC, polypeptide 3, 102 kDa | 905.5873479 | 807.3736894 | 329.5070946 | 344.6690254 |
| 204222_s_at | GLI pathogenesis-related 1 (glioma) | 683.6501225 | 607.4519926 | 3942.820629 | 4778.504069 |
| 227027_at | glutamine-fructose-6-phosphate | 601.4262472 | 598.3486568 | 1616.426022 | 1683.911252 |

-continued

| Name | Description | UM102605 (Induced 1) | UM040505 (Induced 5) | UM102605 (Control 2)) | UM040505 (Control 6) |
|---|---|---|---|---|---|
| | transaminase 1 | | | | |
| 209304_x_at | growth arrest and DNA-damage-inducible, beta | 2131.389351 | 3091.949872 | 354.5130586 | 332.2549118 |
| 206204_at | growth factor receptor-bound protein 14 | 47.52412733 | 49.1079314 | 827.4881247 | 1478.220085 |
| 236648_at | guanine monphosphate synthetase | 32.00847005 | 36.68899459 | 105.8417301 | 120.4477891 |
| 221737_at | guanine nucleotide binding protein (G protein) alpha 12 | 202.252498 | 196.3873337 | 418.8188103 | 443.4772278 |
| 202270_at | guanylate binding protein 1, interferon-inducible, 67 kDa | 358.5799342 | 404.7218553 | 1246.949738 | 1298.832939 |
| 208886_at | H1 histone family, member 0 | 1919.741045 | 1754.027443 | 271.3209612 | 361.3833507 |
| 225245_x_at | H2A histone family, member J | 2866.421656 | 3544.725015 | 652.4676295 | 788.3490499 |
| 224301_x_at | H2A histone family, member J | 2671.557992 | 2713.411533 | 794.4533486 | 947.1070721 |
| 202978_s_at | HCF-binding transcription factor Zhangfei | 434.8666302 | 363.2985863 | 140.7970522 | 136.4619939 |
| 202344_at | heat shock transcription factor 1 | 361.0767494 | 370.9915107 | 114.3389966 | 92.26486871 |
| 201655_s_at | heparan sulfate proteoglycan 2 (perlecan) | 286.4818738 | 293.6191154 | 1221.278595 | 1280.48599 |
| 238565_at | HepG2 partial cDNA, clone hmd2d12m5. | 55.45350331 | 50.40969008 | 153.9060915 | 139.3545956 |
| 220387_s_at | HERV-H LTR-associating 3 | 428.438535 | 423.5080577 | 177.4273467 | 164.1397208 |
| 206809_s_at | heterogeneous nuclear ribonucleoprotein A3 | 238.8903358 | 278.0000167 | 694.2322963 | 738.2576401 |
| 204112_s_at | histamine N-methyltransferase | 181.9448108 | 140.2143685 | 634.6595798 | 607.7014374 |
| 203203_s_at | HIV-1 rev binding protein 2 | 1065.494476 | 1055.187697 | 428.0874951 | 504.9534889 |
| 226142_at | HIV-1 rev binding protein 2 | 467.7618189 | 448.1080343 | 3318.883559 | 4086.74494 |
| 214085_x_at | HIV-1 rev binding protein 2 | 870.6025369 | 788.7848548 | 4327.851793 | 5617.924322 |
| 224756_s_at | HLA-B associated transcript 5 | 898.9951481 | 795.5451138 | 267.0453666 | 267.3126536 |
| 242366_at | *Homo sapiens*, clone IMAGE: 3858719, mRNA | 116.6125351 | 129.8554228 | 340.96049 | 403.1868648 |
| 225443_at | *Homo sapiens*, clone IMAGE: 4082361, mRNA | 743.3357899 | 809.7355602 | 318.8643379 | 364.1199509 |
| 227765_at | *Homo sapiens*, Similar to L1 repeat, Tf subfamily, member 14, clone IMAGE: 4820809, mRNA | 860.8442463 | 750.6183197 | 318.2107532 | 305.1448468 |
| 203644_s_at | HSV-1 stimulation-related gene 1 | 182.5921335 | 178.3779561 | 77.50236238 | 65.85501967 |
| 237465_at | Hypothetical gene supported by BC062741 | 83.60657694 | 94.45147083 | 315.4433804 | 281.2775294 |
| 225967_s_at | Hypothetical LOC284184 | 3002.85128 | 3464.980038 | 1478.752358 | 1395.151014 |
| 239466_at | Hypothetical LOC344595 | 54.40231965 | 46.40735201 | 129.4094384 | 130.6230747 |
| 227158_at | Hypothetical LOC400201 | 179.3207466 | 210.1126577 | 580.8349673 | 617.4291278 |
| 227285_at | Hypothetical protein BC017397 | 316.1390643 | 288.7267138 | 34.16313851 | 49.2399316 |
| 226278_at | Hypothetical protein DKFZp313A2432 | 1201.102105 | 1022.709817 | 363.5292343 | 405.9243998 |
| 236079_at | Hypothetical protein DKFZp667E0512 | 35.60525769 | 46.10708893 | 221.9536733 | 234.0072988 |
| 238609_at | hypothetical protein DKFZp727G131 | 320.929859 | 299.9296522 | 133.2357828 | 133.7000541 |
| 213079_at | Hypothetical protein DT1P1A0 | 626.0819408 | 554.0397436 | 243.5008724 | 267.7477891 |
| 219060_at | Hypothetical protein FLJ10204 | 223.259704 | 225.2168494 | 468.8933605 | 456.1961622 |
| 218894_s_at | Hypothetical protein FLJ10292 | 120.2605851 | 130.9559181 | 288.628843 | 313.6712224 |
| 220260_at | Hypothetical protein FLJ11082 | 164.0922191 | 157.4574817 | 460.8936245 | 473.1294321 |
| 218051_s_at | Hypothetical protein FLJ12442 | 207.5134212 | 195.0353768 | 929.6129301 | 960.0357651 |
| 236816_at | Hypothetical protein FLJ13089 | 111.5665269 | 99.65708222 | 32.63337666 | 29.60886124 |
| 222893_s_at | Hypothetical protein FLJ13150 | 755.6658184 | 738.8746521 | 241.0757589 | 262.002522 |
| 204800_s_at | Hypothetical protein FLJ13639 | 23.64930327 | 25.26128738 | 54.84745038 | 55.78501896 |
| 225702_at | Hypothetical protein FLJ14825 | 943.9339273 | 867.6124797 | 397.2973307 | 377.4077788 |
| 225637_at | Hypothetical protein FLJ20186 | 838.1578242 | 887.0618887 | 303.8904198 | 286.3431165 |
| 227968_at | Hypothetical protein FLJ34283 | 590.6863646 | 493.0836452 | 167.5063516 | 192.098542 |
| 238025_at | Hypothetical protein FLJ34389 | 77.5609798 | 75.02282613 | 264.0321261 | 234.1085268 |
| 218403_at | Hypothetical protein HSPC132 | 5378.599257 | 5325.212121 | 877.5236451 | 1161.915907 |
| 231249_at | Hypothetical protein HT036 | 179.460348 | 154.7550299 | 72.01593521 | 70.49224479 |
| 222698_s_at | Hypothetical protein IMPACT | 99.46177574 | 81.06553891 | 496.8360336 | 485.1736622 |
| 231640_at | Hypothetical protein LOC144363 | 161.3333512 | 164.1840264 | 64.74530432 | 65.87964354 |
| 235779_at | Hypothetical protein LOC284408 | 167.9520772 | 207.6417002 | 54.52696629 | 59.44653194 |
| 225933_at | Hypothetical protein LOC339229 | 333.3443261 | 346.9720113 | 144.0290548 | 119.6137621 |
| 222585_x_at | Hypothetical protein LOC51315 | 240.4558065 | 2674416789 | 675.3973792 | 717.2539173 |
| 224661_at | Hypothetical protein MGC14156 | 1196.544397 | 993.3968179 | 430.4863676 | 434.6935186 |
| 226323_at | Hypothetical protein MGC20398 | 582.874222 | 629.8329324 | 207.1818078 | 242.4581192 |
| 1555916_at | Hypothetical protein MGC29784 | 680.9000769 | 647.1138589 | 190.2922228 | 188.9695199 |
| 244741_s_at | Hypothetical protein MGC9913 | 537.5014807 | 507.1007479 | 204.7145663 | 233.7830122 |
| 1554452_a_at | Hypoxia-inducible protein 2 | 76.72284176 | 82.12764231 | 233.6083939 | 234.5762836 |
| 218507_at | Hypoxia-inducible protein 2 | 86.18176123 | 83.24203535 | 192.6108083 | 214.1544131 |
| 210511_s_at | inhibin, beta A (activin A, activin AB alpha polypeptide) | 197.1064343 | 139.8710651 | 4065.966214 | 4835.730763 |
| 213076_at | inositol 1,4,5-trisphosphate 3-kinase C | 146.6815055 | 165.8709157 | 66.81869957 | 64.35682674 |
| 203607_at | inositol polyphosphate-5-phosphatase F | 410.4309161 | 475.3632218 | 1355.76675 | 1594.714066 |
| 227372_s_at | Insulin receptor tyrosine kinase substrate | 415.6679409 | 401.7983002 | 115.1475546 | 92.64846718 |
| 213416_at | integrin, alpha 4 (antigen CD49D, alpha 4 subunit of VLA-4 receptor) | 64.72295615 | 61.35108836 | 187.4672108 | 164.1458258 |
| 209297_at | intersectin 1 (SH3 domain protein) | 159.6205132 | 157.1039066 | 376.144405 | 376.5580562 |
| 201509_at | isocitrate dehydrogenase 3 (NAD4+) beta | 512.1809489 | 563.6750322 | 191.0198807 | 212.312534 |
| 225798_at | Juxtaposed with another zinc finger gene 1 | 244.7219204 | 241.4534481 | 627.6162191 | 544.0944267 |
| 214185_at | KH domain containing, RNA binding, signal transduction associated 1 | 87.29058171 | 93.22741298 | 42.94461657 | 40.37024233 |

| Name | Description | UM102605 (Induced 1) | UM040505 (Induced 5) | UM102605 (Control 2)) | UM040505 (Control 6) |
|---|---|---|---|---|---|
| 212264_s_at | KIAA0261 | 1368.232896 | 1643.267363 | 564.7646479 | 536.1892877 |
| 203049_s_at | KIAA0372 | 1227.261134 | 1170.619139 | 2564.156323 | 2568.04986 |
| 213300_at | KIAA0404 protein | 343.6133754 | 312.7463012 | 106.9855957 | 111.6077638 |
| 203958_s_at | KIAA0478 gene product | 239.8864009 | 234.6949914 | 62.80733518 | 69.8497477 |
| 229872_s_at | KIAA0493 protein | 330.3134831 | 385.1823101 | 132.1597933 | 120.1325452 |
| 212456_at | KIAA0664 protein | 371.6154393 | 369.6212837 | 176.8425149 | 155.3128745 |
| 212311_at | KIAA0746 protein | 57.02049577 | 54.29159935 | 182.7903177 | 201.0039781 |
| 228549_at | KIAA0792 gene product | 101.6146953 | 88.93841164 | 34.38370892 | 32.83997516 |
| 213959_s_at | KIAA1005 protein | 90.4966578 | 88.73778857 | 298.6459638 | 338.3340555 |
| 212557_at | KIAA1702 protein | 676.2471712 | 654.4721425 | 244.3663835 | 263.9836589 |
| 204682_at | latent transforming growth factor beta binding protein 2 | 611.5997655 | 487.8766087 | 1983.677321 | 1980.048423 |
| 218175_at | Limkain beta 2 | 280.4447842 | 314.0449214 | 1207.082501 | 1434.510573 |
| 219760_at | lin-7 homolog B (*C. elegans*) | 43.20456452 | 52.92529382 | 159.1453634 | 182.18277 |
| 205282_at | low density lipoprotein receptor-related protein 8, apolipoprotein e receptor | 51.83464995 | 55.51276568 | 167.1991217 | 143.7729064 |
| 242705_x_at | low density lipoprotein receptor-related protein associated protein 1 | 1044.05123 | 1228.622487 | 184.274917 | 178.3640072 |
| 203094_at | MAD2L1 binding protein | 1183.687435 | 1336.925357 | 442.366941 | 400.4649272 |
| 200904_at | major histocompatibility complex, class I, E | 1451.016697 | 1450.798074 | 350.6027968 | 319.8657641 |
| 202032_s_at | mannosidase, alpha, class 2A, member 2 | 575.3821055 | 653.5739787 | 173.9608312 | 179.5475684 |
| 213627_at | melanoma antigen, family D, 2 | 336.2167953 | 383.5050317 | 1019.228456 | 1131.144641 |
| 226990_at | membrane component, chromosome 11, surface market 1 | 315.0276064 | 316.446134 | 667.3521269 | 780.0775287 |
| 204656_at | mitochondrial carrier triple repeat 1 | 82.33974033 | 66.73880652 | 243.2295579 | 233.2211783 |
| 225260_s_at | mitochondrial ribosomal protein L32 | 3829.246902 | 4457.943911 | 1646.165995 | 1677.250328 |
| 228059_x_at | mitochondrial ribosomal protein S22 | 1414.07243 | 1239.674805 | 597.5565768 | 582.3441611 |
| 213164_at | mitochondrial ribosomal protein S6 | 469.4204246 | 489.7496716 | 1301.305805 | 1582.404254 |
| 235505_s_at | MRNA full length insert cDNA clone EUROIMAGE 2362292 | 424.4386285 | 321.6997632 | 60.56113986 | 72.8807163 |
| 1566257_at | MRNA; cDNA DKFZp586C1322 (from clone DKFZp586C1322) | 63.7044815 | 69.10889446 | 215.4565666 | 248.3987089 |
| 219952_s_at | Mucolipin 1 | 675.924466 | 586.847738 | 242.0886704 | 246.8697982 |
| 211926_s_at | myosin, heavy polypeptide 9, non-muscle | 534.2555339 | 511.9145667 | 1691.124313 | 1892.16041 |
| 201058_s_at | myosin, light polypeptide 9, regulatory | 705.6078429 | 766.1075869 | 5413.267491 | 4563.900384 |
| 203964_at | N-myc (and STAT) interactor | 969.752017 | 1062.774206 | 395.3902217 | 444.8967428 |
| 204125_at | NADH dehydrogenase (ubiquinone) 1 alpha subcomplex, assembly factor 1 | 1583.976006 | 1545.393409 | 648.9307843 | 662.66981 |
| 200778_s_at | neural precursor cell expressed, developmentally down-regulated 5 | 1770.648568 | 1862.88825 | 4277.128937 | 3980.894485 |
| 224773_at | neuron navigator 1 | 396.9271361 | 397.5685206 | 1290.532043 | 1511.391456 |
| 223439_at | NF-kappaB activating protein | 607.1349024 | 615.8011123 | 205.5445118 | 233.3901653 |
| 202679_at | Niemann-Pick disease, type C1 | 925.408262 | 1104.905876 | 357.5432195 | 335.5311626 |
| 209519_at | nuclear cap binding protein subunit 1, 80 kDa | 45.469754 | 43.02309688 | 118.3321705 | 124.7746706 |
| 201502_s_at | nuclear factor of kappa light polypeptide gene enhancer in B-cells inhibitor, alpha | 1663.77654 | 1501.039082 | 518.551087 | 510.0620353 |
| 205135_s_at | nuclear fragile X mental retardation protein interacting protein 1 | 468.2887275 | 540.9897258 | 163.0718005 | 163.3339801 |
| 215073_s_at | nuclear receptor subfamily 2, group F, member 2 | 191.2769142 | 188.0924709 | 1669.122773 | 1833.001419 |
| 209120_at | nuclear receptor subfamily 2, group F, member 2 | 1030.758062 | 756.9904685 | 5096.966282 | 5533.226945 |
| 209121_x_at | nuclear receptor subfamily 2, group F, member 2 | 346.5545036 | 306.8858074 | 1628.765151 | 1807.722588 |
| 244704_at | nuclear transcription factor Y, beta | 26.83793521 | 25.94994056 | 58.36306799 | 68.17996836 |
| 200875_s_at | nucleolar protein 5A (56 kDa with KKE/D repeat) | 3034.651378 | 2956.190663 | 1269.94697 | 1330.460258 |
| 200874_s_at | nucleolar protein 5A (56 kDa with KKE/D repeat) | 787.6884698 | 716.1818235 | 242.263967 | 233.9575379 |
| 204435_at | nucleoporin like 1 [BLAST] | 1702.660196 | 1347.626888 | 485.6335701 | 482.0278443 |
| 213864_s_at | nucleosome assembly protein 1-like 1 | 2251.205468 | 2257.514419 | 4888.945441 | 4669.292749 |
| 211512_s_at | opioid growth factor receptor | 128.8996328 | 123.2849601 | 56.36615753 | 60.75006373 |
| 201246_at | OTU domain, ubiquitin aldehyde binding 1 | 145.2624602 | 153.7535931 | 53.50061635 | 47.44845358 |
| 236277_at | p21 (CDKN1A)-activated kinase 3 | 150.1864522 | 129.5595357 | 506.1991361 | 462.8082813 |
| 225075_at | p53 and DNA damage regulated 1 [BLAST] | 1602.428103 | 1917.367041 | 332.0388816 | 381.342503 |
| 218371_s_at | paraspeckle component 1 | 944.1121848 | 862.5379192 | 127.7549972 | 166.5340122 |
| 203370_s_at | PDZ and LIM domain 7 (enigma) | 105.7243028 | 94.85985473 | 677.8164663 | 886.5607942 |
| 1554868_s_at | PEST-containing nuclear protein | 3221.155983 | 3304.188818 | 1516.823648 | 1588.501409 |
| 204053_x_at | phosphatase and tensin homolog (mutated in multiple advanced cancers 1) | 1151.411893 | 1209.974805 | 540.8254277 | 539.1597358 |
| 217492_s_at | phosphatase and tensin homolog (mutated in multiple advanced cancers 1), pseudogene 1 | 1355.13464 | 1310.714334 | 617.7946026 | 595.3347882 |
| 201081_s_at | phosphatidylinositol-4-phosphate 5-kinase, type II, beta | 67.86165332 | 66.88841732 | 143.8362663 | 159.9940555 |
| 207303_at | phosphodiesterase 1C, calmodulin-dependent 70 kDa | 47.49227627 | 42.77330578 | 496.8140015 | 481.6103899 |

-continued

| Name | Description | UM102605 (Induced 1) | UM040505 (Induced 5) | UM102605 (Control 2)) | UM040505 (Control 6) |
|---|---|---|---|---|---|
| 216267_s_at | Placental protein 6 | 988.6961948 | 1112.468905 | 379.3543924 | 381.4110622 |
| 224427_s_at | poly(A) polymerase gamma | 301.3870988 | 298.2112318 | 132.804783 | 115.6605887 |
| 222702_x_at | Postsynaptic protein CRIPT | 1385.056468 | 1250.580837 | 575.7641463 | 523.4114522 |
| 227942_s_at | Postsynaptic protein CRIPT | 1343.689025 | 1257.268533 | 575.8053297 | 489.5703528 |
| 221583_s_at | potassium large conductance calcium-activated channel, subfamily M, alpha member 1 | 62.91182377 | 63.58436405 | 147.7275109 | 146.357607 |
| 1555167_s_at | pre-B-cell colony enhancing factor 1 | 353.9045124 | 395.4337761 | 127.5592948 | 124.7885938 |
| 217739_s_at | pre-B-cell colony enhancing factor 1 | 1492.251147 | 1438.515665 | 489.2480709 | 562.0761745 |
| 229865_at | PRO1310 | 91.83721649 | 88.83300262 | 325.8990644 | 261.8273003 |
| 209385_s_at | proline synthetase co-transcribed homolog (bacterial) | 1205.97904 | 1461.821285 | 522.3998767 | 503.1873291 |
| 212694_s_at | propionyl Coenzyme A carboxylase, beta polypeptide | 1002.17445 | 1112.687478 | 423.1410819 | 435.0960314 |
| 211892_s_at | prostaglandin I2 (prostacyclin) synthase | 65.35097614 | 67.06275829 | 295.757091 | 399.2105925 |
| 37028_at | protein phosphatase 1, regulatory (inhibitor) subunit 15A | 1872.094108 | 2167.495906 | 632.9737567 | 510.0790608 |
| 202014_at | protein phosphatase 1, regulatory (inhibitor) subunit 15A | 1683.206408 | 2108.715647 | 385.8330483 | 296.1110007 |
| 219654_at | protein tyrosine phosphatase-like (proline instead of catalytic arginine), member a | 331.1717425 | 348.076982 | 950.8624577 | 797.1969792 |
| 221547_at | PRP18 pre-mRNA processing factor 18 homolog (yeast) | 1513.490834 | 1493.144423 | 621.5220225 | 636.7760586 |
| 209018_s_at | PTEN induced putative kinase 1 | 709.8285218 | 756.3734765 | 289.5941315 | 333.9522314 |
| 209019_s_at | PTEN induced putative kinase 1 | 761.0694514 | 777.4929091 | 234.0605301 | 255.8186717 |
| 225901_at | PTEN-like phosphatase | 736.1267236 | 732.5271439 | 224.2653336 | 238.935677 |
| 226006_at | Purkinje cell protein 2 | 1654.011398 | 1508.176289 | 618.5524513 | 685.5774779 |
| 1556123_a_at | RAB11B, member RAS oncogene family | 166.183946 | 175.9556226 | 73.34162691 | 77.35438416 |
| 204547_at | RAB40B, member RAS oncogene family | 191.5688197 | 225.3877745 | 482.3860818 | 501.5406926 |
| 204828_at | RAD9 homolog A (*S. pombe*) | 139.4069676 | 142.8373597 | 54.28666786 | 44.76092608 |
| 205333_s_at | RCE1 homolog, prenyl protein protease (*S. cerevisiae*) | 232.8450411 | 245.6752833 | 94.77657267 | 91.79308537 |
| 204243_at | rearranged L-myc fusion sequence | 834.3286169 | 928.5204589 | 189.9151252 | 235.9347623 |
| 205169_at | retinoblastoma binding protein 5 | 321.4781788 | 320.0767742 | 140.4762336 | 151.8093483 |
| 232044_at | retinoblastoma binding protein 6 | 240.2663511 | 195.1900043 | 56.93762809 | 48.54283128 |
| 239375_at | Retinoblastoma-associated protein 140 | 149.7798752 | 161.5509782 | 64.94659961 | 68.06650285 |
| 227467_at | retinol dehydrogenase 10 (all-trans) | 151.3629356 | 140.6091263 | 769.1350201 | 614.1952544 |
| 225171_at | Rho GTPase activating protein 18 | 114.891152 | 116.188706 | 521.7449064 | 626.0374601 |
| 225173_at | Rho GTPase activating protein 18 | 65.09324807 | 77.00164389 | 273.3772524 | 269.411782 |
| 203160_s_at | ring finger protein (C3HC4 type) 8 | 626.071492 | 663.3508016 | 240.3102346 | 266.1528273 |
| 1555760_a_at | RNA binding motif protein 15 | 754.266155 | 802.7536549 | 219.1319778 | 259.8363262 |
| 219286_s_at | RNA binding motif protein 15 | 1470.239315 | 1736.638771 | 360.2730723 | 431.2231024 |
| 203250_at | RNA binding motif protein 16 | 2228.868856 | 2140.312005 | 928.8640988 | 1052.668907 |
| 205115_s_at | RNA binding motif protein 19 | 351.0831006 | 400.6975799 | 150.2190403 | 138.7826461 |
| 218441_s_at | RNA polymerase II associated protein 1 | 201.57786 | 195.1248634 | 86.1260138 | 88.87007437 |
| 206499_s_at | RNA, U17D small nucleolar | 590.113462 | 561.835813 | 187.9457961 | 187.8493902 |
| 226298_at | RUN domain containing 1 | 433.9887234 | 419.8139392 | 180.1576674 | 154.6326558 |
| 222924_at | sarcolemma associated protein | 55.71446623 | 62.08007732 | 229.2083345 | 253.4216453 |
| 227557_at | scavenger receptor class F, member 2 | 494.2615935 | 558.9296294 | 152.3391398 | 148.7136646 |
| 205475_at | Scrapie responsive protein 1 | 265.6955775 | 261.4816969 | 4235.704766 | 4033.247477 |
| 214075_at | Secreted protein of unknown function | 376.8819365 | 372.7226366 | 161.9953784 | 163.0840868 |
| 206805_at | sema domain, immunoglobulin domain (Ig), short basic domain, secreted, (semaphorin) 3A | 56.64797123 | 44.95475022 | 309.9314095 | 348.1201384 |
| 225095_at | serine palmitoyltransferase, long chain base subunit 2 | 102.3597722 | 114.6123645 | 335.0256436 | 338.4665335 |
| 201739_at | serum/glucocorticoid regulated kinase | 5027.026632 | 6788.301793 | 1195.373617 | 1101.169919 |
| 200917_s_at | signal recognition particle receptor ('docking protein') | 995.6527117 | 939.8737554 | 438.2175652 | 400.7573884 |
| 216908_x_at | Similar to RNA polymerase I transcription factor RRN3 | 562.2544353 | 521.8409472 | 200.5917836 | 203.4521091 |
| 223299_at | Similar to signal peptidase complex (18 kD) | 1822.347324 | 1891.80225 | 620.7555035 | 503.1753323 |
| 224878_at | Similar to ubiquitin binding protein | 1484.127392 | 1373.299194 | 657.3135088 | 675.1301268 |
| 216977_x_at | small nuclear ribonucleoprotein polypeptide A' | 973.0685581 | 1134.188629 | 477.9128284 | 460.806823 |
| 208916_at | solute carrier family 1 (neutral amino acid transporter), member 5 | 302.6744872 | 244.551492 | 970.479204 | 1138.586455 |
| 225043_at | solute carrier family 15, member 4 | 1220.183102 | 1246.783858 | 483.392546 | 521.7135602 |
| 230494_at | solute carrier family 20 (phosphate transporter), member 1 | 267.8379408 | 238.9335123 | 662.3425387 | 796.6463565 |
| 228181_at | solute carrier family 30 (zinc transporter), member 1 | 1472.10533 | 1383.178113 | 253.4340922 | 327.769063 |
| 218826_at | solute carrier family 35, member F2 | 188.7838991 | 184.0901331 | 58.34784714 | 66.18216038 |
| 213538_at | SON DNA binding protein | 501.0248653 | 546.7923106 | 235.8211622 | 237.466031 |
| 216230_x_at | sphingomyelin phosphodiesterase 1, acid lysosomal (acid sphingomyelinase) [BLAST] | 379.1064729 | 323.456814 | 151.6203877 | 140.2956931 |
| 212455_at | Splicing factor YT521-B | 2488.456589 | 2252.569173 | 981.1153089 | 892.8306108 |

-continued

| Name | Description | UM102605 (Induced 1) | UM040505 (Induced 5) | UM102605 (Control 2)) | UM040505 (Control 6) |
|---|---|---|---|---|---|
| 244287_at | splicing factor, arginine/serine-rich 12 | 335.3635311 | 391.9740732 | 138.8080602 | 150.8984788 |
| 204914_s_at | SRY (sex determining region Y)-box 11 | 85.71872207 | 105.198644 | 833.5464347 | 906.9174587 |
| 204915_s_at | SRY (sex determining region Y)-box 11 | 43.53272004 | 52.9939065 | 285.1226083 | 262.4260104 |
| 203090_at | stromal cell-derived factor 2 | 1245.817555 | 1191.073321 | 518.8689192 | 538.9792878 |
| 204099_at | SWI/SNF related, matrix associated, actin dependent regulator of chromatin, subfamily d, member 3 | 117.7470259 | 144.0731531 | 470.7994922 | 432.2848061 |
| 202796_at | synaptopodin | 59.44395249 | 54.78490122 | 157.5521129 | 164.6035645 |
| 218327_s_at | synaptosomal-associated protein, 29 kDa | 516.6841478 | 532.1485623 | 229.2821205 | 251.7759633 |
| 203018_s_at | synovial sarcoma, X breakpoint 2 interacting protein | 43.13825789 | 39.52733336 | 106.8985491 | 128.7341548 |
| 203019_x_at | synovial sarcoma, X breakpoint 2 interacting protein | 38.54669984 | 36.27477613 | 97.44015696 | 96.36107751 |
| 235119_at | TAF3 RNA polymerase II, TATA box binding protein (TBP)-associated factor, 140 kDa | 204.7537139 | 190.2515764 | 82.91659604 | 81.26764716 |
| 203611_at | telomeric repeat binding factor 2 | 931.7955097 | 781.6726767 | 282.3745138 | 271.1241225 |
| 201434_at | tetratricopeptide repeat domain 1 | 1534.362503 | 1830.409966 | 615.431241 | 657.8365205 |
| 225180_at | tetratricopeptide repeat domain 14 | 2278.058046 | 1941.435114 | 663.9640943 | 774.2996493 |
| 208664_s_at | tetratricopeptide repeat domain 3 | 154.8151828 | 149.0723449 | 444.5033909 | 441.2076764 |
| 219248_at | THUMP domain containing 2 | 654.8901466 | 618.6353375 | 281.3541244 | 288.3049087 |
| 235737_at | Thymic stromal lymphopoietin | 221.2519297 | 178.6711339 | 812.4374364 | 798.3477116 |
| 225402_at | TP53 regulating kinase | 1293.628003 | 1482.85693 | 568.1263307 | 561.9997943 |
| 236117_at | Transcribed locus | 242.9962004 | 220.770525 | 98.13604522 | 87.75252907 |
| 244293_at | Transcribed locus | 66.172031 | 61.74335243 | 26.06576428 | 22.60010365 |
| 239370_at | Transcribed locus | 78.80949477 | 66.86673231 | 1084.788711 | 702.3071754 |
| 238065_at | Transcribed locus | 48.17880413 | 51.7014748 | 115.9272763 | 130.7869271 |
| 235831_at | Transcribed locus | 8.92077321 | 8.825701543 | 20.68537261 | 18.3175665 |
| 240214_at | Transcribed locus | 57.36023053 | 65.6324416 | 171.5043272 | 186.3661166 |
| 239069_s_at | Transcribed sequences | 424.9019452 | 441.6037972 | 148.9318796 | 163.0704008 |
| 205255_x_at | transcription factor 7 (T-cell specific, HMG-box) | 103.8766082 | 125.6165274 | 690.9518929 | 536.2135774 |
| 203177_x_at | transcription factor A, mitochondrial | 696.7690121 | 646.0264544 | 240.629806 | 257.0165432 |
| 204849_at | transcription factor-like 5 (basic helix-loop-helix) | 155.5619862 | 123.0933464 | 582.3635992 | 566.7631557 |
| 217965_s_at | Transcriptional regulator protein | 1418.699492 | 1557.442784 | 557.6297339 | 507.4437426 |
| 228834_at | transducer of ERBB2, 1 | 1869.17998 | 1589.458365 | 610.1456625 | 551.06798 |
| 202704_at | transducer of ERBB2, 1 | 2670.432104 | 2530.896795 | 874.5707014 | 1016.145532 |
| 218188_s_at | translocase of inner mitochondrial membrane 13 homolog (yeast) | 1800.735909 | 1594.781744 | 678.7282025 | 636.0259065 |
| 230571_at | transmembrane 4 superfamily member 11 (plasmolipin) | 171.9330603 | 128.8112163 | 34.95938017 | 31.72104144 |
| 222477_s_at | transmembrane 7 superfamily member 3 | 1315.67618 | 1221.790007 | 568.3206019 | 528.8504559 |
| 223089_at | Transmembrane protein vezatin | 144.8859532 | 136.9059724 | 456.8431235 | 421.7250178 |
| 223436_s_at | TRNA splicing 2' phosphotransferase 1 | 108.8408333 | 118.7980286 | 296.9678903 | 294.357888 |
| 211701_s_at | trophinin | 89.58122877 | 96.73743992 | 206.1570129 | 210.1683705 |
| 206116_s_at | tropomyosin 1 (alpha) | 1207.955398 | 1310.308148 | 7242.094569 | 6954.194334 |
| 223501_at | tumor necrosis factor (ligand) superfamily, member 13b [BLAST] | 65.51306223 | 56.91425676 | 24.35726894 | 22.95522085 |
| 207643_s_at | tumor necrosis factor receptor superfamily, member 1A | 2394.994075 | 2168.39941 | 833.9583111 | 943.7611036 |
| 207536_s_at | tumor necrosis factor receptor superfamily, member 9 | 13.03584058 | 15.62996047 | 36.75770797 | 36.82971101 |
| 210609_s_at | tumor protein p53 inducible protein 3 | 1240.303919 | 1016.439688 | 392.4085006 | 382.4371009 |
| 216449_x_at | tumor rejection antigen (gp96) 1 | 12606.70604 | 15410.08498 | 3423.073874 | 3117.832303 |
| 221490_at | Ubiquitin associated protein 1 | 879.7164737 | 842.7440902 | 214.9801856 | 274.2091468 |
| 214169_at | unc-84 homolog A (C. elegans) | 142.0209496 | 145.1993248 | 34.9883395 | 42.11820982 |
| 212180_at | v-crk sarcoma virus CT10 oncogene homolog (avian)-like | 1507.095069 | 1339.651514 | 568.9971402 | 628.6339653 |
| 212983_at | v-Ha-ras Harvey rat sarcoma viral oncogene homolog | 1171.900339 | 998.5920342 | 460.7468407 | 484.7331427 |
| 204254_s_at | vitamin D (1,25-dihydroxyvitamin D3) receptor | 519.985718 | 501.9311425 | 115.3236649 | 107.0835378 |
| 209375_at | xeroderma pigmeritosum, complementation group C | 874.0870829 | 842.7408754 | 211.0858412 | 231.7555153 |
| 218767_at | XPMC2 prevents mitotic catastrophe 2 homolog (Xenopus laevis) | 640.1446975 | 546.6502307 | 187.2487763 | 189.9507181 |
| 225959_s_at | zinc and ring finger 1 | 106.2031506 | 108.1427517 | 257.2168762 | 260.3250736 |
| 239937_at | zinc finger protein 207 | 169.788238 | 151.5572845 | 41.08117329 | 41.39673405 |
| 235717_at | Zinc finger protein 229 | 33.87951985 | 34.27737716 | 75.36125485 | 70.31415147 |
| 236075_s_at | zinc finger protein 232 | 351.9208109 | 408.6731169 | 157.4172431 | 149.790303 |
| 219123_at | zinc finger protein 252 | 283.4557717 | 325.2988384 | 116.5319355 | 130.7157891 |
| 202051_s_at | Zinc finger protein 262 | 261.1202381 | 255.5187673 | 593.7282247 | 631.0582586 |
| 1555337_a_at | zinc finger protein 317 | 411.4592815 | 412.5842525 | 98.80646259 | 95.97176295 |
| 204139_x_at | zinc finger protein 42 (myeloid-specific retinoic acid-responsive) | 160.1355618 | 175.9278532 | 55.91116732 | 64.49989828 |
| 210336_x_at | zinc finger protein 42 (myeloid-specific | 256.9969352 | 242.1254976 | 64.79929277 | 78.74556076 |

| Name | Description | UM102605 (Induced 1) | UM040505 (Induced 5) | UM102605 (Control 2)) | UM040505 (Control 6) |
|---|---|---|---|---|---|
| | retinoic acid-responsive) | | | | |
| 220086_at | zinc finger protein, subfamily 1A, 5 | 341.0702509 | 278.9497096 | 111.0078507 | 102.2415764 |
| 220473_s_at | zinc finger, CCHC domain containing 4 | 163.8694497 | 161.1077203 | 77.17661647 | 68.65821284 |
| 1555982_at | zinc finger, FYVE domain containing 16 [BLAST] | 38.86480231 | 45.21894095 | 104.8918462 | 113.3543033 |

Other Embodiments

While the invention has been described in conjunction with the foregoing detailed description and examples, the foregoing description and examples are intended to illustrate and not to limit the scope of the invention, which is defined by the scope of the appended claims. Other aspects, advantages, and modifications are within the scope of the claims.

What is claimed is:

1. A method of producing a population of cells having a respiratory epithelial cell phenotype, said method comprising culturing a purified population of human fetal blood multi-lineage progenitor cells (MLPC) or a clonal line of human fetal blood MLPC with a differentiation medium effective to induce differentiation of said MLPC into cells having said respiratory epithelial cell phenotype, wherein said MLPC within said purified population or clonal line are positive for CD9, CD13, CD29, CD44, CD73, CD90 and CD105, and, negative for CD10, CD34, CD41, CD45, Stro-1, stage specific embryonic antigen (SSEA)-3, and SSEA-4.

2. The method of claim 1, wherein said differentiation medium comprises hydrocortisone, epidermal growth factor, insulin, triiodothyronine, transferrin, bovine serum albumin, retinoic acid, pituitary extract, and epinephrine.

3. The method of claim 1, further comprising testing said cells having said respiratory epithelial cell phenotype for surfactant protein C.

4. The method of claim 3, wherein testing said cells having said respiratory epithelial cell phenotype comprises staining said cells with an antibody having binding affinity for prosurfactant protein C.

5. A method for producing a population of cells having a respiratory epithelial cell phenotype from human fetal blood, said method comprising:
   a) contacting a human fetal blood sample with a composition, said composition comprising:
      i) dextran;
      ii) anti-glycophorin A antibody;
      iii) anti-CD 15 antibody; and
      iv) anti-CD9 antibody;
   b) allowing said sample to partition into an agglutinate and a supernatant phase;
   c) recovering cells from said supernatant phase;
   d) purifying MLPC from the recovered cells by adherence to a solid substrate, wherein said MLPC are positive for CD9 and positive for CD45;
   e) culturing said MLPC such that said MLPC obtain a fibroblast morphology, wherein said MLPC having said fibroblast morphology are positive for CD9, CD13, CD29, CD44, CD73, CD90 and CD105, and, negative for CD10, CD34, CD41, CD45, Stro-1, SSEA-3, and SSEA-4; and
   f) culturing said MLPC having said fibroblast morphology with a differentiation medium effective to induce differentiation of said MLPC into cells having said respiratory epithelial cell phenotype.

6. The method of claim 5, said method further comprising testing said cells having said respiratory epithelial cell phenotype for surfactant protein C.

7. The method of claim 5, said method further comprising producing a clonal line of MLPC from said MLPC having said fibroblast morphology before culturing with said differentiation medium.

* * * * *